United States Patent
Fernandes et al.

(10) Patent No.: US 12,171,743 B2
(45) Date of Patent: *Dec. 24, 2024

(54) FORMS OF ATICAPRANT

(71) Applicant: Janssen Pharmaceuticals, Inc., Titusville, NJ (US)

(72) Inventors: Philippe Fernandes, Beerse (BE); Mark Schmidt, Antwerp (BE); Vanina Popova, Nijlen (BE); Adam Savitz, Greenwich, CT (US); Rama Melkote, Basking Ridge, NJ (US); Wayne C. Drevets, Rancho Santa Fe, CA (US); Srihari Gopal, Belle Mead, NJ (US); Darrel Pemberton, Oud Turnhout (BE); Chakradhar Lagishetty, King of Prussia, PA (US); Iva Kezic, Antwerp (BE)

(73) Assignee: Janssen Pharmaceuticals, Inc., Titusville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/679,720

(22) Filed: May 31, 2024

(65) Prior Publication Data

US 2024/0316003 A1 Sep. 26, 2024

Related U.S. Application Data

(63) Continuation of application No. 18/178,961, filed on Mar. 6, 2023, now Pat. No. 11,998,524.

(60) Provisional application No. 63/317,475, filed on Mar. 7, 2022.

(51) Int. Cl.
*A61K 31/40* (2006.01)
*A61P 25/24* (2006.01)

(52) U.S. Cl.
CPC .............. *A61K 31/40* (2013.01); *A61P 25/24* (2018.01); *C07B 2200/13* (2013.01)

(58) Field of Classification Search
CPC ...... A61K 31/40; A61P 25/24; C07B 2200/13
See application file for complete search history.

(56) References Cited

U.S. PATENT DOCUMENTS

| | | | |
|---|---|---|---|
| 5,457,208 A | 10/1995 | Portoghese et al. |
| 6,391,873 B1 | 5/2002 | Jenck et al. |
| 6,528,518 B2 | 3/2003 | Carlezon, Jr. |
| 7,196,100 B2 | 3/2007 | Benesh et al. |
| 7,288,543 B2 | 10/2007 | Broughton et al. |
| 7,378,448 B2 | 5/2008 | Mitch et al. |
| 7,381,719 B2 | 6/2008 | Blanco-Pillado et al. |
| 7,381,750 B2 | 6/2008 | De et al. |
| 7,396,943 B2 | 7/2008 | Benesh et al. |
| 7,399,774 B2 | 7/2008 | Siegel et al. |
| 7,414,132 B2 | 8/2008 | De et al. |
| 7,531,557 B2 | 5/2009 | Mitch |
| 7,560,463 B2 | 7/2009 | Mitch et al. |
| 7,709,522 B2 | 5/2010 | Buezo et al. |
| 8,063,059 B2 | 11/2011 | Hermann |
| 8,173,695 B2 | 5/2012 | Diaz et al. |
| 10,676,469 B2 | 6/2020 | Roberts et al. |
| 11,266,627 B1 | 3/2022 | Schmidt et al. |
| 2002/0052365 A1 | 5/2002 | Hanns et al. |
| 2004/0082573 A1 | 4/2004 | Cook et al. |
| 2006/0052439 A1 | 3/2006 | Beguin et al. |
| 2007/0155793 A1 | 7/2007 | Benesh |
| 2007/0213394 A1 | 9/2007 | Beguin et al. |
| 2008/0207701 A1 | 8/2008 | Chappell et al. |
| 2008/0255152 A1 | 10/2008 | Blanco-Pillado et al. |
| 2008/0269296 A1 | 10/2008 | Blanco-Pillado et al. |
| 2009/0023785 A1 | 1/2009 | Pedregal-Tercero et al. |
| 2009/0196824 A1 | 8/2009 | Elman et al. |
| 2010/0197669 A1 | 8/2010 | Diaz Buezo et al. |
| 2013/0303497 A1 | 11/2013 | Hansen et al. |
| 2015/0005315 A1 | 1/2015 | Carroll et al. |
| 2016/0310488 A1 | 10/2016 | Morillo et al. |

(Continued)

FOREIGN PATENT DOCUMENTS

| | | | |
|---|---|---|---|
| CN | 114195693 A | * | 3/2022 |
| WO | 02/53533 A2 | | 7/2002 |

(Continued)

OTHER PUBLICATIONS

Peckham et al. Kappa opioid receptor antagonism (Mental Health Clinician, 8: 175-183). (Year: 2018).*

"Guidance for Industry—Q3A Impurities in New Drug Substances", Revision 2, U.S. Department of Health and Human Services, Jun. 2008, pp. 1-14.

A-Hakeim et al., "In major depression, increased serum dynorphin and kappa opioid receptor levels are positively associated with mu opioid receptor levels and immune activation and are attenuated by nicotine dependence", ResearchGate, XP093024086, Apr. 1, 2019, pp. 1-39.

Anton et al., "American College of Neuropsychopharmacology", Annual Meeting Abstracts—13, Nashville, TN, ACNP, 2007, vol. 13, Issue 3, pp. 1-12.

(Continued)

*Primary Examiner* — Matthew P Coughlin
*Assistant Examiner* — Meghan C Heasley
(74) *Attorney, Agent, or Firm* — BakerHostetler

(57) ABSTRACT

The disclosure provides crystalline and amorphous forms of aticaprant. Also provided by the disclosure are pharmaceutical compositions comprising the amorphous or crystalline forms, methods of treating major depressive disorder using the amorphous or crystalline forms of aticaprant, amorphous or crystalline forms of aticaprant for use in the treatment of major depressive disorder in a human patient having anhedonia, uses of the amorphous or crystalline forms of aticaprant in the manufacture of a medicament for the treatment of major depressive disorder, and packages or pharmaceutical products comprising (i) amorphous or crystalline forms of aticaprant and (ii) instructions for treating major depressive disorder. In some aspects, the human patient treated as described herein has anhedonia.

30 Claims, 34 Drawing Sheets

(56) References Cited

U.S. PATENT DOCUMENTS

| | | |
|---|---|---|
| 2018/0072654 A1 | 3/2018 | Schmidhammer et al. |
| 2018/0148432 A1 | 5/2018 | Kablaoui et al. |
| 2018/0169065 A1 | 6/2018 | Kellar et al. |
| 2019/0008806 A1 | 1/2019 | Singh et al. |
| 2019/0023700 A1 | 1/2019 | Guerrero et al. |
| 2019/0117637 A1 | 4/2019 | Frazer et al. |
| 2019/0240293 A1 | 8/2019 | Weinstein et al. |
| 2019/0255036 A1 | 8/2019 | Kariman |
| 2019/0263781 A1 | 8/2019 | Carroll et al. |
| 2019/0298703 A1 | 10/2019 | Bhide et al. |
| 2020/0121236 A1 | 4/2020 | Gao et al. |
| 2020/0171025 A1 | 6/2020 | Parella et al. |
| 2021/0024576 A1 | 1/2021 | Aldrich et al. |
| 2021/0047310 A1 | 2/2021 | Roberts et al. |
| 2022/0370409 A1 | 11/2022 | Schmidt et al. |
| 2023/0233525 A1 | 7/2023 | Schmidt et al. |
| 2023/0277500 A1 | 9/2023 | Goyvaerts et al. |
| 2023/0348377 A1 | 11/2023 | Surmont et al. |

FOREIGN PATENT DOCUMENTS

| | | |
|---|---|---|
| WO | 2004/026305 A1 | 4/2004 |
| WO | 2008/021849 A2 | 2/2008 |
| WO | 2008/021851 A2 | 2/2008 |
| WO | 2008/032156 A1 | 3/2008 |
| WO | 2009/094260 | 7/2009 |
| WO | 2015/091833 A1 | 6/2015 |
| WO | 2016/156396 A1 | 10/2016 |
| WO | 2016/191763 A2 | 12/2016 |
| WO | 2017/218518 A1 | 12/2017 |
| WO | 2018/022664 A1 | 2/2018 |
| WO | 2018/022666 A1 | 2/2018 |
| WO | 2018/022668 A2 | 2/2018 |
| WO | 2018/053222 A1 | 3/2018 |
| WO | 2018/096510 A1 | 5/2018 |
| WO | 2018/170492 A1 | 9/2018 |
| WO | 2019/183556 A1 | 9/2019 |
| WO | 2020/086729 A1 | 4/2020 |
| WO | 2022/234457 A1 | 11/2022 |

OTHER PUBLICATIONS

Avis et al., "Pharmaceutical Dosage Forms", Parenteral Medications, 1992, vol. 1-2, pp. 1-9.

Beardsley et al., "Differential effects of the novel kappa opioid receptor antagonist, JDTic, on reinstatement of cocaine seeking induced by footshock stressors vs cocaine primes and its antidepressant-like effects in rats", Psydlopharmacology, 2005, vol. 183, pp. 118-126.

Berge et al., "Pharmaceutical Salts", Journal of Pharmaceutical Sciences, Jan. 1977, vol. 66 No. 1, pp. 1-19.

Berman et al., "The Efficacy and Safety of Aripiprazole as Adjunctive Therapy in Major Depressive Disorder: A Multicenter, Randomized, Double-Blind, Placebo-Controlled Study", J Clin Psychiatry, 2007, vol. 68 Issue 6, pp. 843-853.

Blendov et al., "Reduced alcohol consumption in mice lacking preprodynorphin", Alcohol, Oct. 2006, vol. 40 No. 2, pp. 1-23.

Borbely et al., "Novel drug developmental strategies for treatment-resistant depression," Br. J. Pharmacol., 2022, vol. 179, pp. 1146-1186.

Bortolato et al., "Kappa Opioid Receptor Activation Disrupts Prepulse Inhibition of the Acoustic Startle in Rats", Biol. Psychiatry, Jun. 2005, vol. 57 Issue 12, pp. 1-6.

Bouwknecht et al., "The stress-induced hyperthermia paradigm as a physiological animal model for anxiety: A review of pharmacological and genetic studies in the mouse", Neuroscience and Biobehavioral Reviews, 2007, vol. 31 Issue 1, pp. 1-6.

Browne et al., "Targeting opioid dysregulation in depression for the development of novel therapeutics", Pharmacol. Ther., Sep. 2019, vol. 201, pp. 51-76.

Caira M R, "Crystalline Polymorphism Of Organic Compounds", Topics In Current Chemistry, Springer, Berlin, DE, 1998, vol. 198, ISSN 0340-1022, pp. 163-208.

Carey et al., "Advanced Organic Chemistry. Part B: Reactions and Synthesis. Fourth Edition", Molecules, 2001, vol. 6, pp. 1-3.

Carroll et al., "N Substituted 4!3-Methyl-5-(3°hydroxyphenyl)-7a-amidomorphans Are Potent, Selective K Opioid Receptor Antagonists", J. Med. Chem., 2006, vol. 49 No. 5, pp. 1781-1791.

Cheng et al., "Relationship Between the Inhibition Constant (K1) And the Concentration of Inhibitor which causes 50 per cent Inhibition ((150) an Enzymatic Reaction", Biochem Pharmacol., 1973, vol. 22, pp. 3099-3108.

Chow, "Bioavailabilily and Bioequivalence in Drug Development", Wiley interdisciplinary reviews, Computational statistics, 2014, vol. 6, pp. 304-312.

Co-occurring Alcohol Use Disorder and Schizophrenia, Health, Retrieved from: https://athealth.com/topics/co-occurring-alcohol-use-disorder-and-schizophrenia 2/, 2013, pp. 1-9.

Cornelius et al., "Alcohol and psychiatric comorbidity", Recent Dev. Alcoholism, 2003, vol. 16, pp. 361-374.

Custodio-Patsey et al., "Sex differences in kappa opioid receptor inhibition of latent postoperative pain sensitization in dorsal horn", Neuropharmacology, 2020, vol. 163, 107726.

Delapp et al., "Determination of [35S] Guanosine-5'-O-(3-thio) Triphosphate Binding Mediated by Cholinergic Muscarinic Receptors in Membranes from Chinese Hamster Ovary Cells and Rat Striatum Using an Anti-G Protein Scintillation Proximity Assay1", Journal of Pharmacology and Experimental Therapeutics, JPET, 1999, vol. 289 No. 2, pp. 946-955.

Diagnostic and Statistical Manual of Mental Disorders, DSM-IV-TR., Revised 4th Ed., Text Revision, pp. 1-4, 2000.

Dolle et al., "Nascent Structure-Activity Relationship Study of a Diastereomeric Series of Kappa Opioid Receptor Antagonists Derived from CJ-15,208", Bioorganic & Medicinal Chemistry Letters, , Jul. 2009, vol. 19 Issue 13, pp. 1-4.

Domi et al., "Preclinical evaluation of the kappa-opioid receptor antagonist CERC-501 as a candidate therapeutic for alcohol use disorders", Neuropsychopharmacology, 2018, vol. 43, pp. 1805-1812.

El-Khalili et al., "Extended-release quetiapine fumarate (quetiapine XR) as adjunctive therapy in major depressive disorder (MOD) in patients with an inadequate response to ongoing antidepressant treahnent: a multicentre, randomized, double-blind, placebo-controlled study", International J Neuropsychophannacol., 2010, vol. 13, pp. 917-932.

Emmerson et al., "Characterization of Opioid Agonist Efficacy in a C6 Glioma Cell Line Expressing the μ Opioid Receptor1", J. Pharm Exp Ther., 1996, vol. 278 No. 3, pp. 1121-1127.

European Clinical Trial Register Protocol for EudraCT No. 2019-000695-41, "A Phase 2a Randomized, Double-blind, Placebo-Controlled, Parallel-Group, Multi-center Study Investigating the Efficacy, Safety, Tolerability and Pharmacokinetics of JNJ-67953964 in Subjects with Major Depressive Disorder", pp. 1-7, Entry Date: Apr. 26, 2019.

Fava et al., "Double-blind, placebo-controlled, proof-of-concept trial of a kappa-selective opioid receptor antagonist augmentation in treatment-resistant depression", Annals of Clinical Psychiatry: Official Journal of the American Academy of Clinical Psychiatrists, Nov. 2020, 1, vol. 32, No. 4, pp. e16-e24.

Geyer et al., "Pharmacological studies of prepulse inhibition models of sensorimotor gating deficits in schizophrenia: a decade in review", Psych opharmacology, 2001, vol. 156, pp. 117-154.

Grant et al., "Prevalence and Co-occurrence of Substance Use Disorders and Independent Mood and Anxiety Disorders", Arch Gen Psychiatry, Aug. 2004, vol. 61, pp. 807-816.

Gregg et al., "Reasons for increased substance use in psychosis", Clinical Psychology Review, 2007, vol. 27, pp. 494-510.

Healey et al., "Pharmaceutical solvates, hydrates and amorphous forms: A special emphasis on cocrystals", Advanced Drug Delivery Reviews, Mar. 22, 2017, vol. 117, pp. 25-46.

Healey et al., "Pharmaceutical solvates, hydrates and amorphous forms: A special emphasis on cocrystals", Advanced Drug Delivery Reviews, vol. 117, Mar. 22, 2017, pp. 25-46.

(56) References Cited

OTHER PUBLICATIONS

Impurities: Guide for Residual Solvents Q3C(R8), ICH Harmonised Guideline, pp. 1-50, Apr. 22, 2021.

International Search Report and Written Opinion received for PCT Application No. PCT/IB2022/054085, mailed on Sep. 9, 2022, pp. 1-14.

International Search Report and Written Opinion received for PCT Application No. PCT/IB2023/050170, Mailed on Feb. 23, 2023, pp. 1-15.

International Search Report and Written Opinion received for PCT Application No. PCT/IB2023/052088, Mailed on May 31, 2023, pp. 1-17.

International Search Report and Written Opinion received for PCT Application No. PCT/US2009/030811, Mailed on Apr. 8, 2009, pp. 1-9.

Jackson et al., "Effects of orally-bioavailable short-acting kappa opioid receptor-selective antagonist LY2456302 on nicotine withdrawal in mice", Neuropharmacology, 2015, pp. 270-274.

Jacobson et al., "Sex differences in the modulation of mouse nest building behavior by Kappa Opioid receptor signaling", Neuropharmacology, 2020, vol. 177, 108254, pp. 1-9.

Jacobson et al., "The kappa opioid receptor antagonist aticaprant reverses behavioral effects from unpredictable chronic mild stress in male nice", Psychopharmacology, 2020, vol. 237, pp. 3715-3728.

Jones et al., "5'-Guanidinonaltrindole, a highly selective and potent K opioid receptor antagonist", European Journal of Pharmacology, May 2000, vol. 396, Issue 1, pp. 1-6.

Jones et al., "A randomized, double-blind, placebo-controlled study of the kappa opioid receptor antagonist, CERC-501, in a human laboratory model of smoking behavior", Addiction Biology, Jun. 2019, e12799, pp. 1-9.

Knoll et al., "Anxiolytic-Like Effects of K-Opioid Receptor Antagonists in Models of Unlearned and Learned Fear in Rats", J Phrmacol. Experimental Therapeutics., 2007, vol. 323, No. 3, pp. 838-845.

Kovacs et al., "Decreased Oral Self-Administration of Alcohol in K-Opioid Receptor Knock-Out Mice", Alcoholism: Clinical and Experimental Research, May 2005, vol. 29, No. 5, pp. 730-738.

Krystal et al., "A randomized proof-of-mechanism trail applying the 'fast-fail' approach to evaluating K-opioid antagonism as a treatment for anhedonia", Nature Medicine, May 2020, vol. 26, pp. 760-768.

Krystal et al., ACNP 58th Annual Meeting: Panels, Mini-Panels and Study Groups, Neuropsychopharmacology, 2019, vol. 44, pp. 1-77.

Li et al., "A Novel 18F-labeled kappa opioid receptor antagonist as PET radiotracer: Synthesis and in vivo Evaluation", The Journal of Nuclear Medicine, May 2016, vol. 57, Supp. 2, 159, pp. 1-3.

Li et al., "Development and In Vivo Evaluation of a K-Opioid Receptor Agonist as a PET Radiotracer with Superior Imaging Characteristics", The Journal of Nuclear Medicine, Jul. 2019, vol. 60, No. 7, pp. 1023-1030.

Li et al., "Novel 18F-Labeled k-Opioid Receptor Antagonist as PET Radiotracer: Synthes and In Vivo Evaluation of 18F-LY2459989 in Nonhuman Primates", The Journal of Nuclear Medicine, Jan. 2018, vol. 69, No. 1, pp. 140-146.

Lieberman et al., "Pharmaceutical Dosage Forms: Disperse Systems", vols. 1-2, published by Marcel Dekker Inc., 1990, pp. 1-10.

Lieberman et al., "Pharmaceutical Dosage Forms: Tablets, Second Edition", Revised and Expanded, 1990, vol. 1-3, pp. 1-9.

MacRae et al., "Mercury: Visualization and analysis of crystal structures", J. Appl. Cryst., Jun. 2006, vol. 39 Part 3, pp. 1-8.

Mague, et al., "Antidepressant-Like Effects of K-Opioid Receptor Antagonists in the Forced Swim Test in Rats," The Journal of Pharmacology and Experimental Therapeutics, 2003, vol. 305, No. 1, pp. 323-330.

Marcus et al., "The Efficacy and Safety of Aripiprazole as Adjunctive Therapy in Major Depressive Disorder, A Second Multicenter, Randomized, Double-Blind, Placebo-Controlled Study", J. Clin. Psychopharmacol, Apr. 2008, vol. 28 No. 2, pp. 156-165.

McCann, "Potential of Buprenorphine/Naltrexone in Treating Polydrug Addiction and Co-occurring Psychiatric Disorders", Clinical Pharmacology & Therapeutics, Apr. 2008, vol. 83, No. 4, pp. 627-630.

McLaughlin et al., "K Opioid Receptor Antagonism and Prodynorphin Gene Disruption Block Stress-Induced Behavioral Responses", The Journal of Neuroscience, Jul. 2003, vol. 23, No. 13, pp. 5674-5683.

National Institute of Mental Health, "Depression, Bethesda: National Institute of Mental Health Publication No. 02-3561", 2002, pp. 1-25.

Olivier et al., "Stress-induced hyperthermia and anxiety: pharmacological validation", European Journal of Pharmacology, 2003, vol. 463, pp. 117-132.

Pae et al., "Aripiprazole as Adjunctive Therapy for Patients with Major Depressive Disorder: Overview and Implications of Clinical Trial Data", CNS Drugs, 2011, vol. 25 No. 2, pp. 109-127.

Paulekuhn et al., "Trends in Active Pharmaceutical Ingredient Salt Selection based on Analysis of the Orange Book Database", J. Med. Chem., 2007, vol. 50 No. 26, pp. 6665-6672.

Peckham, "Kappa opioid receptor antagonism: Are opioids the answer for treatment resistant depression?," Review of Drugs/Pharmacotherapy, 2018, vol. 8, No. 4, pp. 175-183.

Petit-Demouliere et al., "Forced swimming test in mice: a review of antidepressant activity", Psychopharmacology, 2005, vol. 177, pp. 245-255.

Pizzagalli et al. "Selective kappa-opioid antagonism ameliorates anhedonic behavior: evidence from the Fast-fail Trial in Mood and Anxiety Spectrum Disorders (FAST-MAS)," Neuropsychopharmacol., 2020, vol. 45, pp. 1656-1663.

Portoghese et al., "Binaltorphimine-Related Bivalent Ligands and Their Kappa Opioid Receptor Antagonist Selectivity", J. Med. Chem., 1988, vol. 31 No. 4, pp. 1-13.

Reed et al., "Kappa Opioid Receptor Antagonists as Potential Therapeutics for Mood and Substance Use Disorders". In: Handbook of Experimental Pharmacology, 2020, vol. 271, Springer, Cham., (abstract only).

Reed et al., "Repeated Administration of Opra Kappa (LY2456302), a Novel Short-Acting, Selective KOP-r Antagonist, in Persons with and without Cocaine Dependence", Neuropsychopharmacology, 2018, No. 43, pp. 739-750.

Referencing Approved Drug Products in ANDA Submissions—Guidance for Industry, U.S. Department of Health and Human Services, Generics, Oct. 2020, pp. 1-18.

Roman et al., "Novel neuroimmunologic therapeuticsin depression: A clinical perspective on what we know so far", Brain, Behavior and Immunity, Academic Press, San Diego, CA, US, Sep. 21, 2019, vol. 83, pp. 7-21, XP085943201.

Rorick-Kehn et al., "Determining Pharmacological Selectivity of the Kappa Opioid Receptor Antagonist LY2456302 Using Pupillometry as a Translational Biomarker in Rat and Human", International Journal of Neuropsychopharmacology, 2015, pp. 1-11.

Rorick-Kehn et al., "LY2456302 is a novel, potent, orally-bioavailable small molecule kappa-selective antagonist with activity in animal models predictive of efficacy in mood and addictive disorders", Neuropharmacology, 2014, vol. 77, pp. 131-144.

Rothman et al., "An open-label study of a functional opioid K antagonist in the treatment of opioid dependence", Journal of Substance Abuse Treatment, 2000, vol. 18, pp. 277-281.

Schuckit, "Comorbidity between substance use disorders and psychiatric conditions", Addiction, 2006, vol. 101, Supp. 1, pp. 76-88.

Shippenberg et aL, "Dynorphin and the pathophysiology of drug addiction", Pharmacology & Therapeutics, 2007, vol. 116 No. 2, pp. 1-30.

Smith et al., "March's Advanced Organic Chemistry, Reactions Mechanisms, and Structure, 5th Edition", Molecules, 2001, vol. 6, Wiley Interscience, pp. 10164-10165.

Stahl et al., "Handbook of Pharmaceutical Salts", International Union of Pure and Applied Chemistry, Index, 2002, pp. 1-3.

Stevens, et al., "Potent and Selective Indolomorphin an Antagonists of the Kappa-Opi aid Receptor", J. Med. Ch em., 2000, vol. 43, pp. 2759-2769.

Swerdlow et al., "Neural circuit regulation of prepulse inhibition of startle in the rat: current knowledge and future challenges", Psychophannacology, 2001, vol. 156, pp. 194--215.

(56) References Cited

OTHER PUBLICATIONS

Thase et al., "Adjunctive Brexpiprazole 1 and 3 mg for Patients with Major Depressive Disorder Following Inadequate Response to Antidepressants: A Phase 3, Randomized, Double-Blind Study", J Clinical Psychialiy, 2015, vol. 76 No. 9, pp. 1-17.
Thase et al.,"Efficacy and Safety of Adjunctive Brexpiprazole 2 mg in Major Depressive Disorder", J Clinical Psychiatry, vol. 76 No. 9, 15 pages, 2015.
The International Classification of Diseases, Tenth Revision (ICD-10), National Centre for Health Statistics, 2015, pp. 1-2.
Thomas et al., "Discovery of an Opioid K Receptor Selective Pure Antagonist from a Library of N-Substituted 413-Methyl-5-(3-hydroxyphenyl) morphans", J. Med. Chem., 2002, vol. 45, pp. 3524-3530.
Thomas et al., "Identification of (3R)-7-Hydroxy-N-((1S )-1-2-methylpropy 1)-1,2,3,4-tetrahydro-3-isoquinolinecarboxamide as a Novel Potent and Selective Opioid K Receptor Antagonist", J. Med. Chem., 2003,vol. 46 No. 14, pp. 3127-3137.
Thomas, et al., "Importance of Phenolic Address Groups in Opioid Kappa Receptor Selective Antagonists", J. Med. Chem, 2004, vol. 47 No. 4, pp. 1070-1073.
U.S. Department of Health and Human Services, "National Institutes of Health NIH Publication 06-3879", Rockville, MD, 2006, pp. 1-28.
Undurraga et al., "Randomized, Placebo-Controlled Trials of Antidepressants for Acute Major Depression: Thirty-Year Meta-Analytic Review", Neuropsychopharmacology, 2012, vol. 37, No. 4, pp. 851-864.
Urbano et al., "Antagonists of the kappa opioid receptor", Bioorganic & Medicinal Chemistry Letters, 2014, vol. 24, pp. 2021-2032, 2014.
US Clinical Trial Posting for NCT01913535, "Proof-of-Concept Trial of LY2456302 Augmentation of Antidepressant Therapy in Treatment-Resistant Depression", pp. 1-10, Submission Date: Apr. 7, 2015, Estimated Posting Date: Apr. 9, 2015.
US Clinical Trial Posting for NCT01913535, "Proof-of-Concept Trial of LY2456302 Augmentation of Antidepressant Therapy in Treatment-Resistant Depression", pp. 1-38, Submission Date: May 31, 2017, Posting Date: Jul. 2, 2017.
US Clinical Trial Posting for NCT01913535, "Proof-of-Concept Trial of LY2456302 Augmentation of Antidepressant Therapy in Treatment-Resistant Depression", pp. 1-5, Submission Date: Jul. 30, 2013, Estimated: Posting Date Aug. 1, 2013.
US Clinical Trial Posting for NCT03559192, "A Phase 2a Randomized, Double-blind, Placebo-Controlled, Parallel-Group, Multicenter Study Investigating the Efficacy, Safety, Tolerability and Pharmacokinetics of JNJ-67953964 in Subjects With Major Depressive Disorder", pp. 1-13, Submission Date: Dec. 4, 2018, Posting Date: Dec. 5, 2018.
US Clinical Trial Posting for NCT03559192, "A Phase 2a Randomized, Double-blind, Placebo-Controlled, Parallel-Group, Multicenter Study Investigating the Efficacy, Safety, Tolerability and Pharmacokinetics of JNJ-67953964 in Subjects With Major Depressive Disorder", pp. 1-14, Submission Date: Apr. 22, 2019, Posting Date: Apr. 23, 2019.
US Clinical Trial Posting for NCT03559192, "A Phase 2a Randomized, Double-blind, Placebo-Controlled, Parallel-Group, Multicenter Study Investigating the Efficacy, Safety, Tolerability and Pharmacokinetics of JNJ-67953964 in Subjects With Major Depressive Disorder", pp. 1-4, Submission Date: Jun. 6, 2018, Posting Date: Jun. 18, 2018.
Vidal, et al., "Assignment of Absolute Configuration on the Basis of the Conformational Effects Induced by Chiral Derivatizing Agents: The 2-Arylpyrrolidine Case", Organic Letters, 2007, vol. 9 No. 21, pp. 1-6.
Walker, et al., "Pharmacological Evidence for a Motivational Role of K-Opioid Systems in Ethanol Dependence", Neuropsychophannacology, 2008, vol. 33, pp. 643-652.
Williams et al., "Acute inhibition of kappa opioid receptors before stress blocks depression like behaviors in California mice", Progress in Neuropsychopharmacology & Biological Psychiatry, 2018, vol. 86, pp. 166-174.
Zheng et al., "Synthesis and Evaluation of 11C-LY2795050 as a k-Opioid Receptor Antagonist Radiotracer for PET Imaging", The Journal Nuclear Medicine, Mar. 2013, vol. 54, No. 3, 455-463.
Zheng et al., "Synthesis and Evaluation of 11C-LY2795050 as a k-Opioid Receptor Antagonist Radiotracer for PET Imaging", The Journal Nuclear Medicine, Mar. 2013, vol. 54, No. 3, pp. 455-4633.

\* cited by examiner

| Population | Treatment | | LsMean Diff. (SE) JNJ - Placebo | 80% CI JNJ - Placebo | p-value |
|---|---|---|---|---|---|
| Enriched | JNJ-67953964 10mg | | -0.70 (0.865) | [-1.81, 0.41] | 0.4188 |
| Full | JNJ-67953964 10mg | | -0.85 (0.735) | [-1.79, 0.10] | 0.2503 |
| | | ←Favours Active ─┼─ Favours Placebo→<br>-4 -3 -2 -1 0 1 2 3 4 | | | |

*FIG. 18*

FORMS OF ATICAPRANT

CROSS REFERENCE TO RELATED APPLICATIONS

This application is a continuation of U.S. patent application Ser. No. 18/178,961, filed Mar. 6, 2023, which claims the benefit of U.S. Provisional Patent Application No. 63/317,475 filed on Mar. 7, 2022, the disclosures of which are incorporated by reference herein.

TECHNICAL FIELD

The present disclosure relates to polymorphs of aticaprant and methods of using these polymorphs.

BACKGROUND

Kappa opioid receptors (KOR) and their native ligand dynorphin are localized in areas of the brain that effect reward and stress and may play a key role in mood, stress, and addictive disorders. Chronic stress, substance abuse, and acute withdrawal lead to increased dynorphin expression, activating KORs and subsequent downstream signaling pathways to inhibit mesolimbic dopamine surge, contributing to negative affective states. The behavioral pharmacology of KOR antagonism has been tested in animal models of anhedonia, depression, and anxiety and found to have meaningful effects that may translate to therapeutic benefit in humans. KOR antagonists may be effective for the treatment of patients with mood disorders, perhaps by modulating the negative affective state associated with stress response.

Anhedonia is one of the core symptoms of depression. At least mild symptoms of anhedonia are present in about 90% of patients suffering from major depressive disorder (MDD). Only about 50% of patients with MDD show a meaningful response (>50% improvement to a first line antidepressant treatment), leaving many patients with substantial persistent impairment. Therapeutic strategies such as switching antidepressants and using adjuvant drug treatments can improve response, however almost 40% of patients remain symptomatic and fail to achieve full remission.

What is needed are new compounds and treatments for patients having depression, and optionally anhedonia.

SUMMARY

In some aspects, the disclosure provides crystalline Form I of aticaprant.

In other aspects, the disclosure provides crystalline Form II of aticaprant.

In further aspects, the disclosure provides crystalline Form III of aticaprant.

In yet other aspects, the disclosure provides an amorphous form of aticaprant.

In still further aspects, the disclosure provides pharmaceutical compositions comprising a crystalline form of aticaprant as described herein or the amorphous form of aticaprant. The crystalline form of aticaprant may be Form I, Form II, or Form III.

In other aspects, the disclosure provides methods of treating major depressive disorder in a human patient, comprising administering to the human patient in need thereof an effective amount of a crystalline form of aticaprant as described herein or the amorphous form of aticaprant. The crystalline form of aticaprant may be Form I, Form II, or Form III.

In further aspects, the disclosure provides a crystalline form of aticaprant as described herein for use in the treatment of major depressive disorder in a human patient. The crystalline form of aticaprant may be Form I, Form II, or Form III.

In still other aspects, the disclosure provides an amorphous form of aticaprant for use in the treatment of major depressive disorder in a human patient.

In yet further aspects, the disclosure provides uses of the crystalline form of aticaprant as described herein or the amorphous form of aticaprant in the manufacture of a medicament for the treatment of major depressive disorder in a human patient. The crystalline form of aticaprant may be Form I, Form II, or Form III.

In other aspects, the disclosure provides packages or pharmaceutical products comprising (i) a crystalline form of aticaprant as described herein, the amorphous form of aticaprant, or a combination thereof, and (ii) instructions for treating major depressive disorder in a human patient. The crystalline form of aticaprant may be Form I, Form II, or Form III.

BRIEF DESCRIPTION OF THE DRAWINGS

FIG. 18 is a plot showing SHAPS total score changes at treatment week 6 for enriched and full population: MMRM (Mixed-effects Model for Repeated Measures) Results—estimated LSMeans and comparison versus placebo

FIG. 20-B is an excerpt from FIG. 20-A for treatment weeks 0-6.

FIG. 30-B is a line graph showing MADRS change from baseline for patients with low anhedonia, i.e., SHAPS<38.

DETAILED DESCRIPTION OF ILLUSTRATIVE EMBODIMENTS

Figure 1:
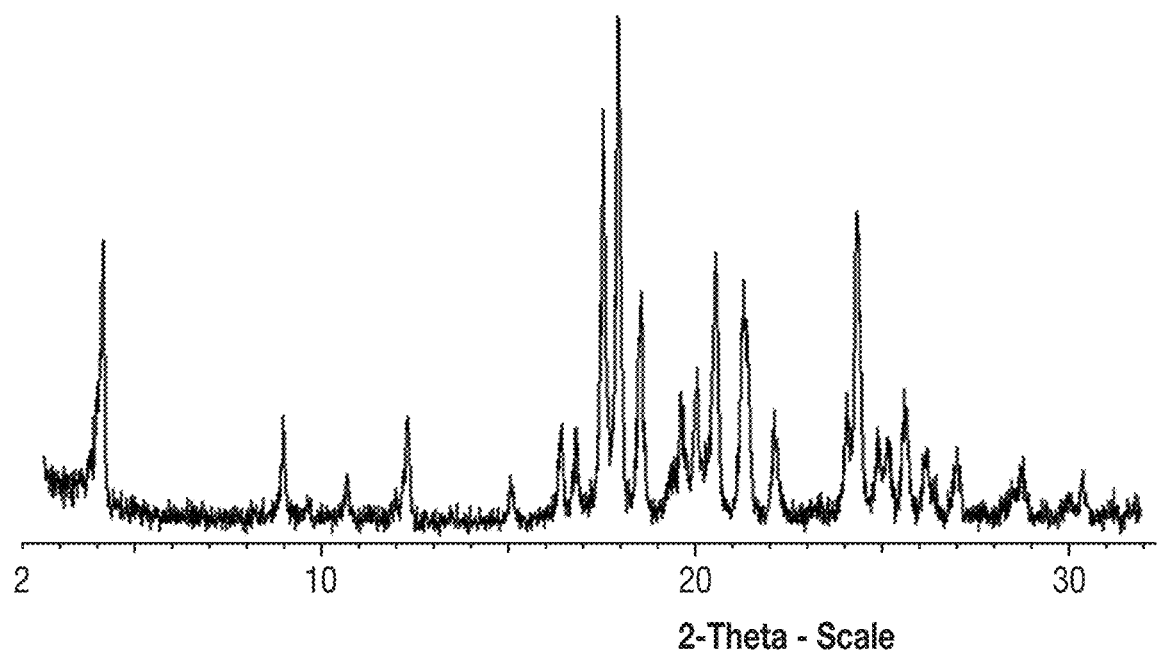
FIG. 1 is the x-ray powder diffraction (XRPD) pattern of aticaprant Form III (transmission mode).

All individual features (e.g., particular embodiments or specific preferred features) mentioned herein may be taken in isolation or in combination with any other feature (including particular embodiment or preferred feature) mentioned herein; hence, preferred features may be taken in conjunction with other preferred features, or independently of them (and likewise with particular embodiments).

The disclosure provides novel crystalline and amorphous forms of aticaprant.

The crystalline forms, i.e., Forms I, II, and III, are anhydrous and stable in the solid form. In some embodiments, crystalline Form I is anhydrous. In other embodiments, crystalline Form II is anhydrous. In further embodiments, crystalline Form III is anhydrous.

The term "crystalline" refers to a solid form of a chemical moiety that contains a highly ordered intermolecular structure.

The term "polymorph" refers to a crystalline form of a molecule having one specific crystal structure. A crystalline compound may have one crystal form or may have two or more crystal forms, i.e., polymorphs. As is understood to those skilled in the art, polymorphs of a chemical compound may distinguished from each other by compared physico-chemical properties such as solubility, dissolution rate, stability, bioavailability, among others. Polymorphs also may have different spectra selected from, without limitation, x-ray powder diffraction (XRPD), single crystal x-ray diffraction, thermogravimetric analysis (TGA), infrared spectroscopy, Raman spectroscopy, solid state nuclear magnetic resonance (NMR), differential scanning calorimetry (DSC), polarized light microscopy (PLM), hot stage microscopy, or dynamic solvent sorption.

The term "amorphous" refers to a solid form of a chemical moiety that is present in a non-crystalline state. An amorphous solid is a crystal having no characteristic shape or form. That is, amorphous forms lacks long-range structural order. Characterization of amorphous form may be performed by those skilled in the art including, without limitation, XRPD, TGA, infrared spectroscopy, Raman spectroscopy, solid state NMR, DSC, scanning electron microscopy, dynamic solvent sorption, laser diffraction, dissolution, MET analysis, densitometry, viscometry, high pressure liquid chromatography (HPLC), inverse gas chromatography, or combinations thereof. In some aspects, an amorphous sample comprises no other forms, i.e., the sample is 100% w/w amorphous. An amorphous sample may also contain solids that are crystalline. In certain aspects, an amorphous form may contain solids such that the sample is at least about 99% w/w amorphous, at least about 95% w/w amorphous, at least about 90% w/w amorphous, at least about 85% w/w amorphous, at least about 80% w/w amorphous, or the like.

The term "crystalline" refers to solid state form of a chemical moiety wherein the atoms, molecules, or ions are assembled in a highly ordered structure that extends in all directions. Thus, "crystalline" includes all crystalline forms of Compound I, including salts thereof. Characterization of crystalline forms may be performed by those skilled in the art including, without limitation, XRPD or DSC. Typically, the XRPD pattern contains sharp intensity peaks. This contrasts to the XRPD pattern of an amorphous form that often contains a broad, peak, without no identifying peaks. A crystalline form may be completely crystalline or partially crystalline. In some aspects, a crystalline sample may be 100% w/w crystalline. A crystalline sample may also contain solids that are amorphous. In certain aspects, a crystalline form may contain solids such that the sample is at least about 99% w/w crystalline, at least about 95% w/w amorphous, at least about 90% w/w crystalline, at least about 85% w/w crystalline, at least about 80% w/w crystalline, or the like.

The term "anhydrous" or "anhydrate" as used herein refers to a crystalline or amorphous form as described herein that substantially lacks water. In some aspects, an anhydrous form contains less than about 1% w/w of water. In other aspects, an anhydrous form contains less than about 0.9%, about 0.8%, about 0.7%, about 0.6%, about 0.5%, about 0.4%, about 0.3%, about 0.2%, about 0.1% w/w of water.

As provided herein, all temperature values may vary. Such variations may depend on instrument type, instrument parameters, laboratory techniques, and/or laboratory conditions. Unless otherwise defined, a recited temperature may vary. In some aspects, the temperatures noted herein vary by about 0.1°, about 0.5°, about 1°, about 2°, about 3°, about 4°, or about 5°.

Similarly, 2θ values obtained from the XRPD patterns also may vary. Such variations may depend on instrument type, instrument parameters, laboratory techniques, sample (including particle size, impurities, etc.), and/or laboratory conditions. Unless otherwise defined, the XRPD patterns and/or the 2θ peak values may vary. In certain aspects, the 2θ peak values vary (higher or lower) by about 0.05°, about 0.1°, about 0.15°, or about 0.2°. In other aspects, one or more of the 2θ peak values are higher by about 0.05°, about 0.1°, about 0.15°, or about 0.2°. In further aspects, one or more of the 2θ peak values are lower by about 0.05°, about 0.1°, about 0.15°, or about 0.2°.

As used herein, the term "corresponds to" may be used in reference to certain spectra. Thus, "corresponds to" includes a spectrum that is identical or substantially similar to another spectrum. One skilled in the art would be able to compare such spectra and determine if a spectrum corresponds to another. Thus, the term "corresponds to" is used herein to compare XRPD patterns, DSC thermograms, among others. In some aspects, one XRPD pattern corresponds to another XRPD pattern when their 2θ values are within the margin of error as described above. In other aspects, one XRPD pattern corresponds to another XRPD pattern when the peaks have the same 2θ peak value, but one or more peaks have a different height (intensity). In further aspects, one XRPD pattern corresponds to another XRPD pattern when the peaks have the same 2θ peak value, but one or more peaks have a different peak area. In yet other aspects, one XRPD pattern corresponds to another XRPD pattern when the peaks have the same 2θ peak value, but one or more peak is obscured. Such obscured peaks may be due to impurities, excipients, or the like. Such obscured peaks typically do not prevent characterization of the crystalline form.

The disclosure also provides crystalline Form I of aticaprant. Crystalline Form I of aticaprant may be characterized by a number of techniques including, without limitation, x-ray diffraction and differential scanning calorimetry. In some embodiments, crystalline Form I of aticaprant is characterized by x-ray diffraction. Crystalline Form I of aticaprant is characterized by four or more x-ray diffraction pattern peaks at 2θ (±0.2) of 4.6°, 17.3°, 17.4°, 18.0°, and 24.0°. In some embodiments, crystalline Form I of aticaprant is characterized by x-ray diffraction pattern peaks at 2θ (±0.2) of 4.6°, 17.3°, 17.4°, 18.0°, and 24.0°. In further embodiments, crystalline Form I of aticaprant is characterized by four or more x-ray diffraction pattern peaks at 2θ (±0.2) of 4.6°, 13.9°, 17.3°, 17.4°, 18.0°, and 24.0°. In other embodiments, crystalline Form I of aticaprant is characterized by four or more x-ray diffraction pattern peaks at 2θ (±0.2) of 4.6°, 17.3°, 17.4°, 18.0°, and 24.0° and one or more additional peaks at 2θ (±0.2) of 3.8°, 7.7°, 10.1°, 19.7°, 21.8°, 22.4°, 23.1°, and 25.3°. In further embodiments, crystalline Form I of aticaprant is characterized by four or more x-ray diffraction pattern peaks at 2θ (±0.2) of 4.6°, 17.3°, 17.4°, 18.0°, and 24.0° and one or more additional peaks at 2θ (±0.2) of 3.8°, 6.9°, 7.7°, 10.1°, 11.6°, 14.1°, 14.7°, 15.5°, 18.8°, 19.4°, 19.7°, 20.5°, 21.8°, 22.4°, 23.1°, 24.7°, 25.3°, 28.2°, and 29.5°. In yet other embodiments, crystalline Form I of aticaprant is characterized by four or more x-ray diffraction pattern peaks at 2θ (±0.2) of 4.6°, 17.3°, 17.4°, 18.0°, and 24.0° and one or more additional peaks at 2θ (±0.2) of 3.8°, 6.9°, 7.7°, 10.1°, 11.6°, 12.5°, 14.1°, 14.7°, 15.5°, 18.8°, 19.4°, 19.7°, 20.5°, 21.8°, 22.4°, 23.1°, 24.7°, 26.6°, 25.3°, 27.0°, 28.2°, 28.9°, 29.5°, and 30.3°. In yet other embodiments, crystalline Form I of aticaprant is characterized by four or more x-ray diffraction pattern peaks at 2θ (±0.2) of 4.6°, 17.3°, 17.4°, 18.0°, and 24.0° and one or more additional peaks as shown in Table 1.

TABLE 1

| Position (2θ) |
| --- |
| 3.8 |
| 6.5 |
| 6.9 |
| 7.7 |
| 10.1 |
| 11.6 |
| 12.5 |
| 13.8 |
| 14.1 |
| 14.7 |
| 15.2 |
| 15.5 |
| 18.2 |
| 18.5 |
| 18.8 |
| 19.1 |
| 19.4 |
| 19.7 |
| 20.2 |
| 20.5 |
| 20.9 |
| 21.6 |
| 21.8 |
| 22.4 |
| 22.8 |
| 22.9 |
| 23.1 |
| 24.4 |
| 24.7 |
| 25.3 |
| 26.5 |
| 26.6 |
| 27.0 |
| 28.2 |
| 28.9 |
| 29.5 |

In still further embodiments, crystalline Form I of aticaprant is characterized by the x-ray diffraction pattern peaks in Table 2.

TABLE 2

| Position (2θ) |
| --- |
| 3.8 |
| 4.6 |
| 6.9 |
| 7.7 |
| 10.1 |
| 11.6 |
| 12.5 |
| 14.1 |
| 14.7 |
| 15.5 |
| 17.3 |
| 17.4 |
| 18.0 |
| 18.8 |
| 19.4 |
| 19.7 |

TABLE 2-continued

| Position (2θ) |
|---|
| 20.5 |
| 21.8 |
| 22.4 |
| 23.1 |
| 24.0 |
| 24.7 |
| 25.3 |
| 26.6 |
| 27.0 |
| 28.2 |
| 28.9 |
| 29.5 |
| 30.3 |

In other embodiments, crystalline Form I of aticaprant is characterized by the x-ray diffraction pattern peaks in Table 3.

TABLE 3

| Position (2θ) |
|---|
| 3.8 |
| 4.6 |
| 6.5 |
| 6.9 |
| 7.7 |
| 10.1 |
| 11.6 |
| 12.5 |
| 13.8 |
| 14.1 |
| 14.7 |
| 15.2 |
| 15.5 |
| 17.3 |
| 17.4 |
| 18.0 |
| 18.2 |
| 18.5 |
| 18.8 |
| 19.1 |
| 19.4 |
| 19.7 |
| 20.2 |
| 20.5 |
| 20.9 |
| 21.6 |
| 21.8 |
| 22.4 |
| 22.8 |
| 22.9 |
| 23.1 |
| 24.0 |
| 24.4 |
| 24.7 |
| 25.3 |
| 26.5 |
| 26.6 |
| 27.0 |
| 28.2 |
| 28.9 |
| 29.5 |
| 30.3 |

Figure 6:
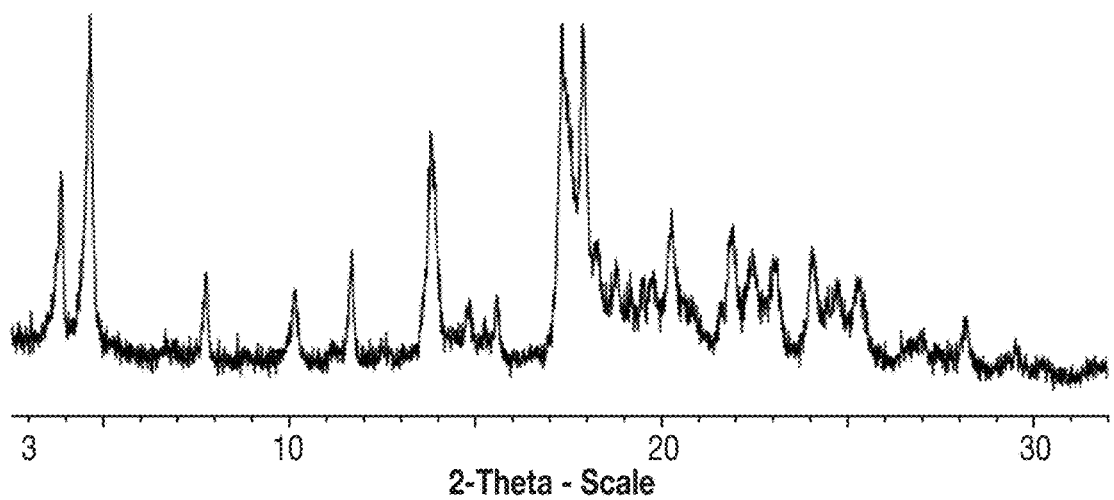
FIG. 6 is the XRPD pattern of crystalline Form I of aticaprant.

In further embodiments, crystalline Form I of aticaprant is characterized by an x-ray powder diffraction pattern that corresponds to FIG. 6.

Crystalline Form I of aticaprant may also be characterized by differential scanning calorimetry. In some embodiments, crystalline Form I of aticaprant is characterized by a differential scanning calorimetry thermogram comprising a $T_{onset}$ at about 92.9° C. In further embodiments, crystalline Form I of aticaprant is characterized by a differential scanning calorimetry thermogram comprising a peak temperature ($T_m$) at about 101.7° C. In other embodiments, crystalline Form I of aticaprant is characterized by a differential scanning calorimetry thermogram that corresponds to FIG. 7.

The disclosure also provides crystalline Form II of aticaprant. Crystalline Form II of aticaprant may be characterized by a number of techniques including, without limitation, x-ray diffraction and differential scanning calorimetry. In some embodiments, crystalline Form II of aticaprant is characterized by x-ray diffraction. In other embodiments, crystalline Form II of aticaprant is characterized by four or more x-ray diffraction pattern peaks at 2θ (±0.2) of 3.1°, 19.0°, 24.0°, 24.3°, or 26.2. In further embodiments, crystalline Form II of aticaprant is characterized by four or more x-ray diffraction pattern peaks at 2θ (±0.2) of 3.1°, 19.0°, 24.0°, 24.3°, or 26.2° and one or more additional peaks at 2θ (±0.2) of 12.9°, 14.6°, 20.8°, 22.7°, and 23.5°. In yet other embodiments, crystalline Form II of aticaprant is characterized by four or more x-ray diffraction pattern peaks at 2θ (±0.2) of 3.1°, 19.0°, 24.0°, 24.3°, or 26.2 and one or more additional peaks at 2θ (±0.2) of 11.9°, 12.9°, 14.6°, 17.4°, 20.8°, 22.7°, 23.5°, 25.5°, and 28.4°. In still further embodiments, crystalline Form II of aticaprant is characterized by four or more x-ray diffraction pattern peaks at 2θ (±0.2) of 3.1°, 19.0°, 24.0°, 24.3°, or 26.2 and one or more additional peaks at 2θ (±0.2) of 6.2°, 9.3°, 11.9°, 12.9°, 14.6°, 16.7°, 17.4°, 20.8°, 22.7°, 23.5°, 25.5°, 27.6°, 28.4°, and 29.5°. In other embodiments, crystalline Form II of aticaprant is characterized by four or more x-ray diffraction pattern peaks at 2θ (±0.2) of 3.1°, 19.0°, 24.0°, 24.3°, or 26.2 and one or more additional peaks of Table 4.

TABLE 4

| Peak (2θ) |
|---|
| 3.1 |
| 6.2 |
| 9.3 |
| 11.9 |
| 12.1 |
| 12.4 |
| 12.9 |
| 13.4 |
| 14.6 |
| 15.2 |
| 15.5 |
| 16.7 |
| 17.4 |
| 18.0 |
| 18.2 |
| 19.0 |
| 19.7 |
| 20.4 |
| 20.8 |
| 21.4 |
| 21.6 |
| 22.2 |
| 22.7 |
| 23.1 |
| 23.5 |
| 24.0 |
| 24.3 |
| 24.8 |
| 25.5 |
| 26.2 |
| 26.9 |
| 27.6 |
| 28.4 |
| 28.8 |
| 29.5 |
| 30.1 |
| 30.7 |

In further embodiments, crystalline Form II of aticaprant is characterized by the x-ray diffraction pattern peaks in Table 5.

TABLE 5

| Peak (2θ) |
|---|
| 3.1 |
| 6.2 |
| 9.3 |
| 11.9 |
| 12.9 |
| 14.6 |
| 16.7 |
| 17.4 |
| 19.0 |
| 20.8 |
| 22.7 |
| 23.5 |
| 24.0 |
| 24.3 |
| 25.5 |
| 26.2 |
| 27.7 |
| 28.4 |
| 29.5 |

In still other embodiments, crystalline Form II of aticaprant is characterized by the x-ray diffraction pattern peaks in Table 6.

TABLE 6

| Peak (2θ) |
|---|
| 3.1 |
| 6.2 |
| 9.3 |
| 11.9 |
| 12.1 |
| 12.4 |
| 12.9 |
| 13.4 |
| 14.6 |
| 15.2 |
| 15.5 |
| 16.7 |
| 17.4 |
| 18.0 |
| 18.2 |
| 19.0 |
| 19.7 |
| 20.4 |
| 20.8 |
| 21.4 |
| 21.6 |
| 22.2 |
| 22.7 |
| 23.1 |
| 23.5 |
| 24.0 |
| 24.3 |
| 24.8 |
| 25.5 |
| 26.2 |
| 27.0 |
| 27.7 |
| 28.4 |
| 28.8 |
| 29.5 |
| 30.1 |
| 30.7 |

Figure 8:
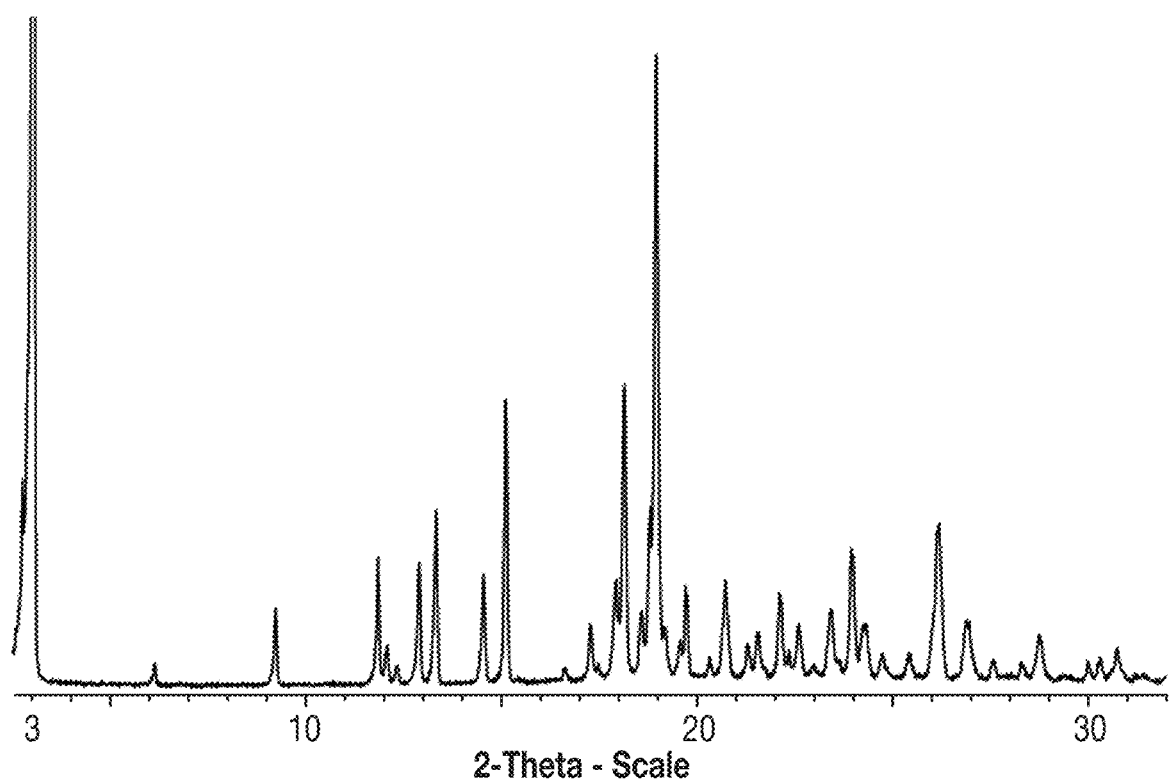
FIG. 8 is the XRPD pattern of crystalline Form II of aticaprant (1 g scale).

In yet further embodiments, crystalline Form II of aticaprant is characterized by an x-ray powder diffraction pattern that corresponds to FIG. 8.

Crystalline Form II of aticaprant may also be characterized by differential scanning calorimetry. In some embodiments, crystalline Form II of aticaprant is characterized by a differential scanning calorimetry thermogram comprising one or both endotherms at about 74.7° C. and about 96.2° C. In other aspects, crystalline Form II of aticaprant is characterized by a differential scanning calorimetry thermogram comprising a peak temperature ($T_m$) at 102.4° C. In further embodiments, crystalline Form II of aticaprant is characterized by a differential scanning calorimetry thermogram that corresponds to FIG. 9.

The disclosure further provides crystalline Form III of aticaprant. Crystalline Form III of aticaprant may be characterized by a number of techniques including, without limitation, x-ray diffraction and differential scanning calorimetry. In some embodiments, crystalline Form III of aticaprant is characterized by x-ray diffraction. In other embodiments, crystalline Form III of aticaprant is characterized by four or more x-ray diffraction pattern peaks at 2θ (±0.2) of 4.1°, 9.0°, 17.6°, 18.0°, or 21.4°. In further embodiments, crystalline Form III of aticaprant is characterized by four or more x-ray diffraction pattern peaks at 2θ (±0.2) of 4.1°, 9.0°, 17.6°, 18.0°, or 21.4° and one or more additional peaks at 16.4°, 20.1°, 20.3°, 24.1°, and 25.7°. In yet other embodiments, crystalline Form III of aticaprant is characterized by four or more x-ray diffraction pattern peaks at 2θ (±0.2) of 4.1°, 9.0°, 17.6°, 18.0°, or 21.4° and one or more additional peaks at 15.1°, 16.4°, 20.0°, 20.1°, 20.3°, 24.1°, 25.0°, 25.7°, 26.2°, and 28.8°. In still further embodiments, crystalline Form III of aticaprant is characterized by four or more x-ray diffraction pattern peaks at 2θ (±0.2) of 4.1°, 9.0°, 17.6°, 18.0°, or 21.4° and one or more additional peaks at 8.2°, 9.7°, 12.0°, 13.5°, 15.1°, 16.4°, 19.4°, 28.4°, 20.0°, 20.1°, 20.3°, 24.1°, 25.0°, 25.7°, 26.2°, 28.8°, and 30.0°. In other embodiments, crystalline Form III of aticaprant is characterized by four or more x-ray diffraction pattern peaks at 2θ (±0.2) of 3.1°, 19.0°, 24.0°, 24.3°, or 26.2 and one or more additional peaks of Table 7.

TABLE 7

| Position (2θ) |
|---|
| 4.1 |
| 8.2 |
| 9.0 |
| 9.7 |
| 10.7 |
| 12.0 |
| 12.3 |
| 13.5 |
| 15.1 |
| 16.4 |
| 16.8 |
| 17.6 |
| 18.0 |
| 18.6 |
| 19.4 |
| 19.7 |
| 20.1 |
| 20.3 |
| 20.6 |
| 21.4 |
| 22.2 |
| 24.1 |
| 24.4 |
| 25.0 |
| 25.2 |
| 25.7 |
| 26.23 |
| 26.4 |
| 27.1 |
| 28.4 |
| 28.6 |
| 28.8 |

TABLE 7-continued

| Position (2θ) |
| --- |
| 20.0 |
| 30.2 |
| 30.5 |
| 31.2 |
| 31.8 |
| 32.2 |
| 32.5 |
| 33.0 |
| 33.2 |
| 33.6 |
| 33.9 |
| 34.4 |
| 35.4 |
| 36.0 |
| 36.4 |
| 37.0 |
| 38.2 |
| 38.5 |
| 39.5 |

In still other embodiments, crystalline Form III of aticaprant is characterized the x-ray diffraction pattern peaks in Table 8.

| Position (2θ) |
| --- |
| 4.1 |
| 8.2 |
| 9.0 |
| 9.7 |
| 12.0 |
| 13.5 |
| 15.1 |
| 16.4 |
| 17.6 |
| 18.0 |
| 19.4 |
| 19.7 |
| 20.1 |
| 20.3 |
| 21.4 |
| 24.1 |
| 25.0 |
| 25.7 |
| 26.3 |
| 28.4 |
| 28.8 |
| 30.0 |

In still other embodiments, crystalline Form III of aticaprant is characterized the x-ray diffraction pattern peaks in Table 9.

TABLE 9

| Position (2θ) |
| --- |
| 4.1 |
| 8.2 |
| 9.0 |
| 9.7 |
| 10.7 |
| 12.0 |
| 12.3 |
| 13.5 |
| 15.1 |
| 16.4 |
| 16.8 |
| 17.6 |
| 18.0 |
| 18.6 |
| 19.4 |
| 19.7 |

TABLE 9-continued

| Position (2θ) |
| --- |
| 20.1 |
| 20.3 |
| 20.6 |
| 21.4 |
| 22.2 |
| 24.1 |
| 24.4 |
| 25.0 |
| 25.2 |
| 25.7 |
| 26.3 |
| 26.4 |
| 27.1 |
| 28.4 |
| 28.6 |
| 28.8 |
| 30.0 |
| 30.2 |
| 30.5 |
| 31.2 |
| 31.8 |
| 32.2 |
| 32.5 |
| 33.0 |
| 33.2 |
| 33.6 |
| 33.9 |
| 34.4 |
| 35.4 |
| 36.0 |
| 36.4 |
| 37.0 |
| 38.2 |
| 38.5 |
| 39.5 |

In further embodiments, crystalline Form III of aticaprant is characterized by an x-ray powder diffraction pattern that corresponds to FIG. 1.

Crystalline Form III of aticaprant may also be characterized by differential scanning calorimetry. In some embodiments, the differential scanning calorimetry thermogram comprises a peak temperature ($T_m$) at about 121° C. In other embodiments, crystalline Form III of aticaprant is characterized by a differential scanning calorimetry thermogram that corresponds to FIG. 4.

Figure 12:
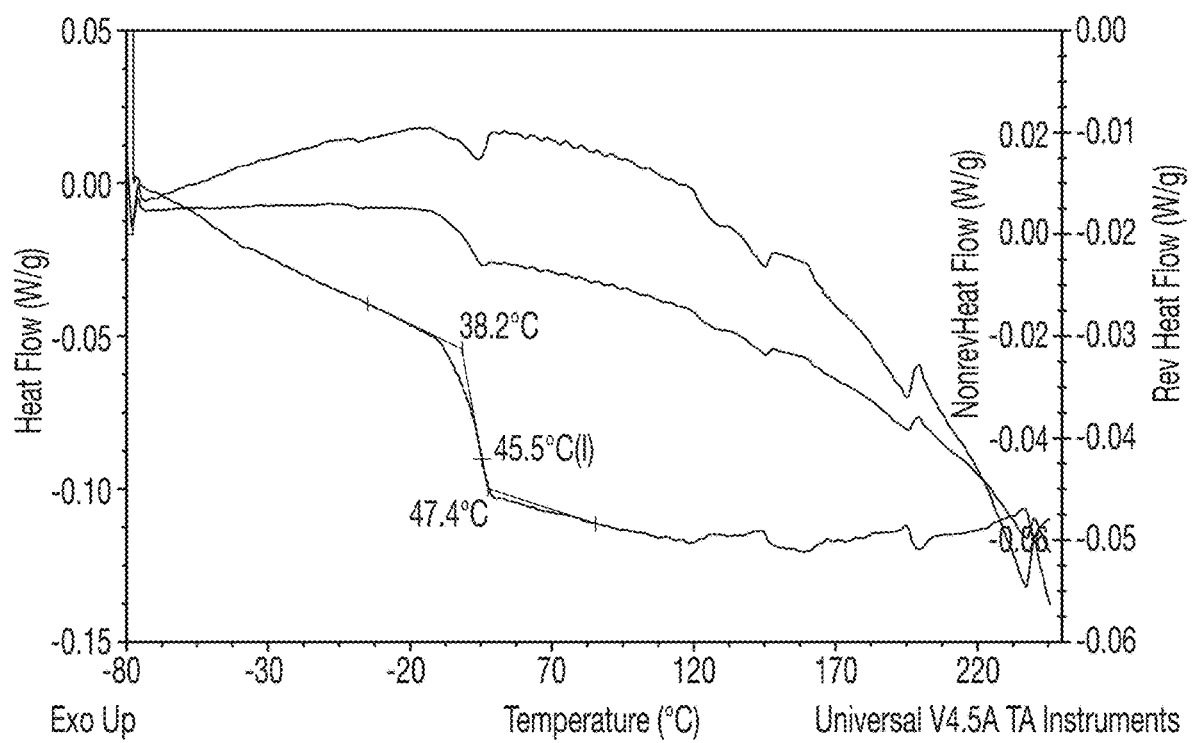
FIG. 12 is the mDSC thermogram of crystalline Form III of aticaprant.

The disclosure also provides an amorphous form of aticaprant. In certain embodiments, the amorphous form is characterized by a differential scanning calorimetry thermogram comprising a glass transition temperature ($T_g$) of about 45.5° C. In other embodiments, the amorphous form of aticaprant is characterized by a differential scanning calorimetry thermogram that corresponds to FIG. 3. In yet other embodiments, the amorphous form of aticaprant is characterized by a differential scanning calorimetry thermogram comprising a $T_{onset}$ of about 43.8° C. In further embodiments, the amorphous form of aticaprant is characterized by an mDSC thermogram that corresponds to FIG. 12.

Treatment Methods

In one aspect of the present invention, methods are provided for treating patients having a more severe type of depression, i.e., major depressive disorder. In some embodiments, the patient is experiencing moderate to severe anhedonia. Because MDD alone is difficult to treat, treatment patients having anhedonia are even more problematic since their ability to gauge pleasure is impaired. Thus, such patients often receive inadequate treatment due to ineffective medications, repeated and unnecessary medical appointments, lack of patient compliance, overall patient frustration, among others. Further, antidepressants are known to have a variety of side effects such as weight gain, metabolic side effects, extrapyramidal symptoms, akathisia, cognitive impairment, among others. Thus, patients may choose to refrain from or stop taking antidepressants to avoid or prevent any side-effects.

The methods described herein are effective in managing the patient's depression and anhedonia using crystalline Form I of aticaprant, crystalline Form II of aticaprant, crystalline Form III of aticaprant, or amorphous aticaprant. Desirably, the methods successfully permit the patient to manage their depression while simultaneously reducing anhedonia. In particular embodiments, the patients treated according to the described methods have moderate to severe anhedonia. The term "anhedonia" as used herein refers to the lack of or decreased ability to experience pleasure in daily activities. The term anhedonia includes loss of pleasure in sensory experiences (i.e., touch, taste, smell), as well as social interactions. In some embodiments, anhedonia and depressed mood are diagnostic criteria for a major depressive episode as part of MDD. Anhedonia also describes deficits in one or more components of reward-related behavior, also known as the pleasure cycle, such as wanting, liking, and learning. The pleasure cycle can be divided into three phases: the appetitive phase (dominated by wanting), the consummatory phase (dominated by liking), and the satiety phase (dominated by learning). The appetitive phase is characterized by the initial energy expenditure to attain a reward; the consummatory phase is enjoyment of the reward; and the satiety phase is characterized by learning and feedback integration.

To assess a potential effect on anhedonia, an anhedonia scale may be used. For example, the Snaith-Hamilton Pleasure Scale (SHAPS) analysis is a validated scale for the measurement of anhedonia. The SHAPS is a subject completed scale in which subjects score whether or not they experience pleasure in performing a list of activities or experiences. The SHAPS is a self-reported 14-item instrument, developed for the assessment of hedonic capacity. Subjects score whether they experience pleasure in performing a list of activities or experiences. Subjects can rate the answers as 1~4 where 1 indicates "Definitely agree", 2 indicates "Agree", 3 indicates "Disagree" and 4 indicates "Definitely disagree". The subject's item responses are summed to provide a total score ranging from 14 to 56. A higher total SHAPS score indicates higher levels of current anhedonia. Physician/clinical judgment can be used to assess anhedonia separately or in conjunction with an anhedonia scale.

In some embodiments, the patient has moderate anhedonia. In other embodiments, the patient has severe anhedonia. An assessment of moderate or severe anhedonia is typically determined physician/clinical judgment and/or by one or more tests that provide insight into whether a patient has anhedonia. For example, the severity of the anhedonia may be determined using the SHAPS method. In some embodiments, a patient with moderate or severe anhedonia is considered to have a high level of anhedonia. For example, a patient with a SHAPS score of 38 or greater is considered to have moderate to severe anhedonia that can be considered a high level of anhedonia. In some embodiments, a high level of anhedonia is reflected by a SHAPS score of at least about 40, about 42, about 44, about 46, about 48, about 50, about 52, about 54, about 56, about 58, or higher. A patient with mild or no anhedonia would be considered to have a low level of anhedonia that is assessed by physician/clinical judgment and/or one or more tests. For example, a patient with a SHAPS score of less than 38 is considered to have low anhedonia. In certain embodiments, a patient with mild anhedonia may have a SHAPS score of 20 to less than 38, for example, a SHAPS score of 20 to about 36, about 22 to about 36, about 24 to about 36, about 26 to about 36, about 26 to about 34, about 26 to about 32, about 26 to about 30, about 26 to about 28, about 28 to about 36, about 28 to about 36, about 30, to about 36, about 32 to about 36, about 34 to about 36, about 20 to about 34, about 22 to about 34, about 24 to about 34, about 26 to about 32, about 26 to about 30, about 26 to about 28, about 28 to about 36, about 28 to about 34, about 28 to about 32, about 28 to about 30, about 30 to about 36, about 30 to about 34, about 30 to about 32, about 32 to about 36, about 32 to about 34, or about 34 to about 36. Typically, a SHAPS score of less than 20 can be considered to correspond to normal hedonic functioning, and for purposes of this disclosure, would fall into the low category of anhedonia, e.g., a SHAPS score of less than 38.

In some embodiments, the patient's anhedonia is reduced from a high level of anhedonia to a low level of anhedonia. In yet other embodiments, the patient's anhedonia is reduced by at least about 40%, as measured by the change from baseline in total score in an anhedonia scale following treatment with crystalline Form I of aticaprant, crystalline Form II of aticaprant, crystalline Form III of aticaprant, or amorphous aticaprant. In yet other embodiments, the patient's anhedonia is reduced by at least about 40%, about 50%, about 60%, about 70%, about 80%, about 90%, or about 95%, as measured by the change from baseline in total score in an anhedonia scale following treatment with crystalline Form I of aticaprant, crystalline Form II of aticaprant, crystalline Form III of aticaprant, or amorphous aticaprant. In still further embodiments, In yet other embodiments, the patient's anhedonia is reduced by about 40 to about 90%, about 50 to about 90%, about 60 to about 90%, about 70 to about 90%, about 80 to about 90%, about 40 to about 80%, about 50 to about 80%, about 60 to about 80%, about 70 to about 80%, about 40 to about 70%, about 50 to about 70%, about 60 to about 70%, about 40 to about 60%, about 50 to about 60%, or about 50 to about 60%, as measured by the change from baseline in total score in an anhedonia scale following treatment with crystalline Form I of aticaprant, crystalline Form II of aticaprant, crystalline Form III of aticaprant, or amorphous aticaprant. In other embodiments, the patient's anhedonia is ameliorated, i.e., reduced by 100%, as measured by the change from baseline in total score in an anhedonia scale following treatment with crystalline Form I of aticaprant, crystalline Form II of aticaprant, crystalline Form III of aticaprant, or amorphous aticaprant.

Reduction of anhedonia after initiating treatment with crystalline Form I of aticaprant, crystalline Form II of aticaprant, crystalline Form III of aticaprant, or amorphous aticaprant may be measured relative to the anhedonia of the patient as measured before treatment with crystalline Form I of aticaprant, crystalline Form II of aticaprant, crystalline Form III of aticaprant, or amorphous aticaprant, i.e., a baseline anhedonia measurement. In doing so, the treating clinician is able to calculate the change of anhedonia from the baseline to the real time anhedonia measurement at any point after treatment with crystalline Form I of aticaprant, crystalline Form II of aticaprant, crystalline Form III of aticaprant, or amorphous aticaprant. Thus, standard methods for measuring anhedonia may be used, such as an anhedonia scale, e.g., SHAPS.

Desirably, a baseline anhedonia measurement is obtained no more than about 1 week before initiating treatment with crystalline Form I of aticaprant, crystalline Form II of aticaprant, crystalline Form III of aticaprant, or amorphous aticaprant. In some embodiments, a baseline anhedonia measurement is obtained about 7 days, about 6 days, about 5 days, about 4 days, about 3 days, about 2 days, or about 1 day before treatment with crystalline Form I of aticaprant, crystalline Form II of aticaprant, crystalline Form III of aticaprant, or amorphous aticaprant. In further embodiments, a baseline anhedonia measurement is obtained about 24 hours, about 18 hours, about 12 hours, about 8 hours, about 4 hours, about 2 hours, about 1 hours, about 30 minutes, or about 15 minutes before initiating treatment with crystalline Form I of aticaprant, crystalline Form II of aticaprant, crystalline Form III of aticaprant, or amorphous aticaprant.

The patient's change of anhedonia will depend on several factors including, without limitation, anhedonia severity, patient's sensitivity to crystalline Form I of aticaprant, crystalline Form II of aticaprant, crystalline Form III of aticaprant, or amorphous aticaprant, other pharmaceutical agents being administered, among others. In some embodiments, the patient's anhedonia is reduced after about 3 weeks of treatment with crystalline Form I of aticaprant, crystalline Form II of aticaprant, crystalline Form III of aticaprant, or amorphous aticaprant. In other embodiments, the patient's anhedonia is reduced after about 3 weeks of treatment with crystalline Form I of aticaprant, crystalline Form II of aticaprant, crystalline Form III of aticaprant, or amorphous aticaprant. In further embodiments, the patient's anhedonia is reduced after about 3 weeks to about 6 weeks, and, in certain embodiments, through week 6, of treatment with crystalline Form I of aticaprant, crystalline Form II of aticaprant, crystalline Form III of aticaprant, or amorphous aticaprant. In certain embodiments, the patient's anhedonia is reduced by at least about 40%, as measured by the change from baseline in total score in an anhedonia scale following about 6 weeks of the treatment with crystalline Form I of aticaprant, crystalline Form II of aticaprant, crystalline Form III of aticaprant, or amorphous aticaprant. In further embodiments, the anhedonia of the patient is reduced within about 3 weeks, and in some embodiments within about 3 weeks to about 6 weeks, as measured by the change from baseline in total score in an anhedonia scale and/or by physician/clinical judgement.

The methods described herein were found to not only improve the patient's depression and anhedonia symptoms, but resulted in fewer antidepressant side effects. Doing so resulted in less absentecism (i.e., more visits or interactions with physicians), greater cognitive functioning, improvements in health-related quality of life, more interest and engagement in everyday activities, improvement in family and inter-personal relationships, ability to function in the workplace, fewer hospitalizations, among others.

As used herein, unless otherwise noted, the terms "subject" and "patient" refer to a human, who has been the object of treatment, observation or experiment. Preferably, the patient has experienced and/or exhibited at least one symptom of the disease or disorder to be treated and/or prevented. In some embodiments, the patient is an adult. As used herein, the term "adult" as used herein refers to a human that is about 18 years of age or older. In certain aspects, the patient is an elderly adult, i.e., greater than or equal to 65 years of age.

As used herein, unless otherwise noted, the terms "treating", "treatment" and the like, shall include the management and care of a subject or patient (preferably mammal, more preferably human) for the purpose of combating a disease, condition, or disorder and includes the administration of a compound described herein to prevent the onset of the symptoms or complications, alleviate one or more of the symptoms or complications, or eliminate the disease, condition, or disorder.

As used herein, the term "depression" (also referred to as depressive disorder) includes major depressive disorder, persistent depressive disorder, seasonal affective disorder, postpartum depression, premenstrual dysphoric disorder, situational depression, anhedonia, melancholic, mid-life depression, late-life depression, bipolar depression, depression due to identifiable stressors, treatment resistant depression, or combinations thereof. In certain embodiments, the depression is major depressive disorder. In other embodiments, the major depressive disorder is with melancholic features or anxious distress. In further embodiments, the depression is treatment-resistant depression. In other embodiments, the depression is major depressive disorder with suicidal ideation.

As known in the art, a patient is considered to have major depressive disorder if exhibiting five or more symptoms during the same two week period that are a change from previous functioning; depressed mood and/or loss of interest/pleasure must be present; excluding symptoms clearly attributable to another medical condition. See, e.g., Table 11.

TABLE 11

1. Depressed mood: Most of the day, nearly every day; may be subjective (e.g., feels sad, empty, hopeless) or observed by others (e.g., appears tearful); in children and adolescents, can be irritable mood
2. Loss of interest/pleasure: Markedly diminished interest/pleasure in all (or almost all) activities most of the day, nearly every day; may be subjective or observed by others
3. Weight loss or gain: Significant weight loss (without dieting) or gain (change of >5% body weight in a month), or decrease or increase in appetite nearly every day; in children, may be failure to gain weight as expected
4. Insomnia or hypersomnia: Nearly every day
5. Psychomotor agitation or retardation: Nearly every day and observable by others (not merely subjectively restless or slow)
6. Fatigue: Or loss of energy, nearly every day
7. Feeling worthless or excessive/inappropriate guilt: Nearly every day; guilt may be delusional; not merely self-reproach or guilt about being sick
8. Decreased concentration: Nearly every day; may be indecisiveness; may be subjective or observed by others
9. Thoughts of death/suicide" Recurrent thoughts of death (not just fear of dying), recurrent suicidal ideation without specific plan, or suicide attempt, or a specific plan for suicide In some embodiments, to be diagnosed with MDD, the following criteria also are met:

1. Symptoms cause clinically significant distress or impairment in social, occupational, or other important areas of functioning
2. Episode not attributable to physiological effects of a substance or another medical condition
3. Episode not better explained by schizoaffective disorder, schizophrenia, schizophreniform disorder, delusional disorder, or other specified and unspecified schizophrenia spectrum and other psychotic disorders
4. No history of manic or hypomanic episode Major depressive disorder may be categorized as mild, moderate, or severe. In some embodiments, the MDD is mild. In other embodiments, the MDD is moderate. In further embodiments, the MDD is severe. As used herein, "mild MDD" applies to a patient having few, if any, symptoms in excess of those required to make the diagnosis, the intensity of the symptoms is distressing but manageable, and the symptoms result in minor impairment in social or occupational functioning. The mild MDD may be a single episode (ICD-10 F32.0) or a recurrent episode (ICD-10 F33.0). "Moderate MDD" applies to a patient having a number of symptoms, intensity of symptoms, and/or functional impairment are between those specified for "mild" and "severe." The moderate MDD may be a single episode (ICD-10 F32.1) or a recurrent episode (ICD-10 F33.1). "Severe MDD" applies to a patient where the number of symptoms is substantially in excess of that required to make the diagnosis, the intensity of symptoms is seriously distressing and unmanageable, and the symptoms markedly interfere with social and occupational functioning, and urgent symptom control is necessary. In some embodiments, the severe MDD may be a single episode (ICD-10 F32.2) or a recurrent episode (ICD-10 F33.2). In other embodiments, MDD is classified according to the DSM-5 definition of Table 12.

TABLE 12

DSM-5 Criteria for MDD

| | |
|---|---|
| 1. Depressed Mood | At least 1 |
| 2. Loss of interest/pleasure (anhedonia) | |
| 1. Weight loss or gain | At least 5 |
| 2. Sleep problems | |
| 3. Psychomotor agitation or retardation | |
| 4. Guilt or worthlessness | |
| 5. Decreased concentration | |
| 6. Suicidality | |
| 7. Fatigue | |
| 1. Symptoms cause significant distress or impairment | Must have all 4 |
| 2. Not attributable to medical condition | |
| 3. Exclude schizophrenia disorders | |
| 4. No hx of mania or hypomania | |

Several scales are known in the art that may be utilized to diagnose or monitor patients with MDD. Examples of these scales include, without limitation, the Montgomery-Åsberg Depression Rating Scale (MADRS), Clinical Global Impression-Severity (CGI-S) scale, Symptoms of Major Depressive Disorder Scale (SMDDS), Self-Assessment of Treatment Experience (SATE) scale, and Massachusetts General Hospital (MGH) Antidepressant Treatment Response Questionnaire (ATRQ), i.e., MGH-ATRQ.

In some embodiments, MADRS is utilized to diagnose and/or monitor the patient. MADRS is a 10-item rating scale that is used in antidepressant studies. It is clinician-administered and designed to be used in subjects with MDD to measure the overall severity of depressive symptoms. The MADRS scale is validated, reliable, and acceptable to regulatory health authorities as a primary scale to determine efficacy in major depression. In some embodiments, MADRS is administered using the Structured Interview Guide for the MADRS (SIGMA). The scale consists of 10 items, each of which is scored from 0 (item not present or normal) to 6 (severe or continuous presence of the symptoms), summed for a total possible score of 60. Higher scores represent a more severe condition. The MADRS evaluates apparent sadness, reported sadness, inner tension, sleep appetite, concentration, lassitude, inability to feel (interest level), pessimistic thoughts, and suicidal thoughts.

In other embodiments, CGI-S is utilized to diagnose and/or monitor the patient's depression. CGI-S is a scale that rates the severity of the subject's illness at the time of assessment, relative to the clinician's past experience with subjects who have the same diagnosis and improvement with treatment. CGI-S provides an overall clinician-determined summary measure of severity of subject's illness that considers all available information, including knowledge of subject's history, psychosocial circumstances, symptoms, behavior, and impact of symptoms on subject's ability to function. CGI-S evaluates severity of psychopathology on scale of 0 to 7. Subject is assessed on severity of mental illness at time of rating according to: 0=not assessed; 1=normal (not at all ill); 2-borderline mentally ill; 3=mildly ill; 4=moderately ill; 5=markedly ill; 6=severely ill; 7=among most extremely ill patients.

In further embodiments, SMDDS is utilized to diagnose and/or monitor the patient's depression. SMDDS is a subjective rating of the patient. The SMDDS is a 16-item PRO measure. Each item is rated by the subject according to a 5-point Likert scale. Subjects respond to each question using a rating scale between 0 ("Not at all" or "Never") to 4 ("Extremely" or "Always"). The total score ranges from 0 to 60. The SMDDS uses a 7-day recall period and verbal rating scales. Higher score indicates more severe depressive symptomatology.

In yet other embodiments, SATE is utilized to diagnose and/or monitor the patient's depression. SATE is a one to three questionnaire administered when the subject is unable to complete other evaluations, i.e., away from the clinical setting such as at home. SATE is useful to evaluate improvement or deterioration of depressive symptoms of the subjects over a short period of time. For rating overall depression, subject selected one option out of Improved, not changed or got worse; for depression improvement, subject selected one option out of slightly improved, much improved, very much improved and for depression worsen subject selected slightly worse, much worse, very much worse. See, Table 13.

TABLE 13

SATE Questionnaire

Question 1: Since starting this study medication,
overall would you say your depression is:
Improved
Got worse
Not changed
If the subject selects answer 1 (Improved), following question is asked:
Question 2: How much did your depression improve?
Slightly improved
Much improved
Very much improved
If the subject selects answer 3 (Got worse), following question is asked:
Question 3:How much did your depression worsen?
Slightly worse
Much worse
Very much worse The MGH-ATRQ is a self-rated scale used to determine treatment resistance in patient's having MDD. This questionnaire examines the antidepressant treatment history, using specific anchor points to define the adequacy of both dose and duration of each antidepressant trial, and the degree of symptomatic improvement. The MGH-ATRQ permits determining treatment resistance in depression and is known to those skilled in the art.

In certain embodiments, the patient had an inadequate response to other antidepressant therapy. "Inadequate response" as used herein refers to a patient experiencing a less than about 50% reduction in depressive symptom severity from the start of initiating treatment. Typically, the inadequate response is during a current/active episode of the depression. In some embodiments, an inadequate response refers to a patient experiencing about 26 to less than about 50% reduction in depressive symptom severity from the start of initiating treatment. In other embodiments, an inadequate response refers to a patient experiencing about 26 to about 49, about 26 to about 45, about 26 to about 40, about 26 to about 35, about 26 to about 30, about 30 to about 49, about 30 to about 45, about 30 to about 40, about 30 to about 35, about 35 to about 49, about 35 to about 45, about 35 to about 40, about 40 to about 49, or about 40 to about 45% reduction in depressive symptom severity from the start of initiating treatment. A patient's response may be measured by one or more scales described herein and/or by physician/clinical judgment. In some embodiments, an inadequate response is measured by MGH-ATRQ, MADRS, or SHAPS. In further embodiments, an inadequate response is measured by MGH-ATRQ.

To the extent a patient is said to have a partial response to treatment, this refers to some minor to moderate symptomatic improvement since the initiation of treatment, but some of the initial symptoms are still present and troubling to the patient and these persistent symptoms still affect behavior and function. For instance, the patient's motivation, productivity, and interest in his or her usual activities may still be impaired.

The term "other antidepressant therapy" as used herein refers to an antidepressant medication or non-pharmacological treatment that is used to treat patients having depression. In some aspects, the other antidepressant therapy is an antidepressant medication. In other aspects, the other antidepressant therapy is a non-pharmacological treatment. In further aspects, the other antidepressant therapy is an antidepressant medication other than aticaprant.

The antidepressant medication is any pharmaceutical agent which can be used to treat depression. Suitable examples include, without limitation, mono-amine oxidase inhibitors, tricyclics, tetracyclics, non-cyclics, triazolopyridines, selective serotonin reuptake inhibitors (SSRI), serotonin receptor antagonists, serotonin noradrenergic reuptake inhibitors (SNRI), noradrenergic and specific serotonergic agents, noradrenaline reuptake inhibitors, or antipsychotics (typical or atypical antipsychotics). Examples of mono-amine oxidase inhibitors include phenelzine, tranylcypromine, moclobemide, and the like. Examples of tricyclics include imipramine, amitriptyline, desipramine, nortriptyline, doxepin, protriptyline, trimipramine, clomipramine, amoxapine, and the like. Examples of tetracyclics includes maprotiline, and the like. Examples of non-cyclics include nomifensine, and the like. Examples of triazolopyridines include trazodone, and the like. Examples of SSRIs include fluoxetine, sertraline, paroxetine, citalopram, citalopram, escitalopram, fluvoxamine, and the like. Examples of serotonin receptor antagonists include nefazadone, and the like. Examples of SNRIs include venlafaxine, milnacipran, desvenlafaxine, duloxetine, levomilnacipran and the like. Examples of noradrenergic and specific serotonergic agents include mirtazapine, and the like. Examples of noradrenaline reuptake inhibitors include reboxetine, edivoxetine and the like. Examples of typical antipsychotics include phenothiazines (e.g., chlorpromazine, thioridazine, fluphenazine, perphenazine, trifluoperazine, levomepromazin), thioxanthenes (e.g., thiothixene, flupentixol), butyrophenones (e.g., haloperidol), dibenzoxazepines (e.g., loxapine), dihydroindolones (e.g., molindone), substituted benzamides (e.g., sulpride, amisulpride), and the like. Examples of atypical antipsychotics include paliperidone, clozapine, risperidone, olanzapine, quetiapine, zotepine, ziprasidone, iloperidone, perospirone, blonanserin, sertindole, ORG-5222, sonepiprazole, aripiprazole, nemonapride, SR-31742, CX-516, SC-111, NE-100, divalproate (mood stabilizer) and the like. In further embodiments, the antidepressant medication includes natural products such as Kava-Kava, St. John's Wort, and the like or dietary supplements such as s-adenosylmethionine, and the like. In yet other embodiments, the antidepressant medication includes neuropeptides such as thyrotropin-releasing hormone and the like or compounds targeting neuropeptide receptors such as neurokinin receptor antagonists and the like. In still further embodiments, the antidepressant medication is a hormone such as triiodothyronine, and the like. In other embodiments, the antidepressant medication is SSRI, SNRI, or a combination thereof. Preferably, the antidepressant is a SSRI that is escitalopram, sertraline, paroxetine, fluoxetine or citalopram. In other embodiments, the antidepressant medication is a SNRI that is venlafaxine, duloxetine, vortioxeine or desvenlafaxine.

The non-pharmacologic treatment for use herein may be selected by one skilled in the art. In some embodiments, the non-pharmacologic treatment is psychotherapy, transcranial magnetic stimulation, or the like.

Therapeutically effective amounts/dosage levels and dosage regimens for the other antidepressant therapy may be readily determined by one of ordinary skill in the art. For example, therapeutic dosage amounts and regimens for pharmaceutical agents approved for sale are publicly available, for example as listed on packaging labels, in standard dosage guidelines, in standard dosage references such as the Physician's Desk Reference (Medical Economics Company or online at http:///www.pdrel.com) or other sources.

In some embodiments, other antidepressant therapy may include one antidepressant medication. In other embodiments, other antidepressant therapy includes two or more antidepressant medications. In further embodiments, other antidepressant therapy includes two antidepressant medications. In yet other embodiments, other antidepressant therapy includes three antidepressant medications. The attending physician would be able to select suitable antidepressant therapies for use as described herein.

In certain embodiments, the patient was receiving treatment with other antidepressant therapy prior to receiving crystalline Form I of aticaprant, crystalline Form II of aticaprant, crystalline Form III of aticaprant, or amorphous aticaprant. In some embodiments, the patient was receiving treatment with other antidepressant therapy that comprised a SSRI, SNRI, or a combination thereof. In other embodiments, the patient stopped treatment with other antidepressant therapy before initiating treatment with crystalline Form I of aticaprant, crystalline Form II of aticaprant, crystalline Form III of aticaprant, or amorphous aticaprant.

Also encompassed by the methods described herein include adjunctive treatment with an effective amount of one or more antidepressants. As used herein, the term "adjunctive treatment" and "adjunctive therapy" shall mean treatment of a patient in need thereof by administering crystalline Form I of aticaprant, crystalline Form II of aticaprant, crystalline Form III of aticaprant, or amorphous aticaprant in combination with one or more antidepressant(s), wherein crystalline Form I of aticaprant, crystalline Form II of aticaprant, crystalline Form III of aticaprant, or amorphous aticaprant and the antidepressant(s) are administered by any suitable means, simultaneously, sequentially, separately, or in a single pharmaceutical formulation.

In some aspects, crystalline Form I of aticaprant, crystalline Form II of aticaprant, crystalline Form III of aticaprant, or amorphous aticaprant is administered adjunctively with other antidepressant(s) currently being administered to the patient, including current antidepressant(s) to which the patient had an inadequate response, i.e., the antidepressant failed to treat the patient's depression. In other embodiments, crystalline Form I of aticaprant, crystalline Form II of aticaprant, crystalline Form III of aticaprant, or amorphous aticaprant is administered adjunctively with an antidepressant(s) not previously administered to the patient, i.e., a new antidepressant. In still other embodiments, crystalline Form I of aticaprant, crystalline Form II of aticaprant, crystalline Form III of aticaprant, or amorphous aticaprant is administered in a regimen with an antidepressant(s) previously administered to the patient.

Where crystalline Form I of aticaprant, crystalline Form II of aticaprant, crystalline Form III of aticaprant, or amorphous aticaprant and other antidepressant(s) are administered in separate dosage forms, the number of dosages administered per day for each active compound may be the same or different and more typically different. The antidepressant may be dosed as prescribed by the attending physician and/or by its label and crystalline Form I of aticaprant, crystalline Form II of aticaprant, crystalline Form III of aticaprant, or amorphous aticaprant is dosed as described herein. Typically, a patient is under concurrent treatment with both an antidepressant and crystalline Form I of aticaprant, crystalline Form II of aticaprant, crystalline Form III of aticaprant, or amorphous aticaprant, where both are administered by their prescribed dosing regimens. The crystalline Form I of aticaprant, crystalline Form II of aticaprant, crystalline Form III of aticaprant, or amorphous aticaprant and antidepressant(s) may be administered according to simultaneous or alternating regimens, at the same or different times during the course of the therapy, concurrently in divided or single forms.

Crystalline Form I of aticaprant, crystalline Form II of aticaprant, crystalline Form III of aticaprant, or amorphous aticaprant and the antidepressant(s) may be administered via the same or different routes of administration. Examples of suitable methods of administration include, but are not limited to, oral, intravenous (iv), intranasal (in) intramuscular (im), subcutaneous (sc), transdermal, buccal, or rectal. In some embodiments, crystalline Form I of aticaprant, crystalline Form II of aticaprant, crystalline Form III of aticaprant, or amorphous aticaprant is administered orally.

Treatment with crystalline Form I of aticaprant, crystalline Form II of aticaprant, crystalline Form III of aticaprant, or amorphous aticaprant as described herein has several advantages over the treatments in the art. In some embodiments, the patient does not experience many of the side effects that are associated with other antidepressants, i.e., antidepressants other than crystalline Form I of aticaprant, crystalline Form II of aticaprant, crystalline Form III of aticaprant, or amorphous aticaprant. In certain aspects, the patient does not experience weight gain during the treatment with crystalline Form I of aticaprant, crystalline Form II of aticaprant, crystalline Form III of aticaprant, or amorphous aticaprant. As used herein, the term "weight gain" refers to an increase in the weight of patient, relative to the weight of the patient before taking crystalline Form I of aticaprant, crystalline Form II of aticaprant, crystalline Form III of aticaprant, or amorphous aticaprant or the weight of the patient that is assessed at the time of the initial administration of the crystalline Form I of aticaprant, crystalline Form II of aticaprant, crystalline Form III of aticaprant, or amorphous aticaprant. In certain embodiments, the patient may actually see a decrease in overall weight, relative to the weight of the patient before taking crystalline Form I of aticaprant, crystalline Form II of aticaprant, crystalline Form III of aticaprant, or amorphous aticaprant. In further embodiments, the patient's weight is stable, i.e., does not increase or decrease. In certain embodiments, the patient does not experience a clinically relevant weight gain which is characterized as a weight increase of ≥7%.

This is contrary to many other antidepressants where weight gain, including clinically relevant weight gain, is a common, but unfortunate, side-effect.

In further aspects, the patient does not experience a decrease in sexual functioning during the treatment with crystalline Form I of aticaprant, crystalline Form II of aticaprant, crystalline Form III of aticaprant, or amorphous aticaprant. As used herein, the term "decrease in sexual functioning" refers to reducing or lessening of one or more components of the human sex drive, i.e., sexual functioning. In some embodiments, the sexual functioning comprises one or more of sexual drive, sexual arousal, vaginal lubrication, erection, orgasm achievement, or orgasm satisfaction. In other embodiments, the sexual functioning comprises sexual drive. In further embodiments, the sexual functioning comprises vaginal lubrication satisfaction. In further embodiments, the sexual functioning comprises orgasm achievement. In yet other embodiments, the sexual functioning comprises orgasm satisfaction. Desirably, the patient's sexual functioning is assessed at the time of initial administration of the crystalline Form I of aticaprant, crystalline Form II of aticaprant, crystalline Form III of aticaprant, or amorphous aticaprant. Thus, the patient's sexual functioning while taking crystalline Form I of aticaprant, crystalline Form II of aticaprant, crystalline Form III of aticaprant, or amorphous aticaprant can be compared to the patient's sexual functioning before administration of crystalline Form I of aticaprant, crystalline Form II of aticaprant, crystalline Form III of aticaprant, or amorphous aticaprant. Sexual functioning may be assessed by using standard scales and techniques such as the Arizona Sexual Experience Scale (ASEX). The ASEX is used to investigate whether crystalline Form I of aticaprant, crystalline Form II of aticaprant, crystalline Form III of aticaprant, or amorphous aticaprant has a further positive or negative effect on sexual function. The ASEX is 5 item rating scale administered to patients that quantifies sexual drive, sexual arousal, vaginal lubrication or penile erection, ability to reach orgasm and satisfaction. Scores range from 5 to 30, and two different versions of the scale are available (males and females).

Other scales may be utilized to determine the effectiveness of the methods used herein to treat the patient. Examples include the Cognitive and Physical Functioning Questionnaire (CPFQ), Karolinska Sleepiness Scale (KSS), and Temporal Experience of Pleasure Scale (TEPS). The CPFQ is a brief self-report scale that provides additional information regarding the impact of adjunctive treatment on aspects of cognitive and executive function including attention, memory and mental acuity. Subjects with MDD are often reported to have difficulties with functioning in this area. The KSS is a subject-reported assessment used to rate sleepiness on a scale of 1 to 9, ranging from "extremely alert" (1) to "very sleepy, great effort to keep awake, fighting sleep" (9). The TEPS includes 18 items, 2 subscales designed to distinguish between anticipatory and consummatory pleasure.

As used herein, unless otherwise noted, the term "aticaprant" refers to 3-fluoro-4-4-2-(3,5-dimethylphenyl) pyrrolidin-1-yl-methylphenoxybenzamide, i.e., the following compound:

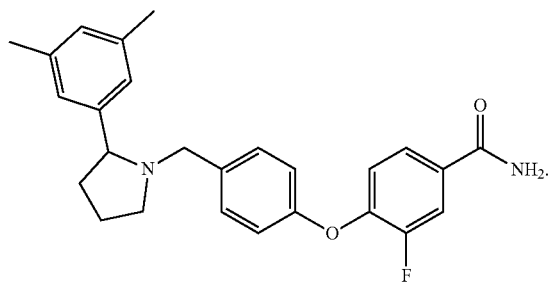 [SMILES: Cc1cc(C)cc(C2CCCN2Cc2ccc(Oc3ccc(C(N)=O)cc3F)cc2)c1]

and is also known as JNJ-67953964, CERC-501, and LY-2456302. In some embodiments, "aticaprant" refers to the (S)-enantiomer of aticaprant, i.e., the following compound:

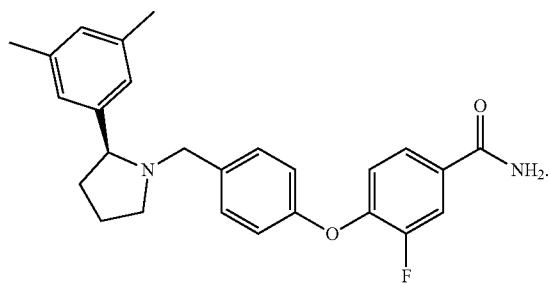 [SMILES: Cc1cc(C)cc([C@@H]2CCCN2Cc2ccc(Oc3ccc(C(N)=O)cc3F)cc2)c1]

also known as (S)-aticaprant or(S)-3-fluoro-4-4-2-(3,5-dimethylphenyl) pyrrolidin-1-yl-methylphenoxybenzamide. In other embodiments, the aticaprant used in the methods described herein is substantially free of the (R)-enantiomer, i.e., (R)-aticaprant or (R)-3-fluoro-4-4-2-(3,5-dimethylphenyl) pyrrolidin-1-yl-methylphenoxybenzamide having the following structure:

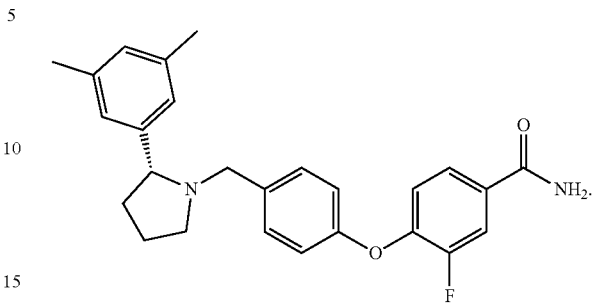

In other embodiments, the crystalline Form I of aticaprant, crystalline Form II of aticaprant, crystalline Form III of aticaprant, or amorphous aticaprant contains less than about 10% by weight, based on the weight of the crystalline Form I of aticaprant, crystalline Form II of aticaprant, crystalline Form III of aticaprant, or amorphous aticaprant, of the (R)-enantiomer of aticaprant. In further embodiments, the crystalline Form I of aticaprant, crystalline Form II of aticaprant, crystalline Form III of aticaprant, or amorphous aticaprant contains less than about 10, about 9, about 8, about 7, about 6, about 5, about 4, about 3, about 2, about 1, about 0.5, about 0.1, about 0.005, or about 0.001% by weight, based on the weight of the crystalline Form I of aticaprant, crystalline Form II of aticaprant, crystalline Form III of aticaprant, or amorphous aticaprant, of the (R)-enantiomer of aticaprant. In yet other embodiments, the crystalline Form I of aticaprant, crystalline Form II of aticaprant, crystalline Form III of aticaprant, or amorphous aticaprant contains about 0.001 to about 10% by weight, based on the weight of the crystalline Form I of aticaprant, crystalline Form II of aticaprant, crystalline Form III of aticaprant, or amorphous aticaprant, of the (R)-enantiomer of aticaprant. In still further embodiments, the crystalline Form I of aticaprant, crystalline Form II of aticaprant, crystalline Form III of aticaprant, or amorphous aticaprant contains about 0.001 to about 10%, about 0.001 to about 5%, about 0.001 to about 1%, about 0.001 to about 0.5%, about 0.001 to about 0.1%, about 0.1 to about 5%, about 0.1 to about 1%, about 0.1 to about 5%, or about 0.5 to about 5% by weight, based on the weight of the crystalline Form I of aticaprant, crystalline Form II of aticaprant, crystalline Form III of aticaprant, or amorphous aticaprant, of the (R)-enantiomer of aticaprant.

The methods described herein include administering an effective amount of crystalline Form I of aticaprant, crystalline Form II of aticaprant, crystalline Form III of aticaprant, or amorphous aticaprant to the patient. The term "effective amount" as used herein, means that amount of active compound or pharmaceutical agent that elicits the biological or medicinal response in a human that is being sought by a researcher, medical doctor or other clinician, which includes alleviation of one or more of the symptoms of the disease or disorder being treated. In some embodiments, crystalline Form I of aticaprant, crystalline Form II of aticaprant, crystalline Form III of aticaprant, or amorphous aticaprant is utilized in an effective amount as determined by the attending physician. In other embodiments, other antidepressant(s) is utilized in an effective amount either separately or in combination with crystalline Form I of aticaprant, crystalline Form II of aticaprant, crystalline Form III of aticaprant, or amorphous aticaprant.

The amount of crystalline Form I of aticaprant, crystalline Form II of aticaprant, crystalline Form III of aticaprant, or amorphous aticaprant for administration according to the methods described herein may be determined by one skill in the art and, unless otherwise noted, are set forth on a crystalline Form I of aticaprant, crystalline Form II of aticaprant, crystalline Form III of aticaprant, or amorphous aticaprant free base basis. That is, the amounts indicate that amount of the crystalline Form I of aticaprant, crystalline Form II of aticaprant, crystalline Form III of aticaprant, or amorphous aticaprant molecule administered, exclusive of, for example, solvent (such as in solvates) or counterions (such as in pharmaceutically acceptable salts). In some embodiments, the effective amount of crystalline Form I of aticaprant, crystalline Form II of aticaprant, crystalline Form III of aticaprant, or amorphous aticaprant is less than about 60 mg. In other embodiments, the effective amount of crystalline Form I of aticaprant, crystalline Form II of aticaprant, crystalline Form III of aticaprant, or amorphous aticaprant is about 0.5 mg, about 1 mg, about 2 mg, about 4 mg, about 5 mg, about 10 mg, about 15 mg, about 20 mg, 25 mg, about 30 mg, about 35 mg, about 40 mg, about 45 mg, about 50 mg, about 55 mg, or about 60 mg. In further embodiments, the effective amount of crystalline Form I of aticaprant, crystalline Form II of aticaprant, crystalline Form III of aticaprant, or amorphous aticaprant is about 1 to about 50 mg, about 5 to about 50 mg, about 10 to about 50 mg, about 20 to about 50 mg, about 30 to about 50 mg, about 40 to about 50 mg, about 1 to about 45 mg, about 2 to about 45 mg, about 5 to about 45 mg, about 10 to about 45 mg, about 20 to about 45 mg, about 30 to about 45 mg, about 30 to about 40 mg, about 30 to about 35 mg, about 1 to about 40 mg, about 5 to about 40 mg, about 10 to about 40 mg, about 20 to about 40 mg, about 30 to about 40 mg, about 1 to about 35 mg, about 2 to about 35 mg, about 5 to about 35 mg, about 10 to about 35 mg, about 20 to about 35 mg, about 25 to about 35 mg, about 30 to about 35 mg, about 1 to about 30, about 2 to about 30 mg, about 5 to about 30 mg, about 10 to about 30 mg, about 20 to about 30 mg, about 25 to about 30 mg, about 1 to about 20 mg, about 2 to about 20 mg, about 5 to about 20 mg, about 10 to about 20 mg, about 15 to about 20 mg, about 1 to about 15 mg, about 2 to about 15 mg, about 5 to about 15 mg, about 10 to about 15 mg, about 1 to about 10 mg, about 2 to about 10 mg, or about 5 to about 10 mg. In yet other embodiments, the effective amount of crystalline Form I of aticaprant, crystalline Form II of aticaprant, crystalline Form III of aticaprant, or amorphous aticaprant is about 5 to about 15 mg. In still further embodiments, the effective amount of crystalline Form I of aticaprant, crystalline Form II of aticaprant, crystalline Form III of aticaprant, or amorphous aticaprant is about 10 mg.

Pharmaceutical Compositions

As used herein, the term "composition" is intended to encompass a product comprising the specified ingredients in the specified amounts, as well as any product which results, directly or indirectly, from combinations of the specified ingredients in the specified amounts. The preferred pharmaceutical composition contains crystalline Form I of aticaprant, crystalline Form II of aticaprant, crystalline Form III of aticaprant, or amorphous aticaprant as the active ingredient intimately admixed with a pharmaceutical carrier according to conventional pharmaceutical compounding techniques, which carrier may take a wide variety of forms depending on the form of preparation desired for administration. Suitable pharmaceutically acceptable carriers are well known in the art. Descriptions of some of these pharmaceutically acceptable carriers may be found in The Handbook of Pharmaceutical Excipients, published by the American Pharmaceutical Association and the Pharmaceutical Society of Great Britain.

Methods of formulating pharmaceutical compositions have been described in numerous publications such as Pharmaceutical Dosage Forms: Tablets, Second Edition, Revised and Expanded, Volumes 1-3, edited by Lieberman et al; Pharmaceutical Dosage Forms: Parenteral Medications, Volumes 1-2, edited by Avis et al; and Pharmaceutical Dosage Forms: Disperse Systems, Volumes 1-2, edited by Lieberman et al; published by Marcel Dekker, Inc.

In certain embodiments, pharmaceutical composition for use herein, the composition further comprises one or more buffers, preservatives, penetration agents, wetting agents, surfactants, solubilizing agents, thickening agents, colorant agents, antioxidants, emulsifying agents, isotonizing agents, suspending agents, and/or viscosity increasing agents.

In some embodiments, the pharmaceutical compositions comprises one or more buffers and/or buffer systems (i.e. conjugate acid-base-pairs). As used herein, the term "buffer" shall mean any solid or liquid composition (preferably an aqueous, liquid composition) which when added to an aqueous formulation adjusts the pH of said formulation. One skilled in the art will recognize that a buffer may adjust the pH of the aqueous formulation in any direction (toward more acidic, more basic or more neutral pH). Preferably, the buffer is pharmaceutically acceptable. Suitable examples of buffers which may be used in the aqueous formulations described herein include, but are not limited to citric acid, sodium dihydrogen phosphate, disodium hydrogen phosphate, acetic acid, boric acid, sodium borate, succinic acid, tartaric acid, malic acid, lactic acid, fumaric acid, and the like.

Optionally, the pharmaceutical compositions herein may contain a preservative. As used herein, unless otherwise noted, the terms "antimicrobial preservative" and "preservative" refer to any substance that is added to pharmaceutical compositions in order to preserve them against microbial degradation or microbial growth. In this regard, microbial growth typically plays an essential role, i.e., the preservative serves the main purpose of avoiding microbial contamination. It may also be desirable to avoid any effect of the microbes on the active ingredients and excipients, respectively, i.e., to avoid microbial degradation. Representative examples of preservatives include, but are not limited to, benzalkonium chloride, benzethonium chloride, benzoic acid, sodium benzoate, benzyl alcohol, bronopol, cetrimide, cetylpyridinium chloride, chlorhexidine, chlorbutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, sodium propionate, thimerosal, methyl paraben, ethyl paraben, propyl paraben, butyl paraben, isobutyl paraben, benzyl paraben, sorbic acid, and potassium sorbate.

As used herein, the terms "penetration agent", "penetration enhancer", and "penetrant" refer to any substance that increases or facilitates absorption and/or bioavailability of crystalline Form I of aticaprant, crystalline Form II of aticaprant, crystalline Form III of aticaprant, or amorphous aticaprant. Preferably, the penetration agent increases or facilitates absorption and/or bioavailability of crystalline Form I of aticaprant, crystalline Form II of aticaprant, crystalline Form III of aticaprant, or amorphous aticaprant, following administration. Suitable examples include, but are not limited to tetradecyl maltoside, sodium glycocholate, tauroursodeoxycholic acid, lecithines, and the like; and chitosan (and salts), and surface active ingredients such as benzalkonium chloride, sodium dodecyl sulfate, sodium docusate, polysorbates, laureth-9, oxtoxynol, sodium deoxycholate, polyarginine, and the like. Preferably, the penetration agent is selected to meet one or more of the following general requirements:

(a) It is effective at increasing absorption of crystalline Form I of aticaprant, crystalline Form II of aticaprant, crystalline Form III of aticaprant, or amorphous aticaprant, preferably in a temporary and/or reversible manner;
(b) It is pharmacologically inert;
(c) It is non-allergic, non-toxic and/or non-irritating;
(d) It is highly potent (effective in small amounts);
(e) It is compatible with the other components of the pharmaceutical composition;
(f) It is odorless, colorless and/or tasteless;
(g) It is accepted by regulatory agencies; and
(h) It is inexpensive and available in high purity.

The pharmaceutical compositions for use herein may further contain one or more additional excipients for example, wetting agents, surfactant components, solubilizing agents, thickening agents, colorant agents, antioxidant components, and the like.

Examples of a suitable antioxidant component, if used, include, but are not limited to one or more of the following: sulfites; ascorbic acid; ascorbates, such as sodium ascorbate, calcium ascorbate, or potassium ascorbate; ascorbyl palmitate; fumaric acid; ethylene diamine tetraacetic acid or its sodium or calcium salts; tocopherol; gallates, such as propyl gallate, octyl gallate, or dodecyl gallate; vitamin E; and mixtures thereof. The antioxidant component provides long term stability to the liquid compositions.

Solubilizing and emulsifying agents can be included to facilitate more uniform dispersion of the active ingredient or other excipient that is not generally soluble in the liquid carrier. Examples of a suitable emulsifying agent, if used, include, but are not limited to, for example, gelatin, cholesterol, acacia, tragacanth, pectin, methyl cellulose, carbomer, and mixtures thereof. Examples of suitable solubilizing agents include polyethylene glycol, glycerin, D-mannitol, trehalose, benzyl benzoate, ethanol, trisaminomethane, cholesterol, triethanolamine, sodium carbonate, sodium citrate, sodium salicylate, sodium acetate, and mixtures thereof. The solubilizing or emulsifying agent may be present in an amount sufficient to dissolve or disperse the active ingredient, i.e., crystalline Form I of aticaprant, crystalline Form II of aticaprant, crystalline Form III of aticaprant, or amorphous aticaprant, in the carrier.

A suitable isotonizing agent, if used, may include sodium chloride, glycerin, D-mannitol, D-sorbitol, glucose, and mixtures thereof.

Suspending agents or viscosity increasing agents may also be added to the pharmaceutical compositions. Suitable examples include, but are not limited to, hydroxypropyl methylcellulose, sodium carmellose, microcrystalline cellulose, carbomer, pectin, sodium alginate, chitosan salts, gellan gum, poloxamer, polyvinyl pyrrolidone, xanthan gum, and the like.

Advantageously, crystalline Form I of aticaprant, crystalline Form II of aticaprant, crystalline Form III of aticaprant, or amorphous aticaprant may be administered once daily, or the total daily dosage may be administered in divided doses of two, three or four times daily.

As described herein, in particular, the patient had an inadequate response to other antidepressant therapy prior to treatment with crystalline Form I of aticaprant, crystalline Form II of aticaprant, crystalline Form III of aticaprant, or amorphous aticaprant. Thus, in a particular embodiment, the disclosure relates to crystalline Form I of aticaprant, crystalline Form II of aticaprant, crystalline Form III of aticaprant, or amorphous aticaprant, for use as described herein, wherein the patient had an inadequate response to other antidepressant therapy prior to treatment with crystalline Form I of aticaprant, crystalline Form II of aticaprant, crystalline Form III of aticaprant, or amorphous aticaprant. In a further particular embodiment, the disclosure also relates to the use of crystalline Form I of aticaprant, crystalline Form II of aticaprant, crystalline Form III of aticaprant, or amorphous aticaprant in the manufacture of a medicament, as described herein, wherein the patient had an inadequate response to other antidepressant therapy prior to treatment with crystalline Form I of aticaprant, crystalline Form II of aticaprant, crystalline Form III of aticaprant, or amorphous aticaprant. In a further particular embodiment, the disclosure further relates to a package or pharmaceutical product as described herein, wherein the patient had an inadequate response to other antidepressant therapy prior to treatment with crystalline Form I of aticaprant, crystalline Form II of aticaprant, crystalline Form III of aticaprant, or amorphous aticaprant. Such antidepressant therapy can be in particular selected from a selective serotonin reuptake inhibitor (SSRI), serotonin-norepinephrine reuptake inhibitor (SNRI), or a combination thereof.

As described herein, crystalline Form I of aticaprant, crystalline Form II of aticaprant, crystalline Form III of aticaprant, or amorphous aticaprant may be used as adjunctive treatment, or in other words, in conjunction, as an add-on, or in combination with one or more antidepressants, for example, the patient may be already, or also, administered one or more antidepressants. Thus, in a further particular embodiment, the disclosure relates to crystalline Form I of aticaprant, crystalline Form II of aticaprant, crystalline Form III of aticaprant, or amorphous aticaprant, for use as described herein, comprising administration of crystalline Form I of aticaprant, crystalline Form II of aticaprant, crystalline Form III of aticaprant, or amorphous aticaprant, as adjunctive treatment with an effective amount of one or more antidepressants. In a further particular embodiment, the disclosure relates to aticaprant, for use as described herein, comprising administration of aticaprant, in conjunction with an effective amount of one or more antidepressants. In a further particular embodiment, the disclosure relates to crystalline Form I of aticaprant, crystalline Form II of aticaprant, crystalline Form III of aticaprant, or amorphous aticaprant, for use as described herein, comprising administration of crystalline Form I of aticaprant, crystalline Form II of aticaprant, crystalline Form III of aticaprant, or amorphous aticaprant, in combination with an effective amount of one or more antidepressants. In a further particular embodiment, the disclosure also relates to the use of crystalline Form I of aticaprant, crystalline Form II of aticaprant, crystalline Form III of aticaprant, or amorphous aticaprant, in the manufacture of a medicament, as described herein, wherein the treatment comprises administration of an effective amount of crystalline Form I of aticaprant, crystalline Form II of aticaprant, crystalline Form III of aticaprant, or amorphous aticaprant, as adjunctive treatment with an effective amount of one or more antidepressants. In a further particular embodiment, the disclosure also relates to the use of crystalline Form I of aticaprant, crystalline Form II of aticaprant, crystalline Form III of aticaprant, or amorphous aticaprant, as described herein, wherein the treatment comprises administration of an effective amount of crystalline Form I of aticaprant, crystalline Form II of aticaprant, crystalline Form III of aticaprant, or amorphous aticaprant, in conjunction with an effective amount of one or more antidepressants. In a further particular embodiment, the disclosure also relates to the use of crystalline Form I of aticaprant, crystalline Form II of aticaprant, crystalline Form III of aticaprant, or amorphous aticaprant, as described herein, wherein the treatment comprises administration of an effective amount of crystalline Form I of aticaprant, crystalline Form II of aticaprant, crystalline Form III of aticaprant, or amorphous aticaprant, in combination with an effective amount of one or more antidepressants. In a further particular embodiment, the disclosure further relates to a package or pharmaceutical product as described herein, wherein the instructions for treatment direct the administration of an effective amount of crystalline Form I of aticaprant, crystalline Form II of aticaprant, crystalline Form III of aticaprant, or amorphous aticaprant, as adjunctive treatment with an effective amount of one or more antidepressants. In a further particular embodiment, the disclosure further relates to a package or pharmaceutical product as described herein, wherein the instructions for treatment direct the administration of an effective amount of crystalline Form I of aticaprant, crystalline Form II of aticaprant, crystalline Form III of aticaprant, or amorphous aticaprant, in conjunction with an effective amount of one or more antidepressants. In a further particular embodiment, the disclosure further relates to a package or pharmaceutical as described herein, wherein the instructions for treatment direct administration of an effective amount of crystalline Form I of aticaprant, crystalline Form II of aticaprant, crystalline Form III of aticaprant, or amorphous aticaprant, in combination with an effective amount of one or more antidepressants. Such one or more antidepressants can be selected from a selective serotonin reuptake inhibitor (SSRI), serotonin-norepinephrine reuptake inhibitor (SNRI), or a combination thereof.

As already described, the disclosure relates to crystalline Form I of aticaprant, crystalline Form II of aticaprant, crystalline Form III of aticaprant, or amorphous aticaprant, for use as described herein. In a particular embodiment, crystalline Form I of aticaprant, crystalline Form II of aticaprant, crystalline Form III of aticaprant, or amorphous aticaprant is S-aticaprant. In a further embodiment of the disclosure, crystalline Form I of aticaprant, crystalline Form II of aticaprant, crystalline Form III of aticaprant, or amorphous aticaprant, in particular S-aticaprant, for use as described herein, is to be administered in an amount of about 2 to about 35 mg, more in particular, of about 10 mg. In a yet further embodiment, crystalline Form I of aticaprant, crystalline Form II of aticaprant, crystalline Form III of aticaprant, or amorphous aticaprant, in particular S-aticaprant, for use as described herein, is administered orally. Furthermore, in a further particular embodiment, the disclosure relates to crystalline Form I of aticaprant, crystalline Form II of aticaprant, crystalline Form III of aticaprant, or amorphous aticaprant, in particular S-aticaprant, for use as described herein, administered once daily. The disclosure also relates to the use of aticaprant, in the manufacture of a medicament, as described herein. In a particular embodiment, crystalline Form I of aticaprant, crystalline Form II of aticaprant, crystalline Form III of aticaprant, or amorphous aticaprant is S-aticaprant. In a further embodiment of the use as described herein, about 2 to about 35 mg crystalline Form I of aticaprant, crystalline Form II of aticaprant, crystalline Form III of aticaprant, or amorphous aticaprant is to be administered, more in particular, about 10 mg. In a yet further embodiment of the use, crystalline Form I of aticaprant, crystalline Form II of aticaprant, crystalline Form III of aticaprant, or amorphous aticaprant is to be administered orally. Furthermore, in a further particular embodiment of the use the crystalline Form I of aticaprant, crystalline Form II of aticaprant, crystalline Form III of aticaprant, or amorphous aticaprant, in particular S-aticaprant, is to be administered once daily. In a further particular embodiment, the disclosure further relates to a package or pharmaceutical product as described herein, wherein crystalline Form I of aticaprant, crystalline Form II of aticaprant, crystalline Form III of aticaprant, or amorphous aticaprant is in particular S-aticaprant. In a further embodiment of the package or pharmaceutical product as described herein, the instructions for treatment direct administration of about 2 to about 35 mg crystalline Form I of aticaprant, crystalline Form II of aticaprant, crystalline Form III of aticaprant, or amorphous aticaprant, more in particular, about 10 mg. In a yet further embodiment of the package or pharmaceutical product as described herein, the instructions for treatment direct crystalline Form I of aticaprant, crystalline Form II of aticaprant, crystalline Form III of aticaprant, or amorphous aticaprant, in particular S-aticaprant, is for oral administration. Furthermore, in a further particular embodiment of the package or pharmaceutical product, as described herein, the instructions for treatment direct crystalline Form I of aticaprant, crystalline Form II of aticaprant, crystalline Form III of aticaprant, or amorphous aticaprant, in particular S-aticaprant, is for once daily administration.

Advantageously, administration of crystalline Form I of aticaprant, crystalline Form II of aticaprant, crystalline Form III of aticaprant, or amorphous aticaprant does not result in weight gain during treatment, including clinically relevant weight gain. Thus, in a further particular embodiment, the disclosure relates to crystalline Form I of aticaprant, crystalline Form II of aticaprant, crystalline Form III of aticaprant, or amorphous aticaprant, for use as described herein, wherein the patient does not experience weight gain during the treatment with crystalline Form I of aticaprant, crystalline Form II of aticaprant, crystalline Form III of aticaprant, or amorphous aticaprant. In a further particular embodiment, the disclosure relates to a use as defined herein, wherein the patient does not experience weight gain during the treatment with crystalline Form I of aticaprant, crystalline Form II of aticaprant, crystalline Form III of aticaprant, or amorphous aticaprant. In a further particular embodiment, the disclosure further relates to a package or pharmaceutical product as described herein, wherein the patient does not experience weight gain during the treatment with crystalline Form I of aticaprant, crystalline Form II of aticaprant, crystalline Form III of aticaprant, or amorphous aticaprant. The body weight of the patient can in particular be assessed at the time of the initial administration of aticaprant.

It was also unexpectedly observed that, based on assessment at the time of initial administration, the patient does not experience a decrease in sexual functioning during the treatment with crystalline Form I of aticaprant, crystalline Form II of aticaprant, crystalline Form III of aticaprant, or amorphous aticaprant. Thus, in further particular embodiment, the disclosure relates to crystalline Form I of aticaprant, crystalline Form II of aticaprant, crystalline Form III of aticaprant, or amorphous aticaprant, for use as described herein, wherein the patient does not experience a decrease in sexual functioning during the treatment with crystalline Form I of aticaprant, crystalline Form II of aticaprant, crystalline Form III of aticaprant, or amorphous aticaprant. In a further particular embodiment, the disclosure relates to a use as described herein, wherein the patient does not experience a decrease in sexual functioning during the treatment with crystalline Form I of aticaprant, crystalline Form II of aticaprant, crystalline Form III of aticaprant, or amorphous aticaprant. In a further particular embodiment, the disclosure relates to a package or pharmaceutical product as described herein, wherein the patient does not experience a decrease in sexual functioning during the treatment with crystalline Form I of aticaprant, crystalline Form II of aticaprant, crystalline Form III of aticaprant, or amorphous aticaprant. Such term "sexual functioning" comprises sexual drive, sexual arousal, vaginal lubrication, erection, orgasm achievement, or orgasm satisfaction. Sexual satisfaction can be assessed by methods known to the skilled person, for example, by applying the Arizona Sexual Experience Scale (ASEX).

As already described, the patient has anhedonia. In certain aspects, the anhedonia is moderate. In other aspects, the anhedonia is severe. Anhedonia can be measured, through an anhedonia scale, for example, the Snaith Hamilton Pleasure Scale (SHAPS). Thus, in a particular embodiment, the disclosure relates to crystalline Form I of aticaprant, crystalline Form II of aticaprant, crystalline Form III of aticaprant, or amorphous aticaprant, for use as described herein, wherein the anhedonia of the patient is reduced by at least 40%, as measured by the change from baseline in total score in an anhedonia scale following 6 weeks of the treatment with crystalline Form I of aticaprant, crystalline Form II of aticaprant, crystalline Form III of aticaprant, or amorphous aticaprant, more in particular, the anhedonia of the patient is reduced within about 3 weeks to about 6 weeks as measured by the change from baseline in total score in an anhedonia scale. In a further particular embodiment, the anhedonia scale is the Snaith Hamilton Pleasure Scale (SHAPS). Thus, in a particular embodiment, the disclosure relates to the use as described herein, wherein the anhedonia of the patient is reduced by at least 40%, as measured by the change from baseline in total score in an anhedonia scale following 6 weeks of the treatment with crystalline Form I of aticaprant, crystalline Form II of aticaprant, crystalline Form III of aticaprant, or amorphous aticaprant, more in particular, the anhedonia of the patient is reduced within about 3 weeks to about 6 weeks as measured by the change from baseline in total score in an anhedonia scale. In a further particular embodiment, the anhedonia scale is the Snaith Hamilton Pleasure Scale (SHAPS). In a further particular embodiment, the disclosure relates to the package or pharmaceutical product as described herein, wherein the anhedonia of the patient is reduced by at least 40%, as measured by the change from baseline in total score in an anhedonia scale following 6 weeks of the treatment with crystalline Form I of aticaprant, crystalline Form II of aticaprant, crystalline Form III of aticaprant, or amorphous aticaprant, more in particular, the anhedonia of the patient is reduced within about 3 weeks to about 6 weeks as measured by the change from baseline in total score in an anhedonia scale. In a further particular embodiment, the anhedonia scale is the Snaith Hamilton Pleasure Scale (SHAPS).

Embodiments

The invention provides also the following non-limiting embodiments:

Embodiment 1 is a crystalline Form I of aticaprant that is characterized by four or more x-ray diffraction pattern peaks at 2θ (±0.2) of 4.6°, 17.3°, 17.4°, 18.0°, and 24.0°, wherein aticaprant has the following structure:

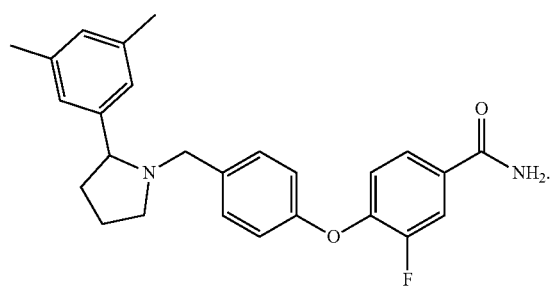 [SMILES: Cc1cc(C)cc(C2CCCN2Cc2ccc(Oc3ccc(C(N)=O)cc3F)cc2)c1]

Embodiment 2 is the crystalline Form I of aticaprant that is characterized by an x-ray powder diffraction pattern that corresponds to FIG. 6.

Embodiment 3 is the crystalline Form I of aticaprant of Embodiment 1 or 2 that is characterized by a differential scanning calorimetry thermogram comprising one endotherm at about 92.9° C.

Figure 7:
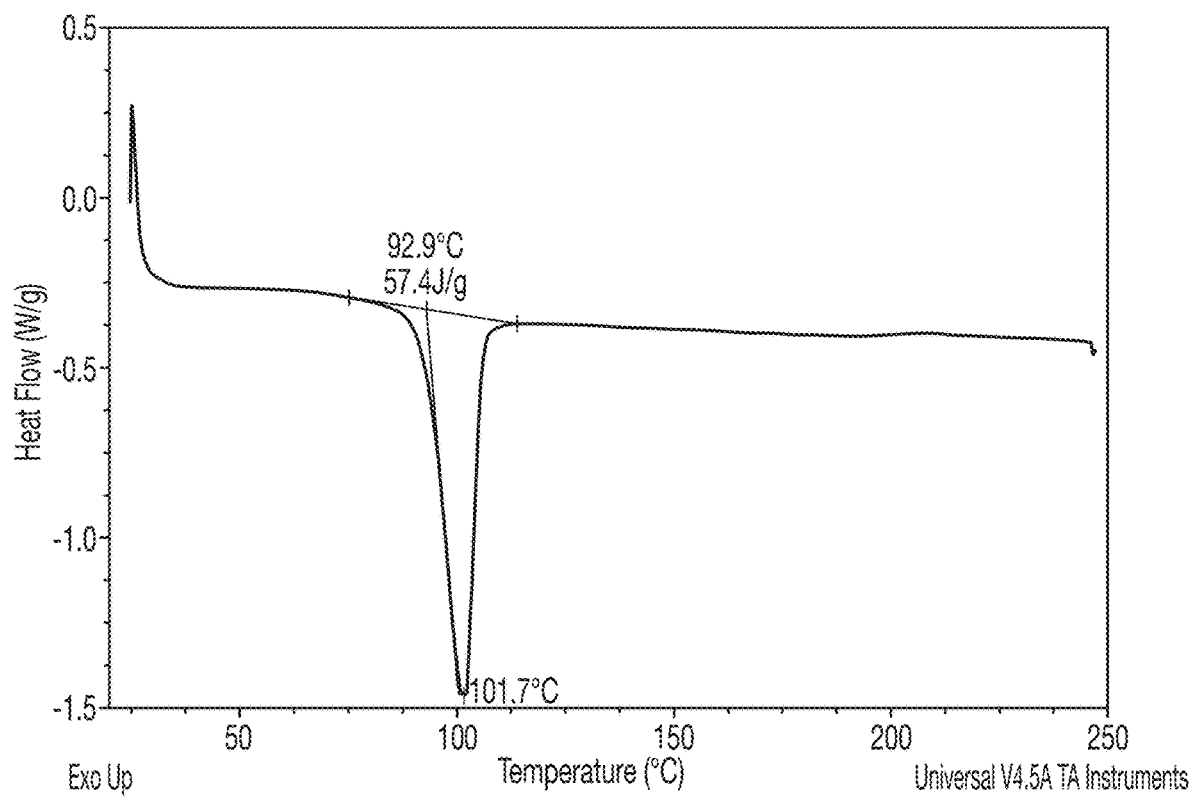
FIG. 7 is the DSC thermogram of crystalline Form I of aticaprant.

Embodiment 4 is the crystalline Form I of aticaprant of any one of Embodiments 1-3 that is characterized by a differential scanning calorimetry thermogram that corresponds to FIG. 7.

Embodiment 5 is the crystalline Form I of aticaprant of any one of Embodiments 1~4 that is anhydrous.

Embodiment 6 is the crystalline Form II of aticaprant that is characterized by four or more x-ray diffraction pattern peaks at 2θ (±0.2) of 3.1°, 19.0°, 24.0°, 24.3°, or 26.2°, wherein aticaprant has the following structure:

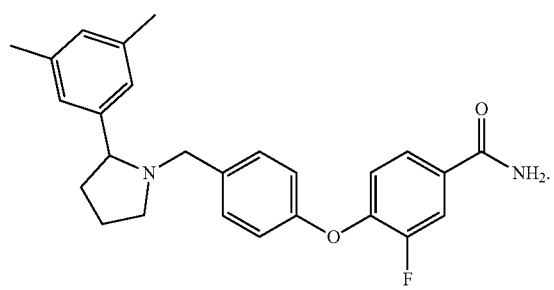 [SMILES: Cc1cc(C)cc(C2CCCN2Cc2ccc(Oc3ccc(C(N)=O)cc3F)cc2)c1]

Embodiment 7 is the crystalline Form II of aticaprant of Embodiment 6 that is characterized by an x-ray powder diffraction pattern that corresponds to FIG. 8.

Embodiment 8 is the crystalline Form II of aticaprant of Embodiment 6 or 7 that is characterized by a differential scanning calorimetry thermogram comprising one or both endotherms at about 74.7° C. and about 96.2° C.

Figure 9:
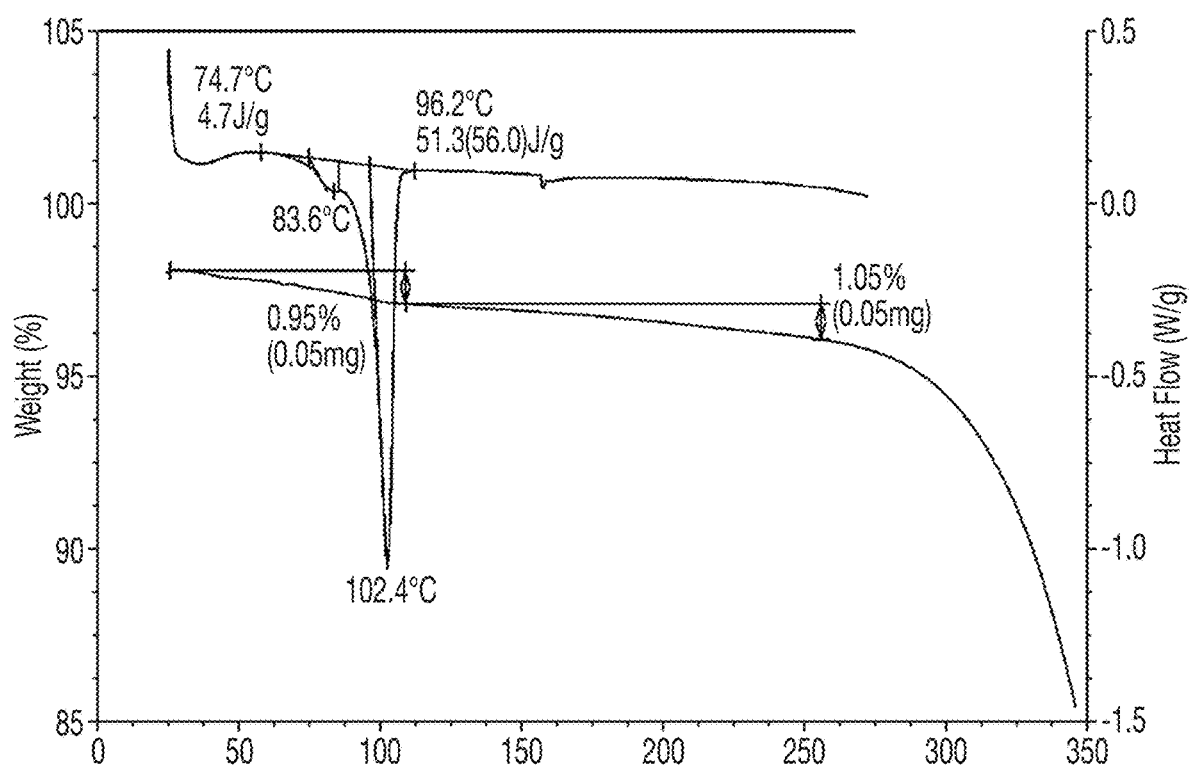
FIG. 9 is the mDSC thermogram of crystalline Form II of aticaprant (1 g scale).

Embodiment 9 is the crystalline Form II of aticaprant of any one of Embodiments 6-8 that is characterized by a differential scanning calorimetry thermogram that corresponds to FIG. 9.

Embodiment 10 is the crystalline Form II of aticaprant of any one of Embodiments 6-9 that is anhydrous.

Embodiment 11 is a crystalline Form III of aticaprant that is characterized by four or more x-ray diffraction pattern peaks at 2θ (±0.2) of 4.1°, 9.0°, 17.6°, 18.0°, or 21.4°, wherein aticaprant has the following structure:

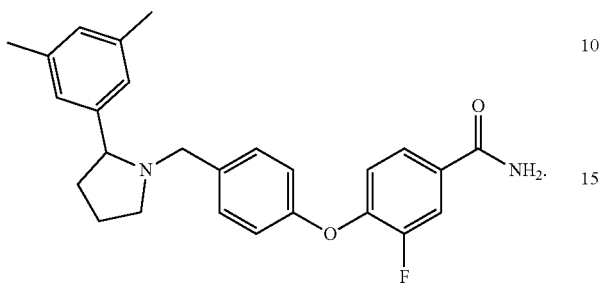

Embodiment 12 The crystalline Form III of aticaprant of Embodiment 11 that is characterized by an x-ray powder diffraction pattern that corresponds to FIG. 1.

Embodiment 13 is the crystalline Form III of aticaprant of Embodiment 11 or 12 that is characterized by a peak temperature ($T_m$) at about 121° C.

Figure 4:
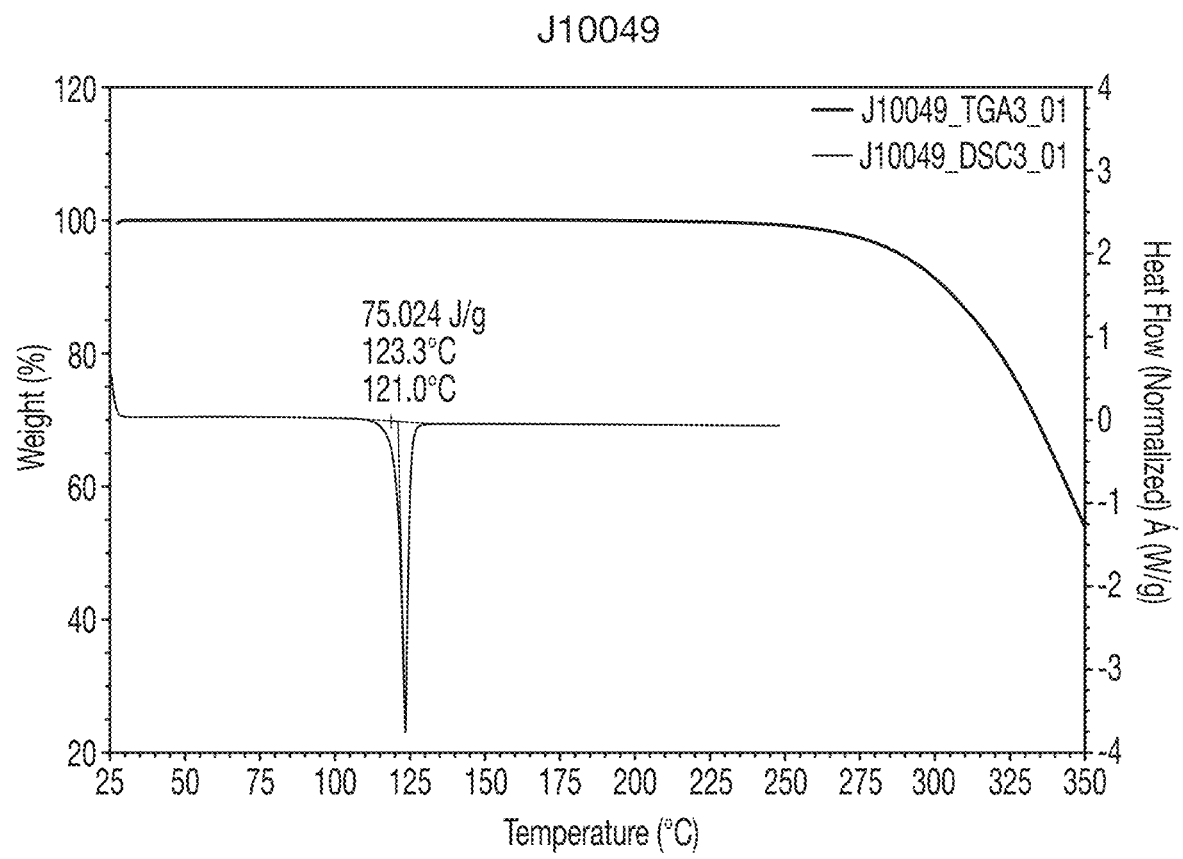
FIG. 4 is the differential scanning calorimetry (DSC) thermogram of Form III of aticaprant.

Embodiment 14 is the crystalline Form III of aticaprant of any one of Embodiments 11-13 that is characterized by a differential scanning calorimetry thermogram that corresponds to FIG. 4.

Embodiment 15 is the crystalline Form III of aticaprant of any one of Embodiments 11-14 that is anhydrous.

Embodiment 16 is an amorphous form of aticaprant, wherein aticaprant has the following structure:

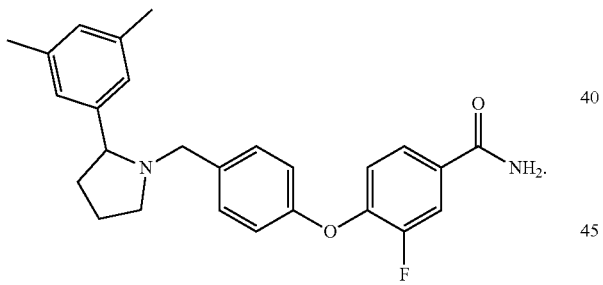

Embodiment 17 is the amorphous form of Embodiment 16 that is characterized by a differential scanning calorimetry thermogram comprising a $T_g$ of about 45.5° C.

Figure 3:
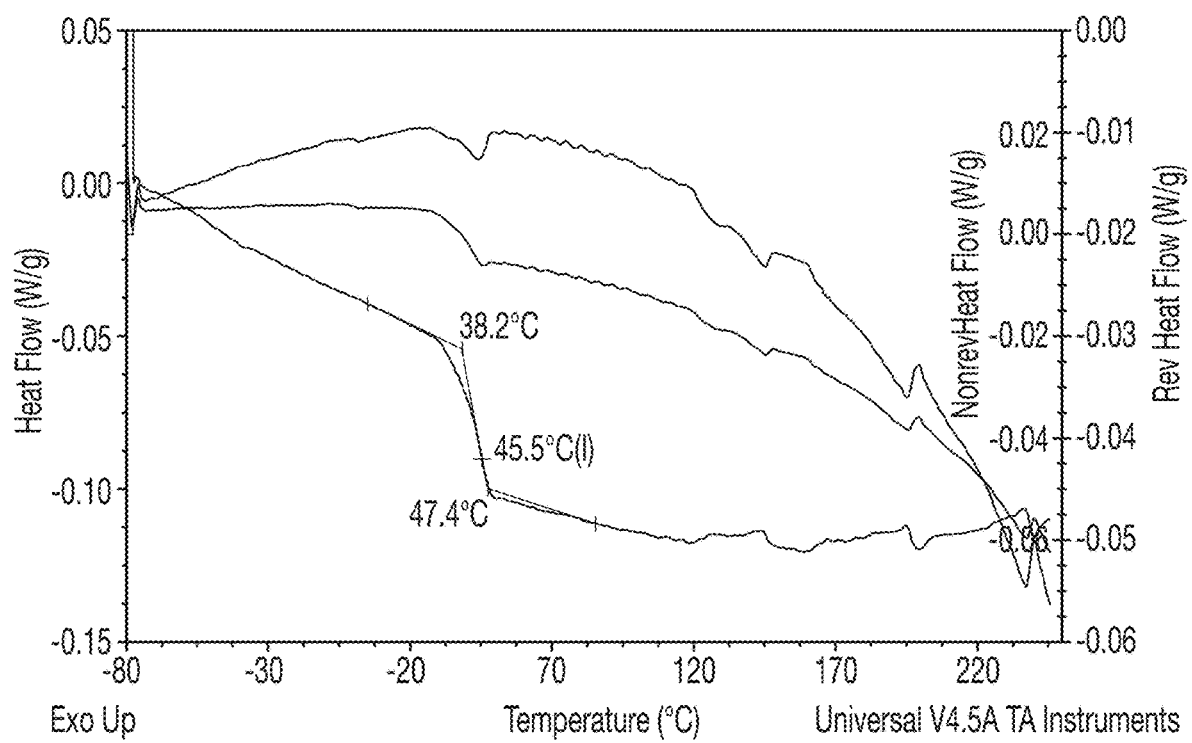
FIG. 3 is the modulated differential scanning calorimetry (mDSC) thermogram of amorphous aticaprant.

Embodiment 18 is the amorphous form of aticaprant of Embodiment 16 or 17 that is characterized by a differential scanning calorimetry thermogram that corresponds to FIG. 3.

Embodiment 19 is a pharmaceutical composition comprising the crystalline form of aticaprant of any one of Embodiments 1-15 or the amorphous form of aticaprant of any one of Embodiments 16-18.

Embodiment 20 is a method of treating major depressive disorder in a human patient with crystalline aticaprant.

Embodiment 21 is a method of treating major depressive disorder in human patient, comprising administering crystalline aticaprant to the human patient, wherein the patient had a previous inadequate response to other antidepressant therapy.

Embodiment 22 is a method of treating major depressive disorder in a human patient, comprising administering to the human patient in need thereof an effective amount of a crystalline form of aticaprant of any one of Embodiments 1-15 or an amorphous form of aticaprant of any one of Embodiments 16-18.

Embodiment 23 is the method of Embodiment 22, wherein the treatment comprises administration of an effective amount of the crystalline form of aticaprant or amorphous form of aticaprant.

Embodiment 24 is the method of Embodiment 22 or 23, wherein the patient had an inadequate response to other antidepressant therapy prior to treatment with the crystalline form of aticaprant or the amorphous form of aticaprant.

Embodiment 25 is the method of any one of Embodiment 21, 23, or 24, wherein the other antidepressant therapy is a selective serotonin reuptake inhibitor, serotonin-norepinephrine reuptake inhibitor, or a combination thereof.

Embodiment 26 is the method of any one of Embodiments 20-25, further comprising adjunctive treatment with an effective amount of one or more antidepressants.

Embodiment 27 is the method of any one of Embodiments 20-26, wherein the one or more antidepressants is a selective serotonin reuptake inhibitor, serotonin-norepinephrine reuptake inhibitor, or a combination thereof.

Embodiment 28 is the method of any one of Embodiments 20-27, wherein the crystalline form of aticaprant is the crystalline form of S-aticaprant or the amorphous form of aticaprant is the amorphous form of S-aticaprant.

Embodiment 29 is the method of any one of Embodiments 20-28, wherein the effective amount of the crystalline form of aticaprant or the amorphous form of aticaprant is about 2 to about 35 mg.

Embodiment 30 is the method of Embodiment 29, wherein the effective amount of the crystalline form of aticaprant or the amorphous form of aticaprant is about 10 mg.

Embodiment 31 is the method of any one of Embodiments 20-30, wherein the crystalline form of aticaprant or the amorphous form of aticaprant is administered orally.

Embodiment 32 is the method of any one of Embodiments 20-31, wherein the crystalline form of aticaprant or the amorphous form of aticaprant is administered once daily.

Embodiment 33 is the method of any one of Embodiments 20-32, wherein the patient has anhedonia.

Embodiment 34 is the method of any one of Embodiments 20-33, wherein the patient has moderate anhedonia.

Embodiment 35 is the method of any one of Embodiments 20-33, wherein the patient has severe anhedonia.

Embodiment 36 is the method of any one of Embodiments 22-35, wherein the patient does not experience weight gain during the treatment with the crystalline form of aticaprant or the amorphous form of aticaprant.

Embodiment 37 is the method of Embodiment 36, wherein patient's body weight is assessed at the time of the initial administration of the crystalline form of aticaprant or the amorphous form of aticaprant.

Embodiment 38 is the method of any one of Embodiments 20-37, wherein the patient does not experience a decrease in sexual functioning during the treatment with the crystalline form of aticaprant or the amorphous form of aticaprant.

Embodiment 39 is the method of Embodiment 38, wherein the sexual functioning of the patient is assessed at the time of initial administration of the crystalline form of aticaprant or the amorphous form of aticaprant.

Embodiment 40 is the method of Embodiment 38 or 39, wherein the sexual functioning comprises sexual drive, sexual arousal, vaginal lubrication, erection, orgasm achievement, or orgasm satisfaction.

Embodiment 41 is the method of any one of Embodiments 38-40, wherein sexual functioning is assessed by the Arizona Sexual Experience Scale.

Embodiment 42 is the method of any one of Embodiments 33-35, wherein the anhedonia of the patient is reduced by at least 40%, as measured by the change from baseline in total score in an anhedonia scale following 6 weeks of the treatment with the crystalline form of aticaprant or the amorphous form of aticaprant.

Embodiment 43 is the method of any one of Embodiments 33-35 and 42, wherein the anhedonia of the patient is reduced within about 3 weeks to about 6 weeks as measured by the change from baseline in total score in an anhedonia scale.

Embodiment 44 is the method of Embodiment 42 or 43, wherein the anhedonia scale is the Snaith Hamilton Pleasure Scale.

Embodiment 45 is crystalline form of aticaprant for treating major depressive disorder in a human patient.

Embodiment 46 is crystalline form of aticaprant of any one of Embodiments 1-15 for treating major depressive disorder in human patient, wherein the patient had a previous inadequate response to other antidepressant therapy.

Embodiment 47 is crystalline form of aticaprant of any one of Embodiments 1-15 for treating major depressive disorder in a human patient.

Embodiment 48 is crystalline form of aticaprant of Embodiment 47, wherein the treatment comprises administration of an effective amount of the crystalline form of aticaprant or amorphous form of aticaprant.

Embodiment 49 is crystalline form of aticaprant of Embodiment 47 or 48, wherein the patient had an inadequate response to other antidepressant therapy prior to treatment with the crystalline form of aticaprant or the amorphous form of aticaprant.

Embodiment 50 is crystalline form of aticaprant of any one of Embodiments 46 or 49, wherein the other antidepressant therapy is a selective serotonin reuptake inhibitor, serotonin-norepinephrine reuptake inhibitor, or a combination thereof.

Embodiment 51 is crystalline form of aticaprant of any one of Embodiments 45-50, further comprising adjunctive treatment with an effective amount of one or more antidepressants.

Embodiment 52 is crystalline form of aticaprant of any one of Embodiments 45-51, wherein the one or more antidepressants is a selective serotonin reuptake inhibitor, serotonin-norepinephrine reuptake inhibitor, or a combination thereof.

Embodiment 53 is crystalline form of aticaprant of any one of Embodiments 45-52, wherein the crystalline form of aticaprant is the crystalline form of S-aticaprant or the amorphous form of aticaprant is the amorphous form of S-aticaprant.

Embodiment 54 is crystalline form of aticaprant of any one of Embodiments 45-53, wherein the effective amount of the crystalline form of aticaprant or the amorphous form of aticaprant is about 2 to about 35 mg.

Embodiment 55 is crystalline form of aticaprant of Embodiments 54, wherein the effective amount of the crystalline form of aticaprant or the amorphous form of aticaprant is about 10 mg.

Embodiment 56 crystalline form of aticaprant of any one of Embodiments 45-55, wherein the crystalline form of aticaprant or the amorphous form of aticaprant is administered orally.

Embodiment 57 is crystalline form of aticaprant of any one of Embodiments 45-56, wherein the crystalline form of aticaprant or the amorphous form of aticaprant is administered once daily.

Embodiment 58 is crystalline form of aticaprant of any one of Embodiments 45-57, wherein the patient has anhedonia.

Embodiment 59 is crystalline form of aticaprant of any one of Embodiments 45-58, wherein the patient has moderate anhedonia.

Embodiment 60 is crystalline form of aticaprant of any one of Embodiments 45-58, wherein the patient has severe anhedonia.

Embodiment 61 is crystalline form of aticaprant of any one of Embodiments 47-60, wherein the patient does not experience weight gain during the treatment with the crystalline form of aticaprant or the amorphous form of aticaprant.

Embodiment 62 is crystalline form of aticaprant of Embodiment 61, wherein patient's body weight is assessed at the time of the initial administration of the crystalline form of aticaprant or the amorphous form of aticaprant.

Embodiment 63 is crystalline form of aticaprant of any one of Embodiments 45-62, wherein the patient does not experience a decrease in sexual functioning during the treatment with the crystalline form of aticaprant or the amorphous form of aticaprant.

Embodiment 64 is crystalline form of aticaprant of Embodiment 63, wherein the sexual functioning of the patient is assessed at the time of initial administration of the crystalline form of aticaprant or the amorphous form of aticaprant.

Embodiment 65 is a crystalline form of aticaprant of Embodiment 63 or 64, wherein the sexual functioning comprises sexual drive, sexual arousal, vaginal lubrication, erection, orgasm achievement, or orgasm satisfaction.

Embodiment 66 is a crystalline form of aticaprant of any one of Embodiments 63-65, wherein sexual functioning is assessed by the Arizona Sexual Experience Scale.

Embodiment 67 is the crystalline form of aticaprant of any one of Embodiments 58-60, wherein the anhedonia of the patient is reduced by at least 40%, as measured by the change from baseline in total score in an anhedonia scale following 6 weeks of the treatment with the crystalline form of aticaprant or the amorphous form of aticaprant.

Embodiment 68 is the crystalline form of aticaprant of any one of Embodiments 58-60 and 67, wherein the anhedonia of the patient is reduced within about 3 weeks to about 6 weeks as measured by the change from baseline in total score in an anhedonia scale.

Embodiment 69 is the crystalline form of aticaprant of Embodiment 67 or 68, wherein the anhedonia scale is the Snaith Hamilton Pleasure Scale.

Embodiment 70 is the amorphous form of aticaprant for treating major depressive disorder in a human patient.

Embodiment 71 is the amorphous form of aticaprant of any one of Embodiments 16-18 for treating major depressive disorder in human patient, wherein the patient had a previous inadequate response to other antidepressant therapy.

Embodiment 72 is the amorphous form of aticaprant of any one of Embodiments 16-18 for treating major depressive disorder in a human patient.

Embodiment 73 is the amorphous form of aticaprant of Embodiment 72, wherein the treatment comprises administration of an effective amount of the crystalline form of aticaprant or amorphous form of aticaprant.

Embodiment 74 is the amorphous form of aticaprant of Embodiment 72 or 73, wherein the patient had an inadequate response to other antidepressant therapy prior to treatment with the crystalline form of aticaprant or the amorphous form of aticaprant.

Embodiment 75 is the amorphous form of aticaprant of any one of Embodiments 71 or 74, wherein the other antidepressant therapy is a selective serotonin reuptake inhibitor, serotonin-norepinephrine reuptake inhibitor, or a combination thereof.

Embodiment 76 is the amorphous form of aticaprant of any one of Embodiments 70-75, further comprising adjunctive treatment with an effective amount of one or more antidepressants.

Embodiment 77 is the amorphous form of aticaprant of any one of Embodiments 70-76, wherein the one or more antidepressants is a selective serotonin reuptake inhibitor, serotonin-norepinephrine reuptake inhibitor, or a combination thereof.

Embodiment 78 is the amorphous form of aticaprant of any one of Embodiments 70-77, wherein the crystalline form of aticaprant is the crystalline form of S-aticaprant or the amorphous form of aticaprant is the amorphous form of S-aticaprant.

Embodiment 79 is the amorphous form of aticaprant of any one of Embodiments 70-78, wherein the effective amount of the crystalline form of aticaprant or the amorphous form of aticaprant is about 2 to about 35 mg.

Embodiment 80 is the amorphous form of aticaprant of Embodiment 79, wherein the effective amount of the crystalline form of aticaprant or the amorphous form of aticaprant is about 10 mg.

Embodiment 81 is the amorphous form of aticaprant of any one of Embodiments 70-80, wherein the crystalline form of aticaprant or the amorphous form of aticaprant is administered orally.

Embodiment 82 is the amorphous form of aticaprant of any one of Embodiments 70-81, wherein the crystalline form of aticaprant or the amorphous form of aticaprant is administered once daily.

Embodiment 83 is the amorphous form of aticaprant of any one of Embodiments 70-82, wherein the patient has anhedonia.

Embodiment 84 is the amorphous form of aticaprant of any one of Embodiments 70-83, wherein the patient has moderate anhedonia.

Embodiment 85 is the amorphous form of aticaprant of any one of Embodiments 70-84, wherein the patient has severe anhedonia.

Embodiment 86 is the amorphous form of aticaprant of any one of Embodiments 72-85, wherein the patient does not experience weight gain during the treatment with the crystalline form of aticaprant or the amorphous form of aticaprant.

Embodiment 87 is the amorphous form of aticaprant of Embodiment 86, wherein patient's body weight is assessed at the time of the initial administration of the crystalline form of aticaprant or the amorphous form of aticaprant.

Embodiment 88 is the amorphous form of aticaprant of any one of Embodiments 70-87, wherein the patient does not experience a decrease in sexual functioning during the treatment with the crystalline form of aticaprant or the amorphous form of aticaprant.

Embodiment 89 is the amorphous form of aticaprant of Embodiment 88, wherein the sexual functioning of the patient is assessed at the time of initial administration of the crystalline form of aticaprant or the amorphous form of aticaprant.

Embodiment 90 is the amorphous form of aticaprant of Embodiment 88 or 89, wherein the sexual functioning comprises sexual drive, sexual arousal, vaginal lubrication, erection, orgasm achievement, or orgasm satisfaction.

Embodiment 91 is the amorphous form of aticaprant of any one of Embodiments 88-90, wherein sexual functioning is assessed by the Arizona Sexual Experience Scale.

Embodiment 92 is the amorphous form of aticaprant of any one of Embodiments 83-85, wherein the anhedonia of the patient is reduced by at least 40%, as measured by the change from baseline in total score in an anhedonia scale following 6 weeks of the treatment with the crystalline form of aticaprant or the amorphous form of aticaprant.

Embodiment 93 is the amorphous form of aticaprant of any one of Embodiments 83-85 and 92, wherein the anhedonia of the patient is reduced within about 3 weeks to about 6 weeks as measured by the change from baseline in total score in an anhedonia scale.

Embodiment 94 is the amorphous form of aticaprant of Embodiment 92 or 93, wherein the anhedonia scale is the Snaith Hamilton Pleasure Scale.

Embodiment 95 is the use of a crystalline form of aticaprant or amorphous form of aticaprant in the manufacture of a medicament for treating major depressive disorder in a human patient.

Embodiment 96 is the use of the crystalline form of aticaprant of any one of Embodiments 1-15 or the amorphous form of aticaprant of any one of Embodiments 16-18 in the preparation of a medicament for treating major depressive disorder in human patient, wherein the patient had a previous inadequate response to other antidepressant therapy.

Embodiment 97 is the use of the crystalline form of aticaprant of any one of Embodiments 1-15 or the amorphous form of aticaprant of any one of Embodiments 16-18 in the preparation of a medicament for treating major depressive disorder in a human patient.

Embodiment 98 is the use of Embodiment 97, wherein the treatment comprises administration of an effective amount of the crystalline form of aticaprant or amorphous form of aticaprant.

Embodiment 99 is the use of Embodiment 97 or 98, wherein the patient had an inadequate response to other antidepressant therapy prior to treatment with the crystalline form of aticaprant or the amorphous form of aticaprant.

Embodiment 100 is the use of any one of Embodiment 96 or 99, wherein the other antidepressant therapy is a selective serotonin reuptake inhibitor, serotonin-norepinephrine reuptake inhibitor, or a combination thereof.

Embodiment 101 is the use of any one of Embodiments 95-100, further comprising adjunctive treatment with an effective amount of one or more antidepressants.

Embodiment 102 is the use of any one of Embodiments 95-101, wherein the one or more antidepressants is a selective serotonin reuptake inhibitor, serotonin-norepinephrine reuptake inhibitor, or a combination thereof.

Embodiment 103 is the amorphous form of aticaprant of any one of Embodiments 95-102, wherein the crystalline form of aticaprant is the crystalline form of S-aticaprant or the amorphous form of aticaprant is the amorphous form of S-aticaprant.

Embodiment 104 is the amorphous form of aticaprant of any one of Embodiments 95-103, wherein the effective amount of the crystalline form of aticaprant or the amorphous form of aticaprant is about 2 to about 35 mg.

Embodiment 105 is the amorphous form of aticaprant of Embodiment 104, wherein the effective amount of the crystalline form of aticaprant or the amorphous form of aticaprant is about 10 mg.

Embodiment 106 is the amorphous form of aticaprant of any one of Embodiments 95-105, wherein the crystalline form of aticaprant or the amorphous form of aticaprant is administered orally.

Embodiment 107 is the amorphous form of aticaprant of any one of Embodiments 95-106, wherein the crystalline form of aticaprant or the amorphous form of aticaprant is administered once daily.

Embodiment 108 is the amorphous form of aticaprant of any one of Embodiments 95-107, wherein the patient has anhedonia.

Embodiment 109 is the amorphous form of aticaprant of any one of Embodiments 95-83, wherein the patient has moderate anhedonia.

Embodiment 110 is the amorphous form of aticaprant of any one of Embodiments 95-84, wherein the patient has severe anhedonia.

Embodiment 111 is the amorphous form of aticaprant of any one of Embodiments 77-85, wherein the patient does not experience weight gain during the treatment with the crystalline form of aticaprant or the amorphous form of aticaprant.

Embodiment 112 is the amorphous form of aticaprant of Embodiment 111, wherein patient's body weight is assessed at the time of the initial administration of the crystalline form of aticaprant or the amorphous form of aticaprant.

Embodiment 113 is the amorphous form of aticaprant of any one of Embodiments 95-112, wherein the patient does not experience a decrease in sexual functioning during the treatment with the crystalline form of aticaprant or the amorphous form of aticaprant.

Embodiment 114 is the amorphous form of aticaprant of Embodiment 113, wherein the sexual functioning of the patient is assessed at the time of initial administration of the crystalline form of aticaprant or the amorphous form of aticaprant.

Embodiment 115 is the amorphous form of aticaprant of Embodiment 113 or 114, wherein the sexual functioning comprises sexual drive, sexual arousal, vaginal lubrication, erection, orgasm achievement, or orgasm satisfaction.

Embodiment 116 is the amorphous form of aticaprant of any one of Embodiments 113-114, wherein sexual functioning is assessed by the Arizona Sexual Experience Scale.

Embodiment 117 is the amorphous form of aticaprant of any one of Embodiments 108-110, wherein the anhedonia of the patient is reduced by at least 40%, as measured by the change from baseline in total score in an anhedonia scale following 6 weeks of the treatment with the crystalline form of aticaprant or the amorphous form of aticaprant.

Embodiment 118 is the amorphous form of aticaprant of any one of Embodiments 108-110 and 117, wherein the anhedonia of the patient is reduced within about 3 weeks to about 6 weeks as measured by the change from baseline in total score in an anhedonia scale.

Embodiment 119 is the amorphous form of aticaprant of Embodiment 117 or 118, wherein the anhedonia scale is the Snaith Hamilton Pleasure Scale.

Embodiment 120 is a package or pharmaceutical product comprising (i) the crystalline form of aticaprant of any one of Embodiments 1-15, the amorphous form of aticaprant of any one of Embodiments 16-18, or a combination thereof, and (ii) instructions for treating major depressive disorder in a human patient having anhedonia.

The following Examples are set forth to aid in the understanding of the invention, and are not intended and should not be construed to limit in any way the invention set forth in the claims which follow thereafter.

| Abbreviations | |
|---|---|
| Acronym | Meaning |
| $^1$H NMR | proton nuclear magnetic resonance |
| CAN | acetonitrile |
| ATR | attenuated total reflectance |
| BDE | blow-down evaporation |
| ca. | approximately |
| CA(PEG)$_n$ | carboxy-PEG-amine (n = # ethylene glycol units) |
| CCD | charge coupled detector |
| DCM | dichloromethane |
| DMAc | N,N-dimethylacetamide |
| DMF | N,N-dimethylformamide |
| DMI | 1,3-dimethyl-2-imidazolidinone |
| DMPU | N,N'-dimethylpropyleneurea |
| DMSO | dimethyl sulfoxide |
| DSC | differential scanning calorimetry |
| DVS | dynamic vapor sorption |
| Eq | equivalents |
| EtOH | ethanol |
| FTIR | fourier transform infrared |
| GVS | gravimetric vapor sorption |
| HPLC | high performance liquid chromatography |
| IC | ion chromatography |
| ID | identification |
| IPA | 2-propanol |
| mDSC | modulated differential scanning calorimetry |
| MEK | methyl ethyl ketone (2-butanone) |
| MeOH | methanol |
| MIBK | methyl isobutyl ketone |

-continued

| Abbreviations | |
|---|---|
| Acronym | Meaning |
| N/A | not applicable |
| NBP | N-butyl-2-pyrrolidone |
| NMR | nuclear magnetic resonance |
| PLM | polarized light microscopy |
| PTFE | polytetrafluoroethylene |
| PMMA | polymethyl methacrylate |
| PVA | polyvinyl acrylate |
| PVP | polyvinylpyrrolidone |
| RH | relative humidity |
| RT | room temperature |
| SCXRD | single crystal x-ray diffraction |
| SEM | scanning electron microscope |
| SM | starting material |
| TBME | tert-butyl methyl ether |
| t-BuOH | tert-butanol |
| TFA | trifluoroacetic acid |
| TGA | thermal gravimetric analysis |
| THF | tetrahydrofuran |
| USP | United States pharmacopeia |
| vol | volumes |
| XRPD | x-ray powder diffraction |

Example 1: Instrument and Methodology Details

A. X-ray Powder Diffraction (XRPD)
Bruker AXS D8 Advance

XRPD diffractograms were collected on a Bruker D8 diffractometer using Cu Kα radiation (40 kV, 40 mA) and a θ-2θ goniometer fitted with a Ge monochromator. The incident beam passes through a 2.0 mm divergence slit followed by a 0.2 mm anti-scatter slit and knife edge. The diffracted beam passes through an 8.0 mm receiving slit with 2.5° Soller slits followed by the Lynxeye Detector. The software used for data collection and analysis was Diffrac Plus XRD Commander and Diffrac Plus EVA, respectively.

Samples were run under ambient conditions as flat plate specimens using powder as received. The sample was prepared on a polished, zero-background (510) silicon wafer by gently pressing onto the flat surface or packed into a cut cavity. The sample was rotated in its own plane.

The details of the standard Pharmorphix data collection method are:
 Angular range: 2 to 42° 2θ
 Step size: 0.05° 2θ
 Collection time: 0.5 s/step (total collection time: 6.40 min)

When required other methods for data collection are used with details as shown in Table 14.

TABLE 14

| Additional D8 XRPD methods 4 Minute Method | |
|---|---|
| Angular Range | 2 to 31° 2θ |
| Step Size | 0.06° 2θ |
| Time per Step | 0.5 s/step |

PANalytical Empyrean

XRPD diffractograms were collected on a PANalytical Empyrean diffractometer using Cu Kα radiation (45 kV, 40 mA) in transmission geometry. A 0.5° slit, 4 mm mask and 0.04 rad Soller slits with a focusing mirror were used on the incident beam. A PIXcel$^{3D}$ detector, placed on the diffracted beam, was fitted with a receiving slit and 0.04 rad Soller slits. The software used for data collection was X'Pert Data Collector using X'Pert Operator Interface. The data were analyzed and presented using Diffrac Plus EVA or High-Score Plus.

Samples were prepared and analyzed in either a metal or Millipore 96 well-plate in transmission mode. X-ray transparent film was used between the metal sheets on the metal well-plate and powders (approximately 1-2 mg) were used as received. The Millipore plate was used to isolate and analyze solids from suspensions by adding a small amount of suspension directly to the plate before filtration under a light vacuum.

The scan mode for the metal plate used the gonio scan axis, whereas a 2θ scan was utilized for the Millipore plate.

The details of the standard screening data collection method are:
 Angular range: 2.5 to 32.0° 2θ
 Step size: 0.0130° 2θ
 Collection time: 12.75 s/step (total collection time of 2.07 min)

The software used for data collection was X'Pert Data Collector and the data analyzed and presented using Diffrac Plus EVA.

B. Nuclear Magnetic Resonance (NMR)

$^1$H NMR spectra were collected on a Bruker 400 MHz instrument equipped with an auto-sampler and controlled by a DRX400 console. Samples were prepared in DMSO-d$_6$ solvent, unless otherwise stated. Automated experiments were acquired using ICON-NMR configuration within Topspin software, using standard Bruker-loaded experiments ($^1$H). Off-line analysis was performed using ACD Spectrus Processor.

C. Differential Scanning Calorimetry (DSC)
TA Instruments Q2000

DSC data were collected on a TA Instruments Q2000 equipped with a 50 position auto-sampler. Typically, 0.5-3 mg of each sample, in a pin-holed aluminum pan, was heated at 10° C./min from 25° C. to 275° C. A purge of dry nitrogen at 50 mL/min was maintained over the sample.

Modulated temperature DSC was carried out using an underlying heating rate of 2° C./min and temperature modulation parameters of ±0.636° C. (amplitude) every 60 seconds.

The instrument control software was Advantage for Q Series and Thermal Advantage and the data were analyzed using Universal Analysis or TRIOS.

TA Instruments Discovery DSC

DSC data were collected on a TA Instruments Discovery DSC equipped with a 50 position auto-sampler. Typically, 0.5-3 mg of each sample, in a pin-holed aluminum pan, was heated at 10° C./min from 25° C. to 275° C. A purge of dry nitrogen at 50 mL/min was maintained over the sample.

The instrument control software was TRIOS and the data were analyzed using TRIOS or Universal Analysis.

D. Thermo-Gravimetric Analysis (TGA)
TA Instruments Q500

TGA data were collected on a TA Instruments Q500 TGA, equipped with a 16 position auto-sampler. Typically, 1-5 mg of each sample was loaded onto a pre-tared aluminum DSC pan and heated at 10° C./min from ambient temperature to 350° C. A nitrogen purge at 60 mL/min was maintained over the sample.

The instrument control software was Advantage for Q Series and Thermal Advantage and the data were analyzed using Universal Analysis or TRIOS.
TA Instruments Discovery TGA TGA data were collected on a TA Instruments Discovery TGA, equipped with a 25 position auto-sampler. Typically, 1-5 mg of each sample was loaded onto a pre-tared aluminum DSC pan and heated at 10° C./min from ambient temperature to 350° C. A nitrogen purge at 25 mL/min was maintained over the sample.

The instrument control software was TRIOS and the data were analyzed using TRIOS or Universal Analysis.
E. Polarized Light Microscopy (PLM)
Leica LM/DM Polarized Light Microscope Samples were analyzed on a Leica LM/DM polarized light microscope with a digital video camera for image capture. A small amount of each sample was placed on a glass slide, with or without immersion oil, and covered with a glass slip. The sample was viewed with appropriate magnification and partially polarized light, coupled to a λ false-color filter. Images were captured using StudioCapture or Image ProPlus software.
Nikon LM/DM Polarized Light Microscope Samples were studied on a Nikon SMZ1500 polarized light microscope with a digital video camera connected to a DS Camera control unit DS-L2 for image capture. The sample was viewed with appropriate magnification and partially polarized light, coupled to a 2 false-color filter.
F. Scanning Electron Microscopy (SEM)

Data were collected on a Phenom Pro SEM. A small quantity of sample was mounted onto an aluminum stub using conducting double-sided adhesive tape. A thin layer of gold was applied using a sputter coater (20 mA, 120 s).
G. Gravimetric Vapor Sorption (GVS)

Sorption isotherms were obtained using a SMS DVS Intrinsic moisture sorption analyzer, controlled by DVS Intrinsic Control software. The sample temperature was maintained at 25° C. by the instrument controls. The humidity was controlled by mixing streams of dry and wet nitrogen, with a total flow rate of 200 mL/min. The relative humidity was measured by a calibrated Rotronic probe (dynamic range of 1.0-100% RH), located near the sample. The weight change, (mass relaxation) of the sample as a function of % RH was constantly monitored by a microbalance (accuracy ±0.005 mg).

Typically, 5-30 mg of sample was placed in a tared mesh stainless steel basket under ambient conditions. The sample was loaded and unloaded at 40% RH and 25° C. (typical room conditions). A moisture sorption isotherm was performed as outlined below (2 scans per complete cycle). The standard isotherm was performed at 25° C. at 10% RH intervals over a 0-90% RH range. Typically, a double cycle (4 scans) was carried out. Data analysis was carried out within Microsoft Excel using the DVS Analysis Suite. See, Table 15.

TABLE 15

| Method for SMS DVS Intrinsic experiments | |
| --- | --- |
| Parameter | Value |
| Adsorption - Scan 1 | 40-90 |
| Desorption, Adsorption-Scan 2 | 90-0, 0-40 |
| Intervals (% RH) | 10 |
| Number of Scans | 4 |
| Flow rate (ml/min) | 200 |
| Temperature (° C.) | 25 |

TABLE 15-continued

| Method for SMS DVS Intrinsic experiments | |
| --- | --- |
| Parameter | Value |
| Stability (° C./min) | 0.2 |
| Sorption Time (hours | 6 hour time out |
| Number of cycles | 2 |

The sample was recovered after completion of the isotherm and re-analyzed by XRPD.
H. Chemical Purity Determination by HPLC Purity analysis was performed on an Agilent HP1100/Infinity II 1260 series system equipped with a diode array detector and using OpenLAB software. The full method details are provided in Table 16.

TABLE 16

| HPLC method for chemical purity determinations | | |
| --- | --- | --- |
| Parameter | Value | |
| Type of method | Reverse phase with gradient elution | |
| Sample Preparation | 0.2 mg/ml in acetonitrile:water 1:1 | |
| Column | Supelco Ascentis Express C18 2.7 μm 100 × 4.6 mm | |
| Column Temperature (° C.) | 25 | |
| Injection (μL) | 5 | |
| Detection: Wavelength, Bandwidth (nm) | 255, 90 | |
| Flow Rate (ml/min) | 2 | |
| Phase A | 0.1% TFA in water | |
| Phase B | 0.085% TFA in acetonitrile | |
| | Time (min) | % Phase A | % Phase B |
| Timetable | 0 | 95 | 5 |
| | 6 | 5 | 95 |
| | 6.2 | 95 | 5 |
| | 8 | 95 | 5 |

I. Ion Chromatography (IC)

Data were collected on a Metrohm 930 Compact IC Flex with 858 Professional autosampler and 800 Dosino dosage unit monitor, using IC MagicNet software. Accurately weighed samples were prepared as stock solutions in a suitable solvent. Quantification was achieved by comparison with standard solutions of known concentration of the ion being analyzed. Analyses were performed in duplicate and an average of the values is given unless otherwise stated. See, Tables 17A and 17B.

TABLE 17A

| IC method for cation chromatography | |
| --- | --- |
| Parameter | Value |
| Type of method | Cation exchange |
| Column | Metrosep C 4-250 (4.0 × 250 mm) |
| Column Temperature (° C.) | Ambient |
| Injection (μL) | Various |
| Detection | Conductivity detector |
| Flow Rate (ml/min) | 0.9 |
| Eluent | 1.7 mM nitric acid 0.7 mM dipicolinic acid in a 5% acetone aqueous solution |

TABLE 17B

IC method for anion chromatography

| Parameter | Value |
| --- | --- |
| Type of method | Anion exchange |
| Column | Metrosep A Supp 5-150 (4.0 × 150 mm) |
| Column Temperature (° C.) | Ambient |
| Injection (μL) | Various |
| Detection | Conductivity detector |
| Flow Rate (mL/min) | 0.7 |
| Eluent | 3.2 mM sodium carbonate 1.0 mM sodium hydrogen carbonate in 5% acetoneaqueous solution |

J. Single Crystal X-Ray Diffraction (SCXRD)

Data were collected on a Rigaku Oxford Diffraction Supernova Dual Source, Cu at Zero, Atlas CCD diffractometer equipped with an Oxford Cryosystems Cobra cooling device. The data were collected using Cu Kα or Mo Kα radiation as stated in the experimental tables. Structures were solved and refined using the Bruker AXS SHELXTL suite or the OLEX crystallographic software. Full details can be found in the CIF. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter. A reference diffractogram for the crystal structure was generated as described in Macrae, "Mercury: Visualization and analysis of crystal structures," 2006, J. Appl. Cryst., Vol. 39, pp. 453-457.

K. Raman Spectroscopy

Data were collected on a Renishaw in Via Qontor. Instrument control, data analysis and presentation software was WIRE.

Method: excitation source, $\lambda_{ex}$=633 nm or 785 nm laser, attenuated appropriately to avoid sample degradation.

Raman shift range: 100-5000 cm$^{-1}$; Exposure time: 0.02-10 s; Accumulations: 1-3.

L. Fourier Transform Infrared (FTIR)

Data were collected on a Perkin-Elmer Spectrum One fitted with a universal

Attenuated Total Reflectance (ATR) sampling accessory from 4000-650 cm-1 over 16 scans. The data were collected using Spectrum software and processed using ACD Spectrus Processor.

Example 2—Techniques

A. Crystallization Techniques

For the investigation of crystalline forms, maturation experiments (or slurry ripening) were performed in various solvents or solvent mixtures and subjected to heat-cool cycles.

Maturation Chamber Procedure

Suspensions for maturation were placed in a platform shaker incubator (Heidolph Titramax/Incubator 1000 and subjected to a series of heat-cool cycles from ambient to approximately 50° C. This is achieved by switching the heating on or off every 4 hours. Shaking is maintained throughout.

Polar Bear Procedure

Suspensions were stirred in a Polar Bear (Cambridge Reactor Design) at 50° C. The samples were then cooled to 25° C. and stirred for a further 4 hours. After this time, the samples were heated back to 50° C. The cycle was then repeated.

Cooling Crystallization

Crystallizations were obtained by lowering the temperature of a clear solution.

Controlled Evaporation

Crystallizations were generated by controlled evaporation of clear, particulate free, solutions. At approximately constant temperature, the solvent was removed from the system, thereby increasing the solute concentration. The crystal nucleation and growth was obtained when some maximum supersaturation is reached.

Precipitation/Crystallization by Anti-Solvent Addition

Anti-solvent crystallization (or drown out crystallization) was used to precipitate material from a solution. The crystallization including adding a miscible anti-solvent to a solute solution, reducing the original solubility of the solute, increasing the supersaturation and thus, causing its precipitation.

Crystallization by Solvent Deposition or Solvent Layer Diffusion

Solvent diffusion crystallization was used to slowly precipitate material from a solution. The material was dissolved in an appropriate solvent in a vial and a miscible anti-solvent added very slowly to rest over the solvent layer. The vial was then closed.

The selected anti-solvent was miscible with the solvent at any proportion, and the solute was relatively insoluble in it. Additionally, a density gradient was required for the anti-solvent to gradually diffuse into the solvent layer, reducing the overall solubility and eventually resulting in crystallization of the material.

B. Thermal Techniques

Desolvation of Solvates/Hydrates (Upon Drying)

Various environmental conditions, such as temperature and pressure were used to desolvate aticaprant in solid-state hydrated or solvated phases.

C. Grinding Techniques

Grinding was used herein alone and via polymer-assisted grinding (POLAG). POLAG, an alternative to liquid-assisted grinding, is a mechanochemical method that uses polymers in association with grinding for promoting and/or accelerating mechanochemical reactions.

Planetary Mill Procedure: Aticaprant and the relevant polymer were placed in sample vials and two stainless steel grinding beads (3 mm diameter) were added. The mixtures were ground for 2 hours at 500 rpm using a planetary Fritsch Mill (Pulverisette 6) with an Automaxion adapter. After grinding all samples were initially analyzed by XRPD.

Example 3—Generation and Characterization of Amorphous Aticaprant

Both freeze drying and fast evaporation techniques were utilized to generate amorphous aticaprant.

A. Freeze Drying

Form III of aticaprant (20 mg) was weighed into 3 HPLC vials. Each vial was treated with 10 vol (250 μL) of the relevant solvent at 25° C. and shaken. The sample in t-BuOH was placed at 90° C. for a few seconds, where a solution was obtained. The solutions were filtered using a 0.45 μm PTFE membrane Acrodisc filter, before being flash frozen in an acetone/dry ice bath for 5 minutes. The samples were then freeze-dried overnight. The resulting solids were characterized by XRPD.

Form III was shown to be soluble in 70% THF/H₂O at RT (biphasic), and in t-BuOH at 90° C. Results are shown in Table 18.

TABLE 18

Results from amorphous generation

| Solvent | Solvent Amount | Observations | XRPD |
|---|---|---|---|
| t-BuOH | 250 µL/ 10 vol | Insoluble (soluble at 90° C.) | Amorphous |
| THF/H₂O (70%) | 250 µL/ 10 vol | Soluble, biphasic sol | Amorphous |

Figure 2:
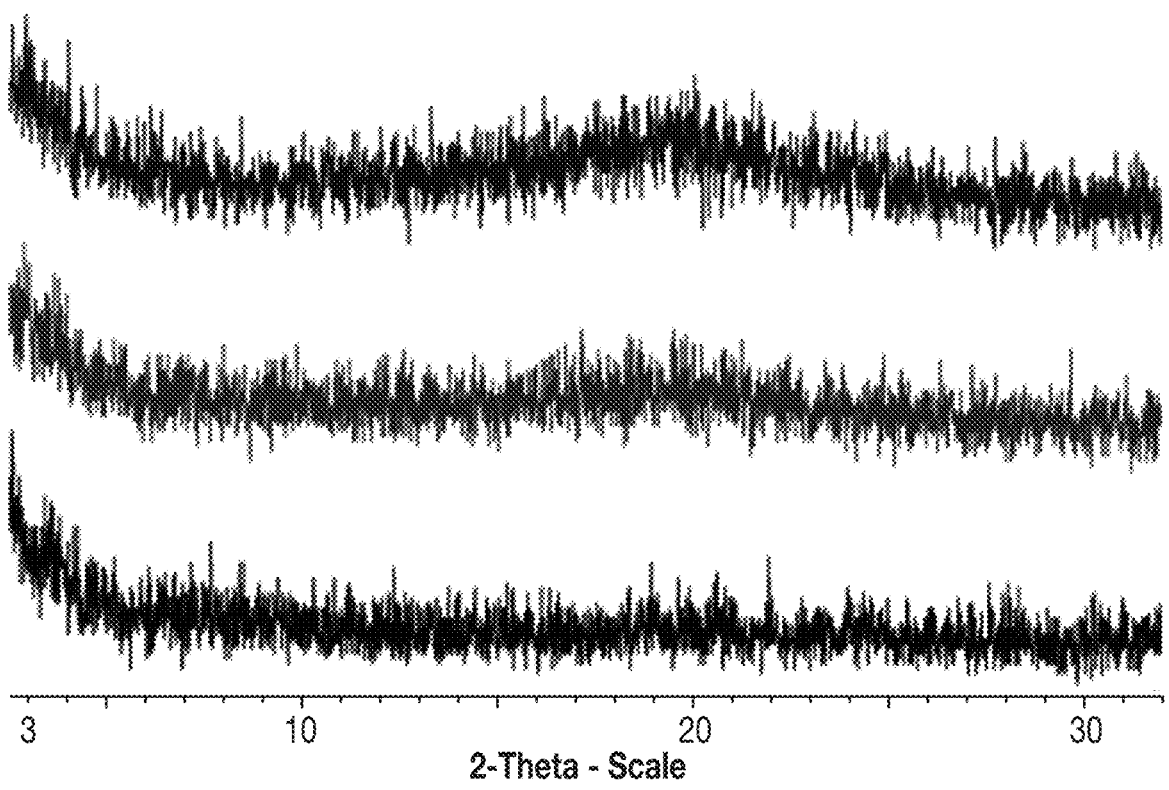
FIG. 2 are XRPD patterns of amorphous aticaprant. The top pattern results from 1,4-dioxane, the middle pattern results from t-butanol, and the bottom pattern results from THF/$H_2O$.

XRPD analysis showed that the freeze-drying method was successful at producing amorphous material from t-BuOH and 70% THF/H₂O. See, FIG. 2. ¹H NMR on the sample from THF/water showed the presence of residual THF (peaks too small to be integrated), and the glass transition temperature was found to be 56.8° C. See, the mDSC (FIG. 3) of amorphous aticaprant.

After static storage of amorphous aticaprant at 40° C./75% RH for 1 week, Form II was obtained.

B. Blow-Down Evaporation (BDE) Procedure

THF and acetone were used as solvents to probe BDE as a technique for generating amorphous aticaprant. Form III of aticaprant (30 mg) was dissolved in 5 vol. (150 µL) acetone at RT and shaken to obtain a clear solution. The solvent was removed by BDE for 40 mins using 60° C. N₂ at a flow rate of 30 L/min. This material was subsequently used for the polymorph screens at 5 and 50° C.

Fresh amorphous aticaprant was prepared for static storage at 40° C./75% RH for 1 week. Both solvents produced amorphous aticaprant. $T_g$ was determined to be 45.5° C. by mDSC. See, Table 19 for the characterization of amorphous aticaprant.

TABLE 19

Characterization of Amorphous Aticaprant

| | |
|---|---|
| ¹H-NMR | Residual acetone present (0.2 mol. eq.) |
| mDSC | mDSC carried out on sample Tg = 45.5° C. |
| HPLC Purity | 99.7% |
| DSC | GFA Class III |

Example 4—Polymorph Screens

A. Solubility Assessment

Form III of aticaprant (20 mg) was dispensed into amber HPLC vials with a magnetic stirrer bar. Each vial was treated with the relevant solvent (5 vol) at RT and stirred at 300 rpm for 10 mins. If suspensions were still observed, Form III of aticaprant (20 mg) was dispensed into amber HPLC vials (×49) with a magnetic stirrer bar. Each vial was treated with the relevant solvent (5 vol) at RT and stirred at 300 rpm for 10 mins. If suspensions were still observed, increasing volumes of the solvent were added until the material fully dissolved or until a maximum of 80 vol had been used (Table 20). All samples were heated to 50° C. and held for 1 hour. The samples were then cooled to 5° C. at a rate of 0.1° C./min and left to stir overnight. Any suspensions remaining at this point were subjected to maturation at RT/50° C. for 2 weeks.

Figure 13:
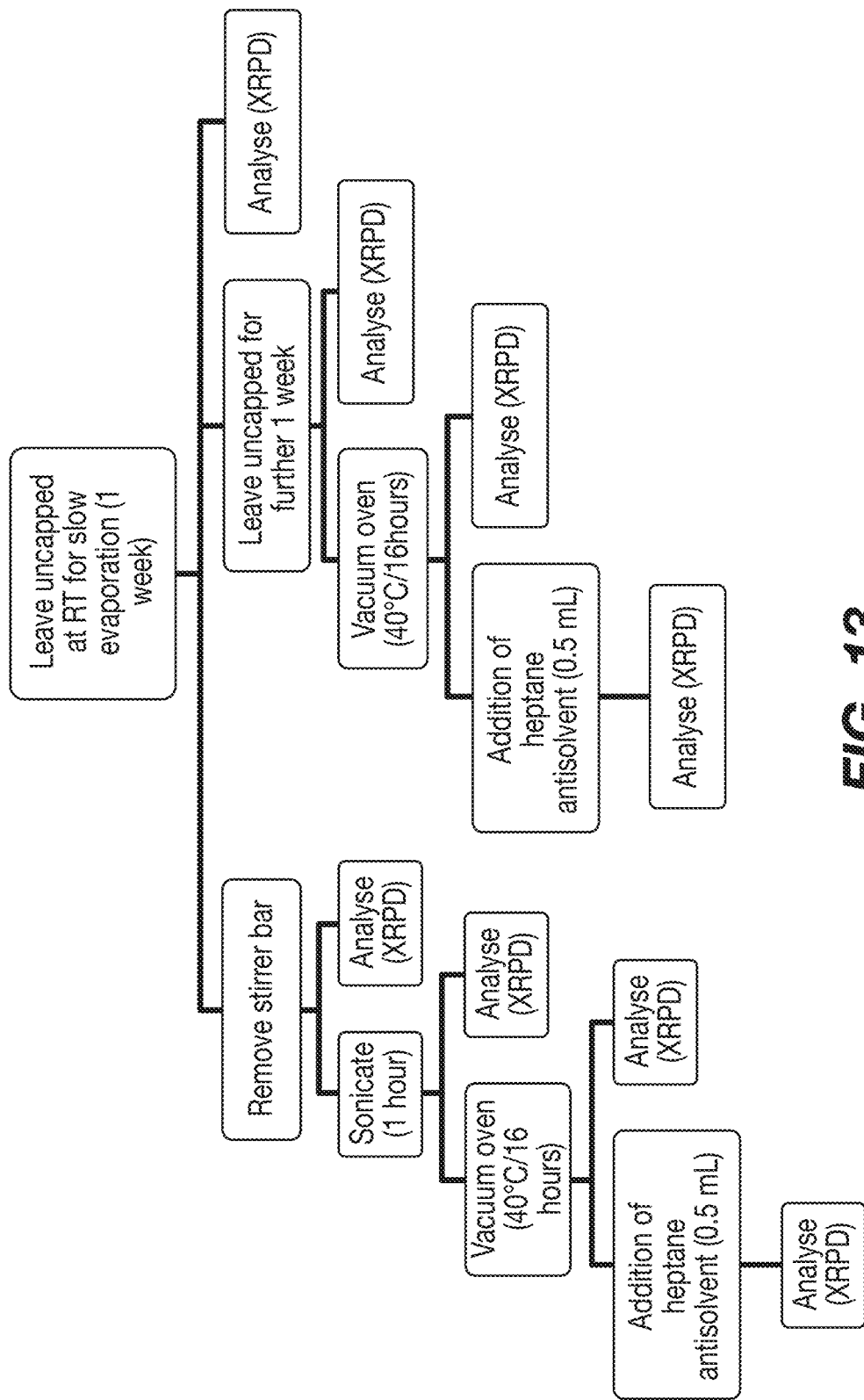
FIG. 13 is a schematic showing the decision tree for the treatment of gums/oils in the solubility screen.

Solutions remaining after 24 hours were allowed to evaporate to dryness, suspensions were isolated by filtration under positive pressure, and all solids were analyzed by XRPD. Gums or oils were further treated using the schematic of FIG. 13.

The results of the solubility assessment are shown in Table 20. Form III of aticaprant was obtained from water, DMSO (after maturation of the gum formed at 25/50° C. for 8 days), diethyl ether (crystalline), DCM (crystalline), heptane, 3-methyl-1-butanol, water/methanol (20%), nitromethane, chloroform (crystalline) and cyclohexane.

TABLE 20

Results of Solubility Assessment

| Solvent | Point of Crystallization/Treatment | XRPD |
|---|---|---|
| water | Slurry at-25° C./50° C. cycling (10 days) | Form III |
| acetonitrile | Slow evaporation (1 week), followed by sonication | Amorphous |
| isopropyl acetate | 1. Slow evaporation (1 week), 2. Sonication (1 hr), 3. Vac oven (40° C./16 hours) 4. Antisolvent (heptane) addition | Amorphous |
| DMSO | 1. Slow evaporation (2 weeks), vac oven 24 h at 40° C. 2. Slow evaporation 3. Maturation 25/50° C., 5 days 4. Sonication, ca. 1.5 h 5. n-Heptane addition, maturation 25/50° C., 2 days 6. Gummy white solid, matured 25/50° C./8 days | Form III |
| MIBK | Slow evaporation (1 week), sonication (1 hr) | Amorphous |
| heptane | Did not dissolve-25° C./50° C. cycling (10 days) | Form III |
| 3-methyl-1-butanol | Evaporation (2 w) | Form III |
| 20% water/MeOH | 10° C. cool and 1 hour hold | Form III |
| nitromethane | 10° C. cool and 1 hour hold | Form III |
| cyclohexane | Did not dissolve-25° C./50° C. cycling (10 days) | Form III |
| DMAc | 1. Slow evaporation (2 weeks), vac oven 24 h at 40° C. 2. Slow evaporation 3. Maturation 25/50° C., 8 days | Form III |

B. Low Temperature Polymorphism Screen

The low temperature polymorph screen was carried out using amorphous aticaprant at 5° C. Amorphous aticaprant (30 mg), generated by BDE in section "Blow-Down Evaporation (BDE) Procedure" noted above, was used. Each vial was treated with the solvent noted in Table 21 in a given volume to produce a slurry at 5° C. and stirred at 500 rpm for 10 mins. For clear solutions at 10 mins that converted to slurries, a small aliquot was taken and analyzed by XRPD. Any samples remaining as clear solutions were set aside and cooled to RT overnight, and later treated with antisolvent. Results of the low-temperature polymorph screen can be found in Table 21.

TABLE 21

Results from low-temperature, and subsequent antisolvent polymorph screen

| Solvent | Solvent (vol.) | Treatment | Form after 24 h | Form after 14 days |
|---|---|---|---|---|
| methanol | 10 | XRPD | Form III | Form III |
| 2-propanol | 10 | $H_2O$ antisolvent (250 µL) | Form III | Form III |
| 1-propanol | 5 | $H_2O$ antisolvent (2:1) | Form III | Form III |
| acetone | 5 | $H_2O$ antisolvent (5:1) Maturation 25/50° C. | Amorphous | Form III |
| isopropyl acetate | 10 | $H_2O$ antisolvent (2:1): Biphasic sol Vac oven 50° C. | Amorphous | Amorphous |
| TBME | 15 | $H_2O$ antisolvent (1:1): Biphasic sol Vac oven 50° C. | Amorphous | Amorphous |
| MEK | 5 | $H_2O$ antisolvent (5:1) | Form III | Form III |
| NBP | 5 | $H_2O$ antisolvent (5:1) Solvent removed in vac oven, 50° C. | Form III | Form III |
| MIBK | 5 | 1. $H_2O$ antisolvent (1:1) 2. Evaporation to dryness 3. Maturation 25/50° C. | Form II and Form III | Form II and Form III |
| DMF | 5 | $H_2O$ antisolvent (1:1) Maturation 25/50° C. | Amorphous | Form III |
| DMPU | 5 | $H_2O$ antisolvent (5:1) Maturation 25/50° C./4 days | Form III | Form III |
| 10% water/methanol | 40 | $H_2O$ antisolvent (1:1) Maturation 25/50° C./4 days | Form III | Form III |
| 5% water/EtOH | 15 | XRPD | Form III | Form III |
| 20% water/methanol | 40 | None | Form III | Form III |
| 10% water/IPA | 15 | XRPD | Form III | Form III |
| 10% water/ACN | 25 | $H_2O$ antisolvent (1:1) | Form III | Form III |
| pyridine | 5 | $H_2O$ antisolvent (5:1) Maturation 25/50° C./4 days | Form III | Form III |
| 1-methylpyrrolidine | 5 | $H_2O$ antisolvent (5:1) | Form III | Form III |
| DMAc | 5 | $H_2O$ antisolvent (1:1) Maturation 25/50° C./4 days | Form III | Form III |

Most of the samples produced clear solutions within ten minutes, and remained as solutions after 24 h. Samples forming turbid solutions after ten minutes formed suspensions within an hour. Form III was obtained from 1-propanol, 2-propanol, acetone, MEK, NBP, DMF, DMI, DMPU, 10% water/methanol, 5% water/EtOH, 20% water/methanol, 10% water/IPA, 10% water/ACN, pyridine, 1-methylpyrrolidine and DMAc.

The samples remaining as solutions after 14 days were left to equilibrate at RT, and treated with water as antisolvent, to induce precipitation. See, Table 21. Samples were treated in antisolvent/solvent ratios starting at 1:1, increasing to 2:1, 3:1 or 5:1, until precipitation occurred. After 3 h, any solids/suspensions were isolated by filtration on a Millipore well plate and analyzed by XRPD.

Of the samples treated with antisolvent, Form III was obtained with 1-propanol and 2-propanol, acetone, MEK, NBP, DMF, DMI, DMPU, 10% water/methanol, 10% water/ACN, pyridine, 1-methylpyrrolidine and DMAc.

C. High Temperature Polymorph Screen

The high temperature polymorph screen was carried out using amorphous aticaprant at 50° C. The procedure was performed as described in the low temperature screen, except samples were initially shaken at 50° C. for 10 mins. Initial observations were noted, and again at 1 h and 24 h timepoints. If clear solutions at 10 mins converted to slurries, an aliquot was taken and analyzed by XRPD. After 7 days, suspensions were re-analyzed by XRPD. Any samples remaining as clear solutions after 24 h were cooled to RT overnight, and later treated with antisolvent. Results of the high-temperature polymorph screen can be found in Table 22.

TABLE 22

Results from high-temperature, and subsequent antisolvent polymorph screen

| Solvent | Initial solvent (vol.) | Treatment | Form after 24 hours | Form after 14 days |
|---|---|---|---|---|
| water | 10 | XRPD | Amorphous | Amorphous |
| acetone | 5 | Heptane 5:1 | Form III | Form III |
| ethyl acetate | 10 | Heptane 5:1 | Form I | Form I |
| acetonitrile | 5 | Heptane 3:1 | Form III | Form III |
| isopropyl acetate | 5 | Heptane 3:1 | Form III | Form III |
| MEK | 5 | Heptane 5:1 | Form III | Form III |
| NBP | 5 | Heptane 5:1<br>1. Evap.<br>2. Maturation 25/50° C. | Form III | Form III |
| diethyl ether | 5 | Heptane 1:1 | Form I | Form I |
| MIBK | 5 | Heptane 5:1 | Form III | Form III |
| DMF | 5 | Heptane 2:1<br>1. Evap.<br>2. Maturation 25° C./50° C. | Form III | Form III |
| DMI | 5 | Heptane 2:1<br>1. Evaporation to dryness<br>2. Maturation 25/50° C.<br>3. Sonication ca. 1 h<br>4. Vac oven: 50° C./6 h | Amorphous | Amorphous |
| 2-methyl THF | 5 | Heptane 5:1 | Form III | Form III |
| 1-methoxy-2-propanol | 5 | Heptane 5:1<br>1. Evaporation to dryness<br>2. Maturation 25/50° C. | Form III | Form III |
| 3-methyl-1-butanol | 5 | Heptane 5:1<br>1. Evap. to dryness<br>2. Maturation 25/50° C. | Form III | Form III |
| 10% water/methanol | 10 | Heptane 5:1<br>1. Evaporation to dryness<br>2. Maturation 25/50° C. | Form III | Form III |
| 20% water/methanol | 10 | 1. Heptane 1:1<br>2. XRPD: repeat analysis after 5 days | Amorphous | Form III |
| 10% water/EtOH | 5 | Heptane 5:1 slow evap. | Form III | Form III |
| 10% water/ACN | 5 | Heptane 3:1 | Form III | Form III |
| PEG 400 | 5 | Heptane 5:1<br>1. Evap. to dryness<br>2. Maturation 25/50° C. | Mixture Form II/Form III | Mixture Form II/Form III |
| sulfolane | 5 | Heptane 5:1<br>1. Evaporation to dryness<br>2. Maturation 25/50° C.<br>3. Sonication ca. 1 h<br>4. Vac oven: 50° C./6 h | Amorphous | Amorphous |
| 1-pentanol | 5 | Evaporation to dryness | Form III | Form III |
| formic acid | 5 | Heptane 5:1<br>1. Evaporation to dryness<br>2. Maturation 25/50° C.<br>3. Sonication ca. 1 h<br>4. Vac oven: 50° C./6 h | Amorphous | Amorphous |
| DMAc | 5 | Heptane 5:1<br>1. Evaporation to dryness<br>2. Maturation 25/50° C.<br>3. Sonication ca. 1 h<br>4. Vac oven: 50° C./2 d h<br>5. 150 µL H₂O added<br>6. Maturation 25/50° C., 5 days | Amorphous | Amorphous |

The samples remaining as solutions after 7 days at 50° C. were cooled to RT, and treated with n-heptane. The samples were treated initially in a 1:1 antisolvent/solvent ratio, observations made and again after ten mins stirring (300 rpm/10 mins). Additional volumes of antisolvent were added until a precipitate formed. If a thin white suspension was obtained, or poor recovery after filtering was estimated, additional antisolvent was also added. Further observations were noted after 3 and 16 h, and aliquots of the suspensions were taken and analyzed by XRPD. Crystallization of gums that formed were made by further treatment as detailed in Table 22. The results of the antisolvent addition can also be found in Table 22. Form III was obtained from antisolvent addition of heptane to a number of solvent systems.

D. Temperature Cycling Polymorph Screen

Temperature cycling screen (25/50° C.) was carried out on amorphous aticaprant. Samples were treated with the solvent (2.5-5 vol, depending on solubility) in Table 23. Initial observations were made before the samples were placed on a platform shaker incubator programmed at 4 h cycles at 25/50° C. Observations were made after one day and 7 days, and any solids were analyzed by XRPD. Samples remaining as solutions were treated with cold antisolvent (either n-heptane or water), before being placed back in the maturation chamber.

Similar to the previous two screens, most samples produced solutions on addition of solvent, and remained as solutions after 7 days. Suspensions were observed in the samples with heptane and 20% water/methanol, and gums were formed in the samples with water and 10% water/acetone. The suspension in heptane was shown to be Form III after 24 h, remaining Form III after 7 days. The remaining samples formed solutions and were treated with antisolvent.

The samples that formed solutions in the temperature cycling screen were used treated with antisolvent-either water or heptane in a reverse-antisolvent screen.

Solutions were treated with either water or n-heptane as antisolvent, depending on solvent miscibility, in a 5:1 antisolvent: solvent ratio. Vials containing the relevant antisolvent in the given amount were prepared and placed in the fridge for ca. 2 h. Solutions from the maturation screen were kept at RT for ca. 4 h before being added to the antisolvent samples. Aliquots of the solids were taken and analyzed by XRPD. See, Table 23.

TABLE 23

Results from temperature-cycling polymorph, and subsequent reverse-antisolvent screen

| Solvent | Solvent Amount | Anti-solvent/ amount | Further Treatment | XRPD |
|---|---|---|---|---|
| water | 150 μL/5 vol | N/A | N/A | Form II |
| methanol | 75 μL/2.5 vol | water/375 μL | 25/50° C. 2 days | Form II |
| ethanol | 75 μL/2.5 vol | water/375 μL | 25/50° C. 2 days | Form II |
| 2-propanol | 300 μL/10 vol | water/375 μL | 25/50° C. 2 days | Form II |
| 1-propanol | 75 μL/2.5 vol | water/375 μL | 25/50° C. 2 days | Form II |
| TBME | 75 μL/2.5 vol | heptane/375 μL | Amorphous | Amorphous |
| DMSO | 75 μL/2.5 vol | water/375 μL | 1. 25/50° C. 2. Sonication 3 h | Amorphous |
| t-BuOH/water (1:1) | 75 μL/2.5 vol | N/A | 25/50° C. overnight | Form III |
| 10% water/methanol | 75 μL/2.5 vol | water/375 μL | 25/50° C. overnight | Form II |
| 10% water/acetone | 75 μL/2.5 vol | N/A | N/A | Form II/ Form III |
| PEG 400 | 75 μL/2.5 vol | water/375 μL | 1. 25/50° C., 2 days 2. Sonication 3 h | Amorphous |
| pyridine | 75 μL/2.5 vol | water/375 μL | 25/50° C. 2 days | Form III |
| 1-pentanol | 75 μL/2.5 vol | water/375 μL | Lid removed for evaporation/solid after 2 weeks | Form III |

E. Solvent Deposition (Solvent Layer Diffusion) Screen

Stock solutions of Form III were prepared. See, Table 24.

TABLE 24

Stock solutions of Form III of aticaprant in DMSO and t-BuOH

| Solvent | Amount (mg) | Amount Solvent |
|---|---|---|
| DMSO | 90 | 1.2 mL (13.3 vol) |
| t-BuOH | 30 | 300 (10 vol)/50° C. |

The solutions were then split into the relevant number of vials to give 30 mg per HPLC vial. Samples in DMSO and t-BuOH were placed in the freezer for ca. 1 h, after which were removed and treated with the relevant antisolvent in 5:1 antisolvent/solvent ratio. The antisolvent was added slowly to the frozen solution. Samples were then left to stand at RT. The results of the solvent deposition screen can be found in Table 25.

TABLE 25

Results from solvent deposition screen

| Solvent | Antisolvent/ Amount Deposited | Further Treatment | XPRD |
|---|---|---|---|
| DMSO | Water/1.5 mL | N/A | Form II |
| t-BuOH | cyclohexane | Refrigerator/6 days Lid removed for evaporation/6 days | Form II |

Solutions that had not produced solids after 6 days were removed from the refrigerator and lids were removed to evaporate the solvent. A solid was also produced in the sample in t-BuOH/cyclohexane after being left to evaporate for 6 days, shown to be Form II by XRPD. The t-BuOH sample was isolated via vacuum filtration, and left to dry for 2 h under vacuum. After this time, it was covered and left overnight.

F. Solvent Interfacial Crystallization Screen

Solvent interfacial screening was carried out by utilizing immiscible solvent/antisolvent combinations. Stock solutions of Form III of aticaprant were initially made. See, Table 26. The solutions were then split into vials to give 30 mg per vial. The samples were treated with the relevant antisolvent in 5:1 antisolvent/solvent ratio. Samples were then left to stand at RT. Samples remaining as solutions were placed in the refrigerator, and those producing solids were analyzed by XRPD.

TABLE 26

Details of stock solutions for the interfacial crystallization screens

| Solvent | Amount (mg) | Amount Solvent |
|---|---|---|
| MEK | 30 | 150 μL (5 vol) |
| t-BuOH | 60 | 600 μL (10 vol)/50° C. |
| 2-Methyl-THF | 30 | 150 μL (5 vol) |

The results of the solvent interfacial crystallization screens are shown in Table 27. In the t-BuOH/water system, a white suspension consisting of a gummy solid was formed shortly after addition of the antisolvent to the frozen t-BuOH. Maturation of the gum at RT/50° C. produced a white solid, which was found to be Form II after analysis by XRPD. Form II was also produced from the systems in MEK/water and 2-methyl THF, producing gums initially and yielding Form II after maturation.

TABLE 27

Results from interfacial crystallization screen

| Solvent | Antisolvent/ Deposited | Further Treatment | XPRD |
| --- | --- | --- | --- |
| t-BuOH | Water/1.5 mL | White solid | Form II |
| MEK | Water/750 μL | Refrigerator/6 days evaporation maturation RT/50° C./4 days | Form II |
| 2-methyl THF | Water/750 μL | Refrigerator/6 days evaporation Maturation RT/50° C./4 days | Form II |

K. Characterization of Form I, Form II, and Form III

Form I

Form I was obtained in the screens from ethyl acetate and MEK (both through solvent evaporation). It also was obtained from addition of heptane antisolvent to solutions in ethyl acetate and diethyl ether. The sample from the solubility assessment in ethyl acetate was isolated and characterized by XRPD, $^1$H NMR, and DSC (FIG. 7), and static storage at elevated temperature and humidity. The results are shown Table 30.

TABLE 30

Characterization of Form I

| $^1$H NMR | Matches structure ~0.1 mol. eq. ethyl acetate |
| --- | --- |
| DSC | Broad endotherm, onset 92.9° C. (57.4 J/g) |
| 40°C/75% RH 1 week | Form I |

DSC shows a broad endotherm, at 92.9° C. (57.4 J/g). After static storage, the sample was shown to remain as Form I. These findings show that Form I is likely an anhydrous form, which remains stable after storage at elevated temperature and humidity.

Form II

As noted above, Form II was obtained from the static storage of amorphous Aticaprant for 1 week at 40° C./75% RH, and was also observed several times in the screens from amorphous. Form II is anhydrous, and exhibits low hygroscopicity, and remains stable through both GVS analysis and static storage at elevated temperature and humidity conditions (40° C./75% RH and 25° C./97% RH).

Form III

Form III exhibits desirable solid-state characteristics and appears to be the most stable form. In addition, it is readily accessible from a number of solvents (including solutions of methanol, 20% methanol/water, 10% water/IPA and 5% water/ethanol), crystallizing at 5° C. Characterization was performed on Form III and the results are shown in Table 31.

TABLE 31

Characterization data for Form III

| XRPD | Crystalline |
| --- | --- |
| $^1$H-NMR | Consistent with proposed structure |
| HPLC Purity | 99.3% |
| IC | No cations/anion present |
| DSC | Endo. 121.0° C., 75 J/g. Degradation not observed |
| PLM | Small needles |
| TGA | No weight loss observed before degradation. Degradation onset ~250° C. |
| GVS | 0.4% max uptake at 90% RH No hysteresis observed XRPD unchanged after GVS |

Figure 5:
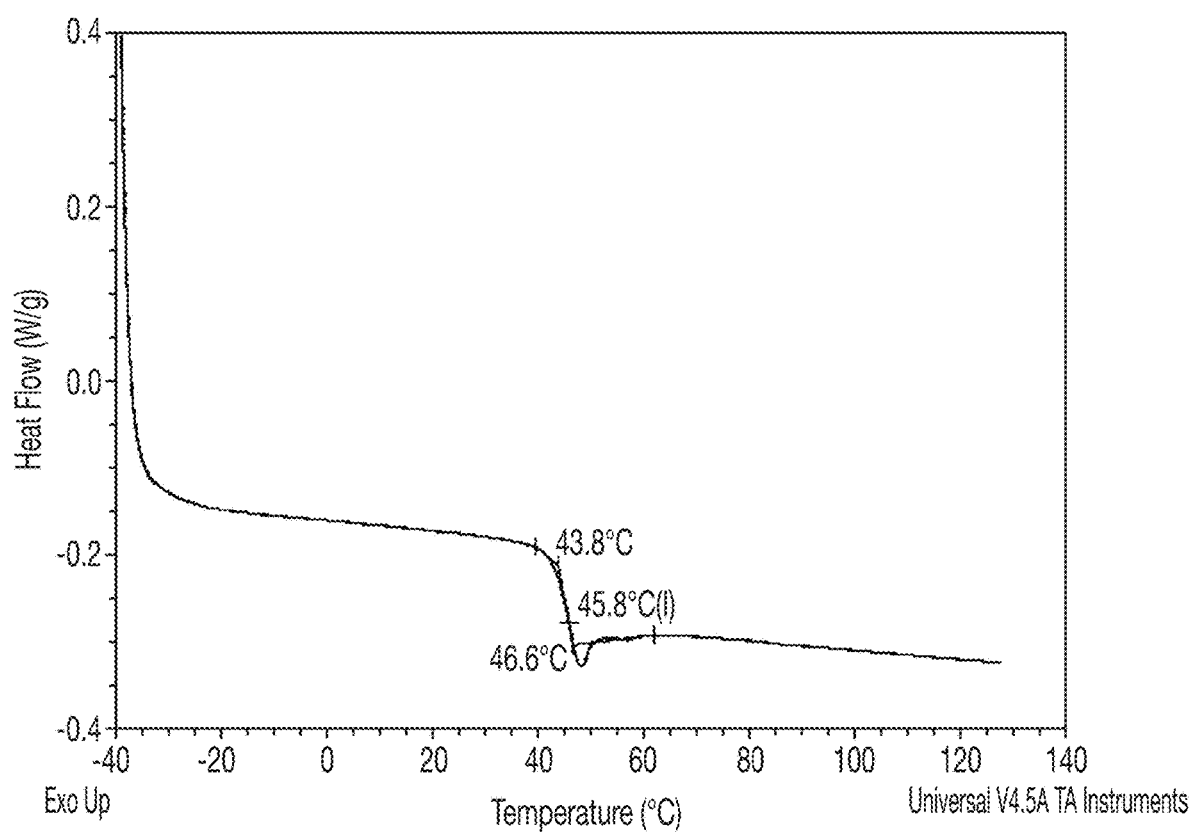
FIG. 5 is the DSC thermogram of the sample from FIG. 3 heated from −40 to 131° C./10° C./min.

Form III of aticaprant was found to be crystalline by XRPD. $^1$H NMR showed that the material was consistent with the proposed structure, with the presence of residual ethyl acetate. Ion chromatography showed that there were no cations/anions present, and HPLC showed 99.8% purity. The DSC (heating from 20 to 131° C. at 10° C./min) showed a peak temperature at 121° C. See, FIG. 12. Cycling of the amorphous form over two cycles (cycle 1=cooling from 131 to −40° C.; cycle 2=heating from −40° to 131° C. at 10° C./min) resulted in an annealed glass. See, FIG. 5.

Example 5—Thermodynamic Stability Relationships

A. Competitive Slurries

Competitive slurrying experiments were carried out with Form I, Form II and Form III to determine the relative order of stability. Slurrying experiments were carried out in six different solvent systems 5 and 50° C.

B. Preparation of Saturated Solutions

Saturated solutions of Form III were prepared in different solvent systems. See, Table 32. Each vial was filled with the relevant solvent (1.5 mL in each) and placed to equilibrate at the relevant temperature. After this time, small spatulas of the solid were added until the solid no longer dissolved. Samples were left to stir at 5° C. and 50° C. for ca. 2 weeks or longer as noted.

TABLE 32

Solvents

| acetonitrile |
| --- |
| 20% MeOH/H$_2$O |
| 2-propanol |
| isopropyl acetate |
| cyclohexane |
| Me-THF/60% heptane |

C. Preparation of a Mixture of Forms I and II

Form III (180 mg) and Form II (180 mg) were combined into a 4 mL vial. The sample was placed on a turbula blender for 30 mins, after which a small sample was taken and analyzed by XRPD to confirm a mixture. 10 mg of this mixture was weighed and a mixture of Form I and Form II was instead used as seeds in the competitive slurries. To each vial was added the mixture of Forms I and II (7 mg). See, Table 33.

TABLE 33

Competitive slurry experiments of Forms I, II and III

| | Temperature | | | | | |
|---|---|---|---|---|---|---|
| | 5° C. | | | 50° C. | | |
| Solvent | ca. 15 hours | 7 days | 18 days | 56 days | ca. 15 hours | 7 days | 18 days |
| 2-propanol | Cryst. | Form III | N/A | N/A | Form III/ Form II | Form III/ Form II | Form III |
| isopropyl acetate | Form III | Form III | N/A | N/A | Form III | Form III | N/A |
| cyclohexane | Form II/ Form III | Form II/ Form III | Form II/ Form III | Form III | Form III | Form III | N/A |
| Me-THF/ 60% heptane | Form III | Form III | N/A | N/A | Form III | Form III | N/A |

After 15 h, several of the samples converted to Form III. After 15 days, most of the samples converted to Form III, and after 56 days all samples had converted to Form III (samples in 20% MeOH/H$_2$O and cyclohexane (both at 5° C.) took longer to convert). This indicates that Form III is the most stable form at these conditions.

Example 6—Scale Up of Form I

A. Route 1—Precipitation from Ethyl Acetate/n-Heptane (0.5 g) Solution

Form III of aticaprant (0.5 g) was weighed into a large vial. The solid was dissolved in ethyl acetate (2.5 mL/5 vol). The solution was left to evaporate (vial lid loosened) overnight. The next morning, a solution remained. The sample was placed in the vacuum oven for ca. 1 h to further concentrate the solution. After this time, a white precipitate had begun to form. The suspension was left at RT overnight, after which a white solid was obtained. The solid was placed in a vacuum oven at 50° C. to remove any residual ethyl acetate for ca. 2.5 h, before re-analyzing by XRPD. The initial suspension was found to be Form I. This converted to Form III after drying in a vacuum oven.

B. Route 2—Evaporation of Ethyl Acetate (0.5 g) Solution

The sample from route 1 was redissolved in ethyl acetate (volume reduced to 2 mL). The sample was left uncapped, and a white precipitate was observed the next day. The sample was placed to dry in the vacuum oven for 3 days. The solid was determined to be Form III.

C. Route 3—Heptane Antisolvent Addition to Diethyl Ether (0.5 g) Solution

Form III (0.5 g) was dissolved in ethyl acetate (2.5 mL/5 vol) in a large vial. The solution was left to evaporate (vial lid removed) overnight. The next morning, a gum had formed, with a small amount of white solid growing in the gum. An aliquot of the solid was taken and analyzed by XRPD. After 24 h, the sample had turned completely solid, with very fine needles having grown. The solid was found to be a mixture of Forms II and III.

D. Routes 4-8—Heptane Antisolvent Addition to Diethyl Ether (100 mg) Solution

Smaller scale experiments were performed to re-prepare Form I. Different sized vials at different temperatures were utilized. Form III (100 mg) was added placed into five vials, and to it was added ethyl acetate (500 µL), whereby the solid dissolved. Each vial was placed at the relevant conditions, with the vial lid removed, unless otherwise specified in Table 34. Once a solid was observed, a small sample was taken and analyzed by XRPD.

TABLE 34

Analysis of solids from routes 4-8

| Vial Type | Temp (° C.) | Details | XRPD |
|---|---|---|---|
| HPLC | 5 | Lid removed, sample placed on polar bear | Form III |
| HPLC | 40 | Lid loosened, sample placed on polar bear | Form III |
| 4 mL | 5 | Lid removed, sample placed on polar bear | Form II |
| 4 mL | 40 | Lid removed, sample placed in oven | Form I/Form III |
| 4 mL | 50 | Lid removed, sample placed in vac oven | Form I/Form III |

Example 7—Scale Up of Form II (1 g Scale)

Form III (1 g) was weighed into a 50 mL Duran bottle. The solid was dissolved in DMSO (13.3 mL/13.3 vol), and the solution was placed in the freezer for ca. 30 mins. To the frozen solution was slowly added water (added around sides of bottle with rotation to minimize perturbation of the solid, in 10 mL aliquots), until a total of 50 mL water had been added. A white suspension was formed on top of the frozen solvent layer almost immediately. The suspension was left to stand for four days. After this time, the sample appeared more uniform, (no longer two layers), slight white ppt on top, and gummy solid on bottom of container. The sample was placed for maturation overnight (25/50° C.-4 h cycles). The next morning, solid was observed to be stuck around the sides of the container, which were loosened/broken up with a spatula. A small sample was taken and analyzed by XRPD. Amorphous content was still evident by XRPD, and so the sample was placed back in the maturation chamber for an additional day. After this time, improved crystallinity was observed, and the sample was isolated by vacuum filtration/drying. The method described above was successful in preparing Form II at large scale. See, Table 35.

TABLE 35

Scale up of Form II

| Details | XRPD |
|---|---|
| After storage in maturation chamber | Form II + amorphous |
| After additional 1 day maturation | Form II |

Figure 10:
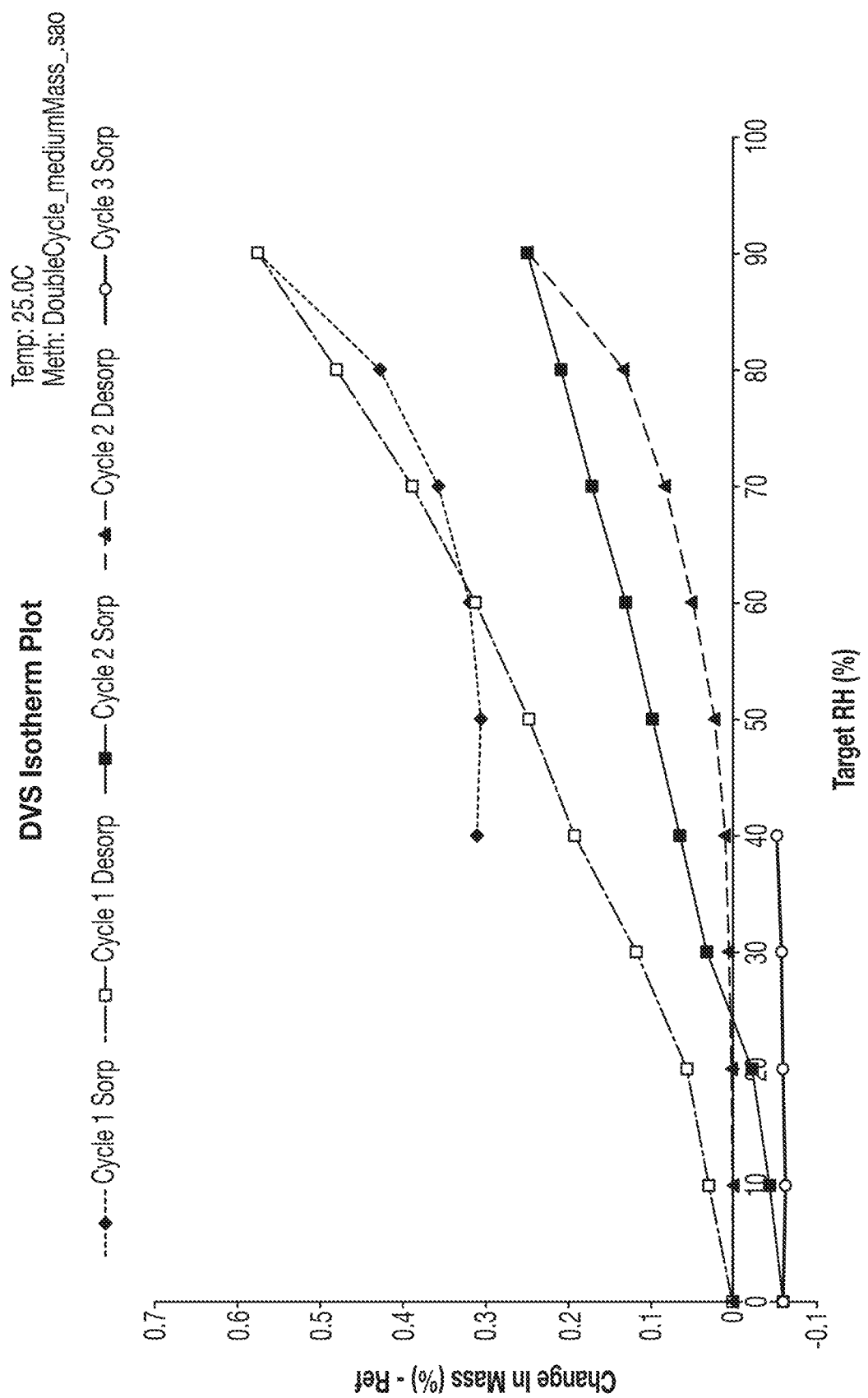
FIG. 10 is the gravimetric vapor sorption (GVS) isotherm plot of crystalline Form II of aticaprant (1 g scale).
Figure 11:
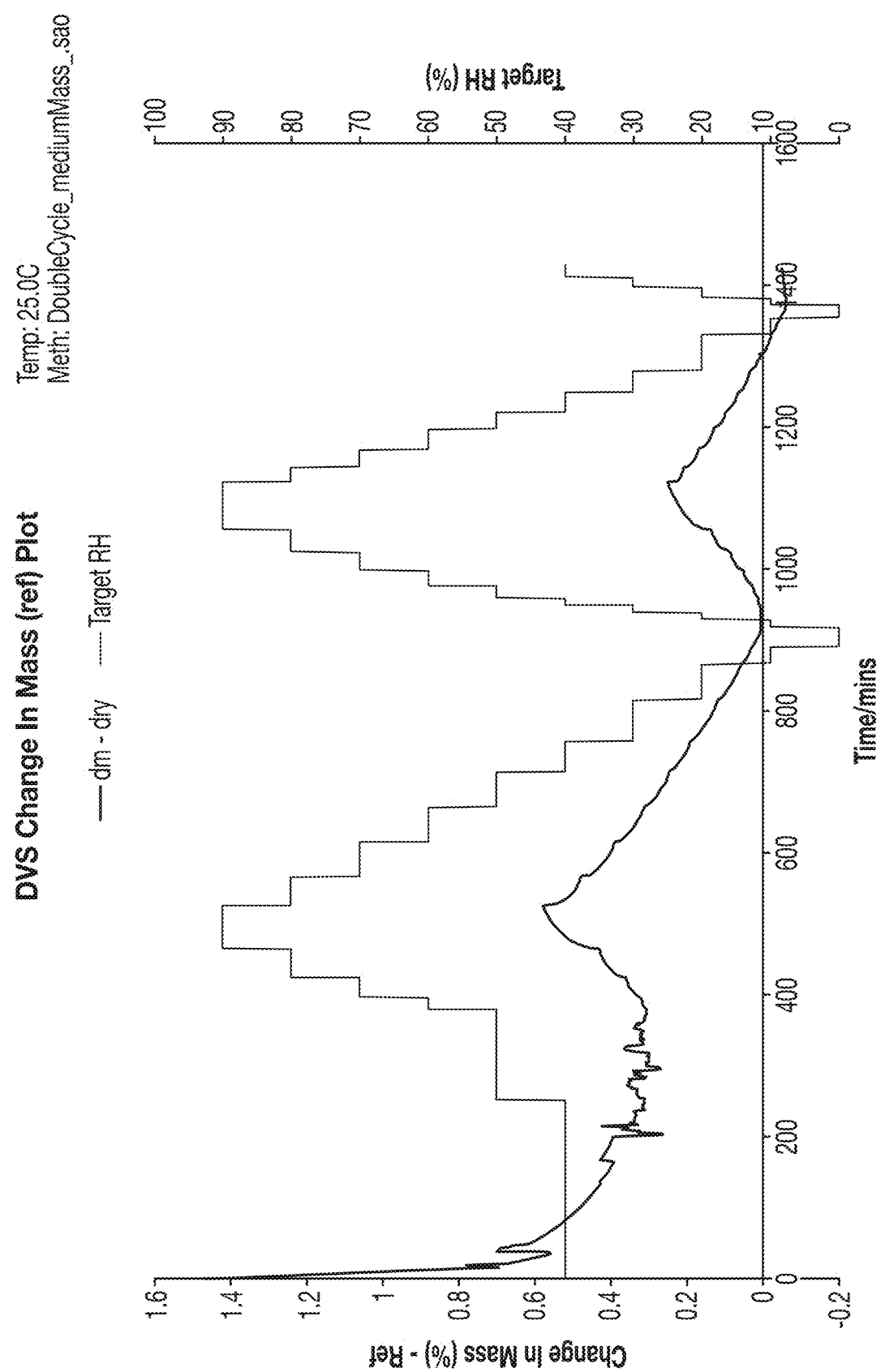
FIG. 11 is the GVS kinetics plot of crystalline Form II of aticaprant (1 g scale).

Form II was successfully scaled up (1 g) from solvent layer diffusion of water/DMSO, and was found to be anhydrous and exhibit low hygroscopicity. The sample remained as Form II post-GVS analysis. See, FIGS. 10 and 11. Large agglomerates are present comprised of smaller particles (<10 µm in size), as well as the presence of plates in the agglomerates (ca. 60 µm in length), and larger, ridged particles (~120 µm in length). Form II remained stable after static storage at elevated temperature and humidity conditions for 1 week.

$^1$H NMR of the isolated solid showed the presence of residual DMSO (0.08 mol. eq). TGA showed a small mass loss ambient—108° C. (0.95%/~0.05 mol. eq. DMSO), along with additional mass loss from 108-255° C., attributed to the onset of decomposition onset. The XRPD is shown in FIG. 8. DSC analysis showed an endotherm at 74.7° C. (4.7 J/g), overlapping with a second, sharper endotherm at 96.2° C. (onset, 51.3 J/g). See, FIG. 9. GVS analysis showed that Form II is slightly hygroscopic. A mass uptake of 0.26% is observed from 40-90% RH in the first cycles, with a mass loss of 0.57%. Similar mass water uptake (0.25%) is observed in the second sorption cycle, with all the water being lost again in the second desorption cycle, with a slight hysteresis observed. See, FIGS. 10-11. XRPD analysis post-GVS shows the sample to remain as Form II. HPLC analysis shows a purity of 99.7%. Microscopy analysis by SEM/PLM shows the presence of irregular particles. Particle size ranges from <10 μm and up to ca. 200 μm. Large agglomerates are present comprised of smaller particles (<10 μm in size), plates also present in the agglomerates (ca. 60 μm in length), as well as larger ridged particles (~120 μm in length). Static storage at elevated temperature and humidity conditions (40° C./75% RH and 25° C./97% RH) shows the sample to remain as Form II. See, Table 36.

TABLE 36

Characterization of Form II, prepared at 1 g scale

| | |
|---|---|
| $^1$H NMR | Residual DMSO (0.08 mol. eq) |
| TGA | 0.95% mass loss observed ambient −108° C.; 1.08% mass loss observed 108-255° C. (approximate decomposition onset) |
| DSC | Endotherm onset 74.7° C. (4.7 J/g), overlapping event with second sharper endotherm at 96.2° (onset, 51.3 J/g) |
| GVS | Sample exhibits low hygroscopicity. Mass uptake of 0.26% is observed from 40-90% RH, and a mass loss of 0.57% is observed on the first desorption cycle. A decreased % mass water uptake (0.25%) is observed in the second sorption cycle, with all the water being lost again in the second desorption cycle, with a slight hysteresis observed. XRPD post-GVS: Form II |
| HPLC | 99.6% |
| PLM | Irregular particles, up to 200 μm in width |
| SEM | Particle shape: irregular. Particles size range <10 μm to ca. 150 μm. Large agglomerates present comprised of smaller particles (<10 μm in size), plates also present in the agglomerates (ca. 60 μm in length). Larger ridged particles (~120 μm in length). |
| Static Storage (10 days) | 40° C./75% RH Form II<br>25° C./97% RH Form II |

Example 8

This was a multi-center, placebo-controlled, randomized, double-blind study in subjects with MDD who have had an inadequate response to SSRI/SNRI treatment. Aticaprant was evaluated as an adjunctive therapy; therefore, eligible subjects were maintained on their SSRI/SNRI treatment without change throughout the study. At least 50% of recruited subjects had to be anhedonic (as measured by SHAPS total score≥20).

A. Objectives

The primary objective was to evaluate the efficacy of aticaprant compared to placebo when administered as adjunctive treatment in subjects with MDD partially responsive to SSRI/SNRI treatment in terms of reduction of symptoms of depression, as assessed by the change from baseline on the MADRS in non-responders during the placebo lead-in period.

The secondary objectives are:
i. To evaluate the efficacy of aticaprant compared to placebo when administered as adjunctive treatment in subjects with MDD partially responsive to SSRI/SNRI treatment in terms of reduction of symptoms of depression, as assessed by the change from baseline on the MADRS in both responders and non-responders during the placebo lead-in period.
ii. To investigate the overall safety and tolerability of treatment with adjunctive aticaprant in subjects with MDD when used in combination with a SSRI or SNRI.
iii. To investigate the effect of aticaprant versus placebo on depression related anhedonia as assessed by the SHAPS.
iv. To investigate the effect of aticaprant on symptoms of depression using the Clinical Global Impression-Severity (CGI-S), the patient reported Symptoms of Major Depressive Disorder Scale (SMDDS) and the self-assessment of treatment experience (SATE).
V. To investigate the effect of aticaprant on symptoms of anxiety using the HAM-A and on core symptoms of anxiety using the HAM-A6 subscale.
vi. To assess the plasma PK of aticaprant in subjects with MDD and explore its relationship with efficacy and safety parameters.

Secondary exploratory objectives include:
i. To explore the effect of aticaprant on aspects of cognitive and executive function using the CPFQ.
ii. To explore mood-related biomarkers (including but not limited to growth factors, HPA axis markers, immune system activation, metabolic markers) and genetic/epigenetic variation that may be related to clinical response, nonresponse, or safety and tolerability parameters of aticaprant.

B. Study Design

For each subject, the study consisted of two phases: a screening phase of up to 5 weeks and a double-blind treatment phase lasting 11 weeks. See, FIG. 14.

Subjects with MDD who have had treatment initiated with a permitted SSRI/SNRI and have had an inadequate or only partial response to this treatment were screened. Assessments include the MINI, Antidepressant Treatment History Questionnaire (TRQ), and MADRS.

Figure 14:
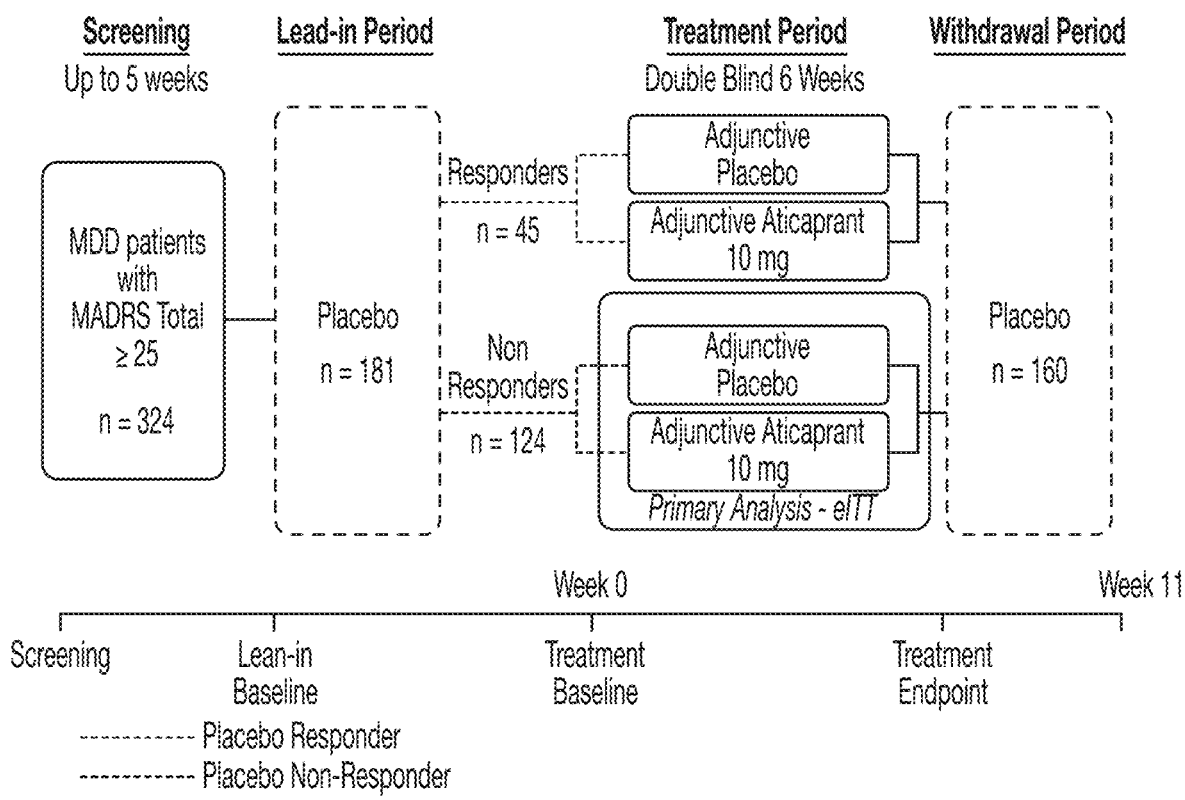
FIG. 14 is the trial design of Example 1.

The treatment phase consisted of 3 periods. A placebo lead-in period of concealed duration, after which subjects entered the double-blind treatment period when they were randomly assigned to 10 mg aticaprant (two 5 mg capsules) or continue placebo for 6 weeks. Each capsule contained aticaprant (5 mg), microcrystalline cellulose (94.95 mg), and magnesium stearate (0.05 mg) in a hard gelatin capsule. Subjects who completed the treatment period, entered the withdrawal period and were treated with placebo for the remaining time of the treatment phase. The total duration for each subject was approximately 16 weeks. There were 11 scheduled visits, including screening. An overall flow diagram is shown in FIG. 14.

Subjects were screened within 35 to 2 days prior to Day 1 to ascertain their eligibility per the inclusion and exclusion criteria. The symptoms of depression were assessed using the structured interview guide for the MADRS.

Double-Blind Treatment Phase

The duration of the double-blind treatment phase was 11 weeks divided into 3 periods. The subject received medication after completion of the visit on Day 1. The first dose was taken at home on Day 2. All medication was taken in fasting condition. At Visits 3, 4 and 5, the subjects were re-randomized to blind subjects the duration of the placebo lead-in period. During the double-blind phase, the subjects visited the center for out-patient visits every 1 to 2 weeks. See, Table 37.

TABLE 37

Time and Events Schedule (TES)

| | | [a]Double-blind treatment phase | | | | | | | | | |
|---|---|---|---|---|---|---|---|---|---|---|---|
| Phase Visit number | Screening 1 | 2 | 3 | 4 | 5 | 6 | 7 | 8 | 9 | 10 | [b]11 or EW |
| Week (end of) | −5 to 0 | 0 | 1 | 2 | 3 | 4 | 6 | 7 | 8 | 9 | 11 |
| Day | −3 5 to −2 | 1 | 8 | 15 | 22 | 29 | 43 | 50 | 57 | 64 | 78 |
| Safety assessments | | | | | | | | | | | |
| Physical and neurological examination | | X | X | | | X | | | | | X |
| ASEX | | | X | | X | X | X | | | X | X |
| KSS | | | X | | X | X | X | | | X | X |
| Suicidality by C-SSRS | X | X | X | X | X | X | X | X | X | X | X |
| Dosing | | | | | | | | | | | |
| Randomization | | X | X | X | X | | | | | | |
| Supply new medication | | X | X | X | X | X | X | X | X | | |
| Oral dose medication[d] | | Day 2 until and including Day 78[e] | | | | | | | | | |
| Meal after dosing | | X[l] | X[l] | X[l] | X[l] | X | X[l] | X[l] | X[l] | X[l] | X[l] |
| Clinical Assessments | | | | | | | | | | | |
| Structured Interview Guide MADRS | X[j] | X | X | | X | X | X | X | X | X | X |
| Structured Interview Guide SIGH-A | | X | X | | X | X | X | X | X | X | X |
| CGI-S | | X | X | X | X | X | X | X | X | X | X |
| SMDDS | | X | | | X | X | X | | | X | |
| CPFQ | | X | | | X | X | X | | | X | |
| SHAPS | X | X | X | X | X | | X | X | X | X | X |
| SATE[k] | | | | once weekly while at home | | | | | | | |
| Ongoing subject review | | | | | | | | | | | |
| Assessment of subject engagement[k] | X | | | up to 3 occasion when at home | | | | | | | |
| Adverse events | | | | Continuous | | | | | | | |
| Concomitant medication | | | | Continuous | | | | | | | |

EW = early withdrawal;
[a]Visits should be conducted + 3 days of the scheduled day (based on Visit 2, not based on previous visit).
[b]If a subject discontinues treatment before the end of the double-blind treatment phase, EW visit should be completed.
[d]At home: In fasting condition. At clinic visit days: Use blisters dispensed at the previous visit. In fasting condition after completion of predose assessments.
[e]When Visit 11 is planned up to 3 days later, continue medication.
[j]During the first screening visit and by telephone up to 4 days before Visit 2, if 2 weeks or more elapse between the MADRS rating at screening and Visit 2.
[k]Using Q1.6-app on subjects' smartphone.
[l]Breakfast, lunch or dinner after drug intake at site.

Lead-in period: Subjects who successfully complete the baseline examination visit at the clinical site/unit, were treated with placebo for the entire duration of the lead-in period.

Treatment period: At the end of the lead-in period both placebo lead-in responders and placebo lead-in non-responders were randomized to receive either placebo or 10 mg aticaprant in a 1:1 ratio for 6 weeks. Subjects remained blinded to exact timing of the randomization, response criterion and drug treatment assignment for each subject.

Withdrawal period: Subjects who completed the double-blind treatment period prior to the end of Week 11 entered the withdrawal period where they were treated with placebo for the remaining time of the treatment phase.

C. Dosage and Administration

Aticaprant was supplied as 5-mg capsules. Placebo was supplied as matching capsules. All subjects took 2 capsules QD. The capsules were taken daily from Day 2 to Day 78 in fasting condition with some water (fasting for at least 4 hours before dosing). Medication was taken before breakfast. If the subject has forgotten to take the medication before breakfast, this was done before the next following meal, at the latest at dinner of the same day. If the subject remembered later than dinner, the dose of that day was omitted, and the subject took the dose before breakfast on the next day.

When Visit 11 was planned up to 3 days later, the subject continued medication until Visit 11.

The capsules were swallowed whole and not chewed, divided, dissolved or crushed. After having taken the medication, subjects did not to eat or drink for at least 30 minutes.

The first dose was taken in fasting condition on Day 2 of the double-blind phase. The dose of the medication was:
10 mg aticaprant: 2 capsules of 5 mg aticaprant
Placebo: 2 placebo capsules.

Medication dose was adjusted as needed to 5 mg QD based on the results of a blinded review of the safety data. When a dose reduction has been decided on, this only applied to new subjects and the dose of medication was:
5 mg aticaprant: 1 capsule of 5 mg aticaprant
Placebo: 1 placebo capsule.

As used herein, the Enriched ITT Analysis Set (eITT) is defined as all enrolled lead-in placebo non-responders who were randomized into a treatment period, received at least one dose of study medication in the treatment period and have at least one post-baseline MADRS assessment during the treatment period. Similarly, the Full ITT Analysis Set (fITT) is defined as all enrolled subjects who were randomized into a treatment period, received at least one dose of study medication in the treatment period and have at least one post-treatment baseline assessment of MADRS during the treatment period.

D. Clinical Assessments
(i) Depression: Montgomery-Åsberg Depression Rating Scale (MADRS), Clinical Global Impression-Severity (CGI-S), Symptoms of Major Depressive Disorder Scale (SMDDS), and Self-assessment of treatment experience (SATE)
(ii) Anhedonia: Snaith-Hamilton Pleasure Scale (SHAPS)
(iii) Anxiety: Structured Interview Guide for the Hamilton Anxiety scale (SIGH-A) and HAM-A6
(iv) Effects on Cognition: The Cognitive and Physical Functioning Questionnaire (CPFQ)
(v) Safety assessments Standard safety assessments including physical and neurological examination, vital signs, 12-lead ECG, clinical chemistry, hematology, and urinalysis was performed. Based on observations of GI complaints in previous studies, a panel including PGI, PGII, G17 and Hp IgG was added to the clinical laboratory test panel to test for stomach mucosa status.

(vi) Suicidal ideation: C-SSRS
(vii) Exploratory: CPFQ
(viii) Central sedating effects: Karolinska Sleepiness Scale
(ix) Sexual dysfunction: ASEX E. Patient Population Of 184 subjects, 169 were randomized into the treatment period and included in the safety population, while 166 subjects were considered for the full ITT population. Out of the 166 subjects in the full ITT population, 121 (73%) were lead-in placebo non-responders (enriched ITT population) and the remaining 45 (27%) were lead-in placebo responders. Of the 121 subjects in the enriched population, 112 (92.6%) were white and 84 (69.4%) were female. The mean age was 41.6 years, ranging from 19 to 64 years. All subjects had anhedonia (defined as SHAPS total score≥20) at treatment baseline. A high anhedonia level (defined as SHAPS total score≥38) was observed in 43.8% of the subjects. In general, the treatment groups were similar with respect to the baseline characteristics. Subject demographics for the eITT and safety analysis are provided in Tables 38 and 39.

TABLE 38

Summary of Demographics and Baseline Characteristics; Full Safety Analysis

| | Placebo (N = 84) | aticaprant 10 mg (N = 85) | Total (N = 169) |
|---|---|---|---|
| Age (Years) | | | |
| N | 84 | 85 | 169 |
| Median (SD) | 42.1 (12.54) | 43.0 (12.81) | 42.6 (12.65) |
| Median | 43.5 | 43.0 | 43.0 |
| Range | (19; 64) | (21; 64) | (19; 64) |
| Gender | | | |
| N | 84 | 85 | 169 |
| Female | 62 (73.8%) | 60 (70.6%) | 122 (72.2%) |
| Male | 22 (26.2%) | 25 (29.4%) | 47 (27.8%) |
| Race | | | |
| N | 84 | 85 | 169 |
| American Indian or Alaska Native | 1 (1.2%) | 0 | 1 (0.6%) |
| Asian | 2 (2.4%) | 2 (2.4%) | 4 (2.4%) |
| Black or African American | 2 (2.4%) | 5 (5.9%) | 7 (4.1%) |
| White | 79 (94.0%) | 78 (91.8%) | 157 (92.9%) |
| Ethnicity | | | |
| N | 84 | 85 | 169 |
| Hispanic or Latino | 10 (11.9%) | 13 (15.3%) | 23 (13.6%) |
| Not Hispanic or Latino | 74 (88.1%) | 72 (84.7%) | 146 (86.4%) |
| Country | | | |
| N | 84 | 85 | 169 |
| Germany | 4 (4.8%) | 5 (5.9%) | 9 (5.3%) |
| Moldova | 15 (17.9%) | 14 (16.5%) | 29 (17.2%) |
| Russia | 25 (29.8%) | 21 (24.7%) | 46 (27.2%) |
| Ukraine | 9 (10.7%) | 7 (8.2%) | 16 (9.5%) |
| United Kingdom | 10 (11.9%) | 15 (17.6%) | 25 (14.8%) |
| United States | 21 (25.0%) | 23 (27.1%) | 44 (26.0%) |
| Baseline Height (cm) | | | |
| N | 84 | 85 | 169 |
| Mean (SD) | 167.4 (7.91) | 168.2 (8.64) | 167.8 (8.27) |
| Median | 167.5 | 167.6 | 167.6 |
| Range | (150; 183) | (152; 195) | (150; 195) |
| Baseline Weight (kg) | | | |
| N | 84 | 85 | 169 |
| Mean (SD) | 76.2 (14.73) | 78.7 (15.23) | 77.4 (14.99) |
| Median | 75.3 | 78.9 | 77.1 |
| Range | (47; 116) | (42; 119) | (42; 119) |
| Baseline BMI (kg/m$^2$) | | | |
| N | 84 | 85 | 169 |
| Mean (SD) | 27.2 (4.92) | 27.7 (4.56) | 27.5 (4.73) |
| Median | 26.6 | 28.1 | 27.6 |
| Range | (19; 35) | (18; 35) | (18; 35) |
| Presence of Anhedonia at Baseline | | | |
| N | 84 | 85 | 169 |
| No | 0 | 1 (1.2%) | 1 (0.6%) |
| Yes | 84 (100.0%) | 84 (98.8%) | 168 (99.4%) |
| Lead-in response status | | | |
| N | 84 | 85 | 169 |
| No | 62 (73.8%) | 62 (72.9%) | 124 (73.4%) |
| Yes | 22 (26.2%) | 23 (27.1%) | 45 (26.6%) |

TABLE 39

Summary of Demographics and Baseline Characteristics; eITT

| | Placebo (N = 61) | aticaprant 10 mg (N = 60) | Total (N = 121) |
|---|---|---|---|
| Age (Years) | | | |
| N | 61 | 60 | 121 |
| Mean (SD) | 41.6 (12.34) | 41.6 (12.78) | 41.6 (12.51) |
| Median | 43.0 | 40.5 | 42.0 |
| Range | (19; 64) | (21; 64) | (19; 64) |
| Gender | | | |
| N | 61 | 60 | 121 |
| Female | 42 (68.9%) | 42 (70.0%) | 84 (69.4%) |
| Male | 19 (31.1%) | 18 (30.0%) | 37 (30.6%) |
| Race | | | |
| N | 61 | 60 | 121 |
| American Indian or Alaska Native | 1 (1.6%) | 0 | 1 (0.8%) |
| Asian | 2 (3.3%) | 1 (1.7%) | 3 (2.5%) |
| Black or African American | 2 (3.3%) | 3 (5.0%) | 5 (4.1%) |
| White | 56 (91.8%) | 56 (93.3%) | 112 (92.6%) |
| Ethnicity | | | |
| N | 61 | 60 | 121 |
| Hispanic or Latino | 3 (4.9%) | 7 (11.7%) | 10 (8.3%) |
| Not Hispanic or Latino | 58 (95.1%) | 53 (88.3%) | 111 (91.7%) |
| Country | | | |
| N | 61 | 60 | 121 |
| Germany | 4 (6.6%) | 4 (6.7%) | 8 (6.6%) |
| Moldova | 15 (24.6%) | 14 (23.3%) | 29 (24.0%) |
| Russia | 19 (31.1%) | 18 (30.0%) | 37 (30.6%) |
| Ukraine | 7 (11.5%) | 5 (8.3%) | 12 (9.9%) |
| United Kingdom | 6 (9.8%) | 10 (16.7%) | 16 (13.2%) |
| United States | 10 (16.4%) | 9 (15.0%) | 19 (15.7%) |
| Baseline Height (cm) | | | |
| N | 61 | 60 | 121 |
| Mean (SD) | 168.1 (8.19) | 167.3 (8.10) | 167.7 (8.13) |
| Median | 168.0 | 166.3 | 167.0 |
| Range | (151; 183) | (152; 186) | (151; 186) |

TABLE 39-continued

Summary of Demographics and Baseline Characteristics; eITT

| | Placebo (N = 61) | aticaprant 10 mg (N = 60) | Total (N = 121) |
|---|---|---|---|
| Baseline Weight (kg) | | | |
| N | 61 | 60 | 121 |
| Mean (SD) | 74.7 (14.19) | 76.8 (15.12) | 75.7 (14.63) |
| Median | 74.2 | 77.1 | 75.6 |
| Range | (47; 116) | (42; 119) | (42; 119) |
| Baseline BMI (kg/m$^2$) | | | |
| N | 61 | 60 | 121 |
| Mean (SD) | 26.4 (4.67) | 27.3 (4.36) | 26.9 (4.52) |
| Median | 25.7 | 27.8 | 26.7 |
| Range | (19; 35) | (18; 35) | (18; 35) |
| Presence of Anhedonia at Baseline | | | |
| N | 61 | 60 | 121 |
| No | 0 | 0 | 0 |
| Yes | 61 (100.0%) | 60 (100.0%) | 121 (100.0%) |
| Load-in response status | | | |
| N | 61 | 60 | 121 |
| No | 61 (100.0%) | 60 (100.0%) | 121 (100.0%) |
| Yes | 0 | 0 | 0 |

E. Evaluations of Efficacy

At the end of the lead-in period, response status of the subjects was assessed according to the double-blind response criteria based on reduction in MADRS relative to lead-in baseline. Both lead-in placebo responders and lead-in placebo non-responders were randomly assigned in a 1:1 ratio to either aticaprant or placebo in the treatment period. The randomization was stratified by lead-in response status (non-responders: <30% reduction from baseline in MADRS total score at the end of the lead-in period vs responders: ≥30% reduction from baseline at the end of the lead-in period) and presence/absence of anhedonia (presence defined as SHAPS total score≥20).

Treatment duration: The study consisted of two periods: a screening phase of up to 5 weeks and a double-blind treatment phase of 11 weeks. The double-blind treatment phase of the trial consisted of 3 periods. The first period was a placebo lead-in of 3 weeks, after which subjects entered the treatment period when they were randomly assigned to aticaprant or continuation on placebo for 6 weeks. Subjects who successfully completed the treatment period were treated with placebo during a 2-week withdrawal period, i.e., Period 3. The total duration for each subject was approximately 16 weeks.

Primary analysis set for efficacy: The efficacy analysis is based on the eITT set defined as all enrolled lead-in placebo non-responders who were randomized into the treatment period, received at least one dose of medication, and have at least one post-baseline MADRS assessment during the treatment period. The primary analysis set is used for all efficacy endpoints.

Secondary analysis set for efficacy: A secondary analysis set is the fITT set defined as all enrolled subjects who were randomized into the treatment period, received at least one dose of medication, and have at least one post-baseline MADRS assessment during the treatment period. The secondary analysis set is used for all efficacy endpoints to examine the effect in the general population, which may be useful for designing subsequent studies in the development program.

Analysis set for safety: The safety analysis is based on the full safety analysis set, defined as all enrolled subjects who received at least one dose of medication in the treatment period.

The efficacy endpoints were presented for both the eITT and the fITT.

Level of significance: The analysis of primary efficacy endpoint was performed at a significance level of 0.20 (one-sided). The analysis of secondary efficacy endpoints was performed at a significance level of 0.20 (two-sided). No adjustment for multiple comparisons was performed.

Figure 15:
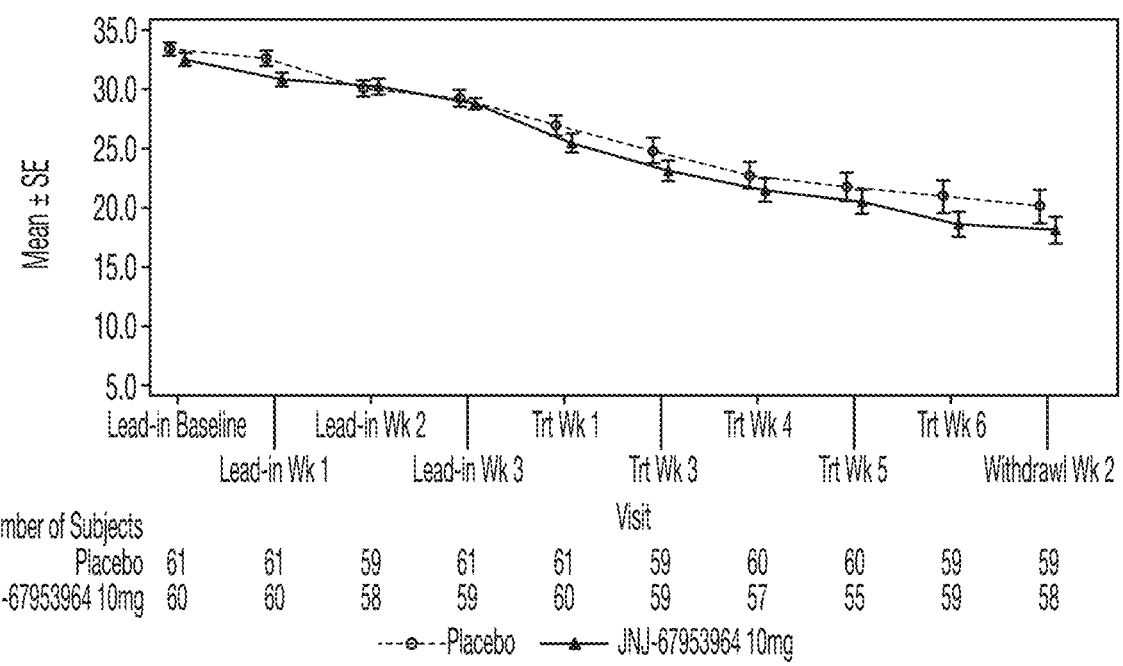
FIG. 15 is a line graph showing the MADRS (Montgomery-Åsberg Depression Rating Scale) total score: least squares mean changes from baseline (±SE) during the treatment period for the enriched intent-to-treat (eITT) analysis set.

F. Results (i) Primary Endpoint: Change from Treatment Baseline in MADRS Total Score at Treatment Week 6 in Non-Responders During Placebo Lead-In Period Enriched ITT Analysis Set The mean (SD) MADRS total score at treatment baseline was 29.0 (4.61), ranging from 19 to 41. See, FIG. 15. The mean change from treatment baseline (SD) in MADRS total score at treatment week 6 was −10.2 (8.44) for aticaprant and −8.2 (8.53) for placebo. The observed effect size was 0.23. See, Tables 40-42 and FIG. 18.

TABLE 40

Summary of Baseline Psychiatry Rating Scales at the Start of the Lead-in and Treatment Periods; eITT Analysis Set

| | MADRS Total Score | | | SHAPS Total Score | | |
|---|---|---|---|---|---|---|
| | N | Mean (SD) | Median (Range) | N | Mean (SD) | Median (Range) |
| Lead-in Baseline | | | | | | |
| Placebo | 61 | 33.4 (4.25) | 34.0 (26; 42) | 61 | 38.0 (6.28) | 38.0 (22; 55) |
| Aticaprant | 60 | 32.5 (4.18) | 32.0 (25; 45) | 60 | 38.3 (5.66) | 38.0 (21; 53) |
| Total | 121 | 32.9 (4.22) | 33.0 (25; 45) | 121 | 38.1 (5.96) | 38.0 (21; 55) |
| Treatment Baseline | | | | | | |
| Placebo | 61 | 29.2 (5.47) | 29.0 (19; 41) | 61 | 36.8 (5.75) | 37.0 (23; 50) |
| Aticaprant | 60 | 28.7 (3.58) | 28.5 (21; 36) | 60 | 36.4 (5.16) | 36.5 (20; 49) |
| Total | 121 | 29.0 (4.61) | 29.0 (19; 41) | 121 | 36.6 (5.45) | 37.0 (20; 50) |

TABLE 41

MADRS Total Score: Mean Changes to Placebo During the Treatment Period; eITT Analysis Set

| Analysis Visit Treatment | N | Mean Change from Baseline (SD) | Mean Change to Placebo (SD pooled) | 90% CI for Mean Change to Placebo | Effect Size |
|---|---|---|---|---|---|
| Treatment Week 1 | | | | | |
| Placebo | 61 | −2.2 (3.73) | | | |
| Aticaprant | 60 | −3.3 (5.21) | −1.1 (4.52) | [−2.4, 0.3] | −0.24 |
| Treatment Week 3 | | | | | |
| Placebo | 59 | −4.3 (5.99) | | | |
| Aticaprant | 59 | −5.7 (6.38) | −1.4 (6.18) | [−3.3, 0.5] | −0.22 |
| Treatment Week 4 | | | | | |
| Placebo | 60 | −6.4 (6.66) | | | |
| Aticaprant | 57 | −7.3 (7.35) | −0.9 (7.00) | [−3.1, 1.2] | −0.14 |

TABLE 41-continued

MADRS Total Score: Mean Changes to Placebo During the Treatment Period; eITT Analysis Set

| Analysis Visit Treatment | N | Mean Change from Baseline (SD) | Mean Change to Placebo (SD pooled) | 90% CI for Mean Change to Placebo | Effect Size |
|---|---|---|---|---|---|
| Treatment Week 5 | | | | | |
| Placebo | 60 | −7.4 (7.15) | | | |
| Aticaprant | 55 | −8.4 (7.36) | −1.1 (7.25) | [−3.3, 1.2] | −0.14 |
| Treatment Week 6 | | | | | |
| Placebo | 59 | −8.2 (8.53) | | | |
| Aticaprant | 59 | −10.2 (8.44) | −2.0 (8.49) | [−4.6, 0.6] | −0.23 |

Negative change from baseline indicates improvement.
Negative change to Placebo indicates favorable aticaprant effect.
Negative effect size favors aticaprant; positive effect size favors Placebo.

TABLE 42

MADRS Total Score: MMRM Results-Estimated LS Means and Comparison versus Placebo; eITT Analysis Set

| Analysis Visit Treatment | N | Mean (SD) | Mean (SD) | LSMean (SE) | LSMean Difference (SE)\ Treatment Placebo | 60% Confidence Interval on Difference | p-value[a] |
|---|---|---|---|---|---|---|---|
| Treatment Week 1 | | | | | | | |
| Placebo | 61 | 26.9 (6.77) | −2.2 (3.73) | −2.0 (0.92) | | | |
| aticaprant | 60 | 25.4 (5.93) | −3.3 (5.21) | −3.2 (0.93) | −1.2 (1.24) | [−2.28, −0.19] | 0.1604 |
| Treatment Week 3 | | | | | | | |
| Placebo | 59 | 24.8 (8.25) | −4.3 (5.99) | −4.2 (0.92) | | | |
| aticaprant | 59 | 23.1 (6.58) | −5.7 (6.38) | −5.6 (0.93) | −1.5 (1.25) | [−2.55, −0.44] | 0.1159 |
| Treatment Week 4 | | | | | | | |
| Placebo | 60 | 22.7 (9.10) | −6.4 (6.66) | −6.2 (0.92) | | | |
| aticaprant | 57 | 21.5 (7.49) | −7.3 (7.35) | −7.3 (0.93) | −1.1 (1.25) | [−2.19, −0.09] | 0.1811 |
| Treatment Week 5 | | | | | | | |
| Placebo | 60 | 21.7 (9.54) | −7.4 (7.15) | −7.2 (0.92) | | | |
| aticaprant | 55 | 20.5 (7.44) | −8.4 (7.36) | −8.7 (0.94) | −1.5 (1.25) | [−2.60, −0.48] | 0.1103 |
| Treatment Week 6 | | | | | | | |
| Placebo | 59 | 20.9 (10.54) | −8.2 (8.53) | −8.0 (0.92) | | | |
| aticaprant | 59 | 18.6 (8.14) | −10.2 (8.44) | −10.1 (0.93) | −2.1 (1.25) | [−3.20, −1.09] | 0.0443 |

Figures 16, 17:
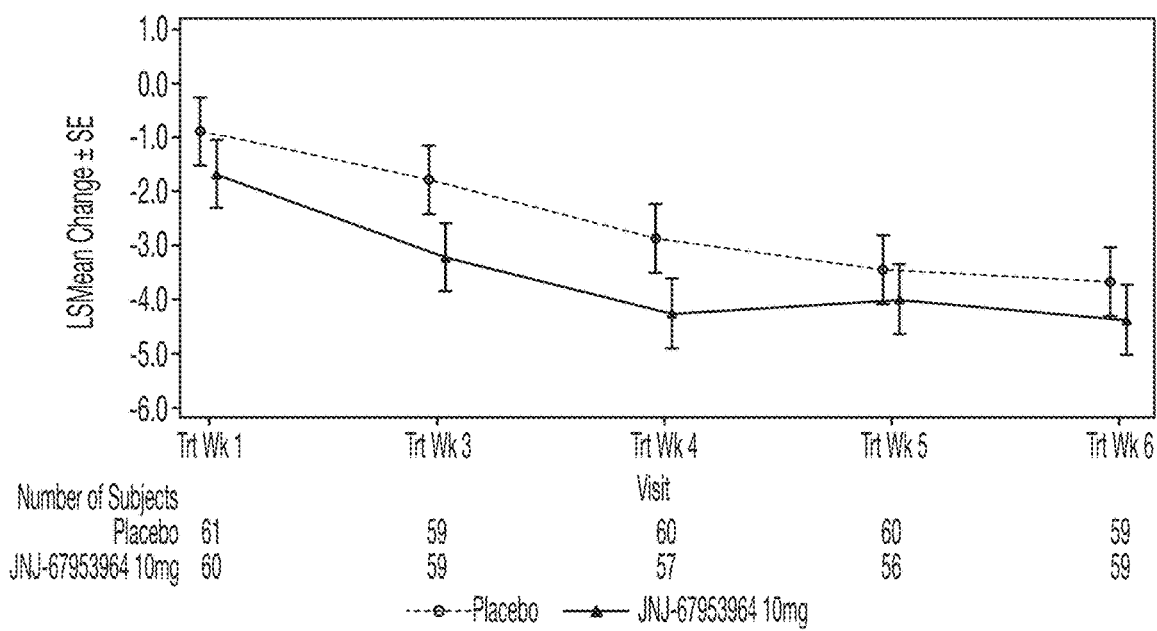
FIG. 16 is a plot showing MADRS total score changes at treatment week 6 for enriched and full population: MMRM results-estimated LS means and comparison versus placebo.
FIG. 17 is a line graph showing SHAPS (Snaith-Hamilton Pleasure Scale) total score: least squares mean changes from baseline (±SE) during the treatment period for the eITT analysis set.
Figure 19:
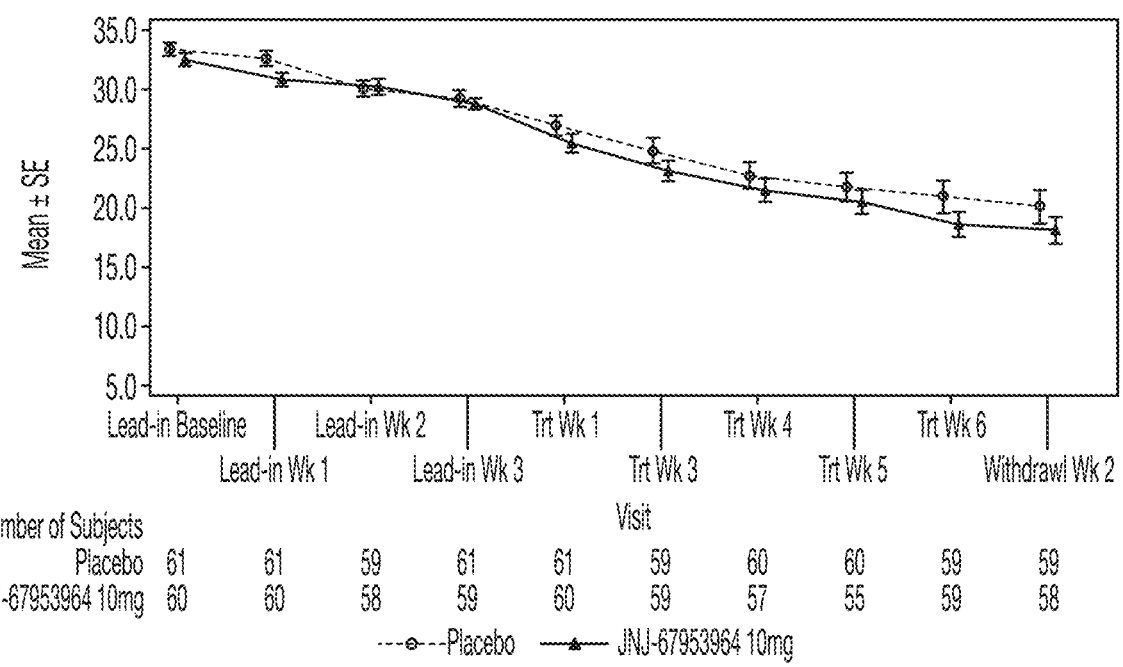
FIG. 19 is a line graph showing MADRS total score: mean values (±SE) over time for the eITT analysis set.

[a]One-sided test for no difference between treatments from a MMRM model with subject as random effect; country, treatment, time and time-by-treatment interaction as factors; and baseline MADRS total score as continuous covariate. An AR(1) variance-covariance matrix was employed Based on the results of a MMRM model with subject as random effect; country, treatment, time and time-by-treatment interaction as factors; and baseline MADRS total score as continuous covariate a significant positive efficacy signal was detected for aticaprant versus placebo at the one-sided 0.20 significance level. The estimated LS mean difference at treatment week 6 between aticaprant and placebo was −2.1 with 80% 1-sided CI upper limit of −1.09. The corresponding p-value was 0.044. The treatment effect was larger in the fITT than in the eITT population: −3.1 with 80% 1-sided CI upper limit of −2.2 (p=0.002). The effect size was 0.36 and 0.23, respectively. See, FIGS. 15 and 16.

Full ITT Analysis Set

The mean (SD) baseline MADRS total score at treatment baseline was 25.3 (7.86), ranging from 0 to 41. See, FIGS. 20-A and 20-B. The mean changes from treatment baseline in MADRS total score at Treatment Week 6 for fITT were smaller than for eITT: −9.7 (8.02) for aticaprant and −6.6 (8.57) for placebo. The observed effect size was 0.36. These results illustrate a statistical superiority over placebo with a durability of effect with the greatest difference seen at week 6. See, Table 43.

TABLE 43

Summary of Baseline Psychiatry Rating Scales at the Start of the Lead-in and Treatment Periods; fITT Analysis Set

| | MADRS Total Score | | | | SHAPS Total Score | | |
|---|---|---|---|---|---|---|---|
| | N | Mean (SD) | Median (Range) | | N | Mean (SD) | Median (Range) |
| Lead-in Baseline | | | | | | | |
| Placebo | 83 | 32.8 (4.25) | 33.0 (26; 42) | | 83 | 37.8 (6.01) | 38.0 (22; 55) |
| Aticaprant | 83 | 32.4 (4.27) | 32.0 (21; 45) | | 83 | 37.3 (6.23) | 38.0 (14; 53) |
| Total | 166 | 32.6 (4.25) | 32.0 (21; 45) | | 166 | 37.6 (6.11) | 38.0 (14; 55) |
| Treatment Baseline | | | | | | | |
| Placebo | 83 | 25.7 (7.73) | 26.0 (10; 41) | | 83 | 36.3 (5.44) | 36.0 (23; 50) |
| Aticaprant | 83 | 24.8 (8.02) | 27.0 (0; 36) | | 83 | 35.0 (5.85) | 36.0 (14; 49) |
| Total | 166 | 25.3 (7.86) | 26.5 (0; 41) | | 166 | 35.6 (5.67) | 36.0 (14; 50) |

Significant effect for aticaprant versus placebo in fITT population was also detected. The estimated LS mean difference at treatment week 6 between aticaprant and placebo was −3.1 with 80% 1-sided CI upper limit of −2.21. The corresponding p-value was 0.002. See, Tables 44-45 and FIG. 16.

TABLE 44

MADRS Total Score: MMRM Results-Estimated LS Means and Comparison versus Placebo; fITT Analysis Set

| | | Change from Baseline | | | | | |
|---|---|---|---|---|---|---|---|
| Analysis Visit Treatment | N | Mean (SD) | Mean (SD) | LSMean (SE) | LSMean Difference (SE)\ Treatment Placebo | 60% Confidence Interval on Difference | p-value[a] |
| Treatment Week 1 | | | | | | | |
| Placebo | 83 | 24.0 (8.12) | −1.8 (4.00) | −1.7 (0.78) | | | |
| aticaprant | 83 | 21.7 (8.78) | −3.1 (4.81) | −3.2 (0.77) | −1.6 (1.03) | [−2.44, −0.70] | 0.0653 |
| Treatment Week 3 | | | | | | | |
| Placebo | 81 | 22.2 (9.28) | −3.4 (6.50) | −3.4 (0.78) | | | |
| aticaprant | 80 | 20.0 (8.53) | −5.1 (6.74) | −5.2 (0.78) | −1.9 (1.04) | [−2.74, −0.991] | 0.0368 |
| Treatment Week 4 | | | | | | | |
| Placebo | 82 | 20.8 (9.24) | −4.9 (7.02) | −4.8 (0.78) | | | |
| aticaprant | 78 | 17.9 (9.32) | −7.2 (7.02) | −7.3 (0.78) | −2.5 (1.04) | [−3.34, −1.59] | 0.0093 |

TABLE 44-continued

MADRS Total Score: MMRM Results-Estimated LS Means and Comparison versus Placebo; fITT Analysis Set

| Analysis Visit Treatment | N | Mean (SD) | Change from Baseline Mean (SD) | LSMean (SE) | LSMean Difference (SE)\ Treatment Placebo | 60% Confidence Interval on Difference | p-value[a] |
|---|---|---|---|---|---|---|---|
| Treatment Week 5 | | | | | | | |
| Placebo | 82 | 19.2 (9.89) | −6.4 (7.16) | −6.3 (0.78) | | | |
| aticaprant | 76 | 16.7 (9.47) | −8.3 (7.48) | −8.7 (0.78) | −2.4 (1.05) | [−3.24, −1.47] | 0.0125 |
| Treatment Week 6 | | | | | | | |
| Placebo | 81 | 19.0 (10.35) | −6.6 (8.57) | −6.5 (0.78) | | | |
| aticaprant | 77 | 15.9 (9.09) | −9.7 (8.02) | −9.6 (0.79) | −3.1 (1.05) | [−3.97, −2.21] | 0.0017 |

[a] One-sided test for no difference between treatments from a MMRM model with subject as random effect; country, treatment, time and time-by-treatment interaction as factors; and baseline MADRS total score as continuous covariate. An AR(1) variance-covariance matrix was employed

TABLE 45

MADRS (Montgomery-Åsberg Depression Rating Scale) Total Score: Mean Changes to Placebo During the Treatment Period; fITT Analysis Set

| Analysis Visit Treatment | N | Mean Change to Placebo (SD pooled) | 90% CI for Mean Change to Placebo | Effect Size |
|---|---|---|---|---|
| Treatment Week 1 | | | | |
| Placebo | 83 | | | |
| Aticaprant | 83 | −1.3 (4.43) | [−2.4, −0.2] | −0.29 |
| Treatment Week 3 | | | | |
| Placebo | 81 | | | |
| Aticaprant | 80 | −1.7 (6.62) | [−3.4, 0.0] | −0.26 |
| Treatment Week 4 | | | | |
| Placebo | 82 | | | |
| Aticaprant | 78 | −2.3 (7.02) | [−4.1, −0.4] | −0.32 |
| Treatment Week 5 | | | | |
| Placebo | 82 | | | |
| Aticaprant | 76 | −1.9 (7.31) | [−3.9, −0.0] | −0.26 |
| Treatment Week 6 | | | | |
| Placebo | 81 | | | |
| Aticaprant | 77 | −3.0 (8.31) | [−5.2, −0.8] | −0.36 |

Negative change from baseline indicates improvement.
Negative change to Placebo indicates favorable aticaprant effect.
Negative effect size favors aticaprant; positive effect size favors Placebo.

COVID-19 Impact on Primary Efficacy Assessment

Supplementary analysis was conducted using the same MMRM model as described for the primary analysis on all the data collected prior to 15 Mar. 2020 (estimated date of the COVID-19 lockdowns in most of the countries participating in the trial). Seventeen percent of the subjects in fITT and 19% in eITT population had at least one of the MADRS assessment excluded from the model due to COVID-19 impact. Results of the analysis corroborated the findings of the primary efficacy analysis in both: eITT and fITT populations. LSMeans difference estimate was −3.0 (80% 1-sided CI upper limit of −1.88) for eITT and −3.4 (80% 1-sided CI upper limit of −2.51) for fITT.

(ii) Secondary Endpoints

MADRS Remission Rates Over Treatment Period

Figure 21:
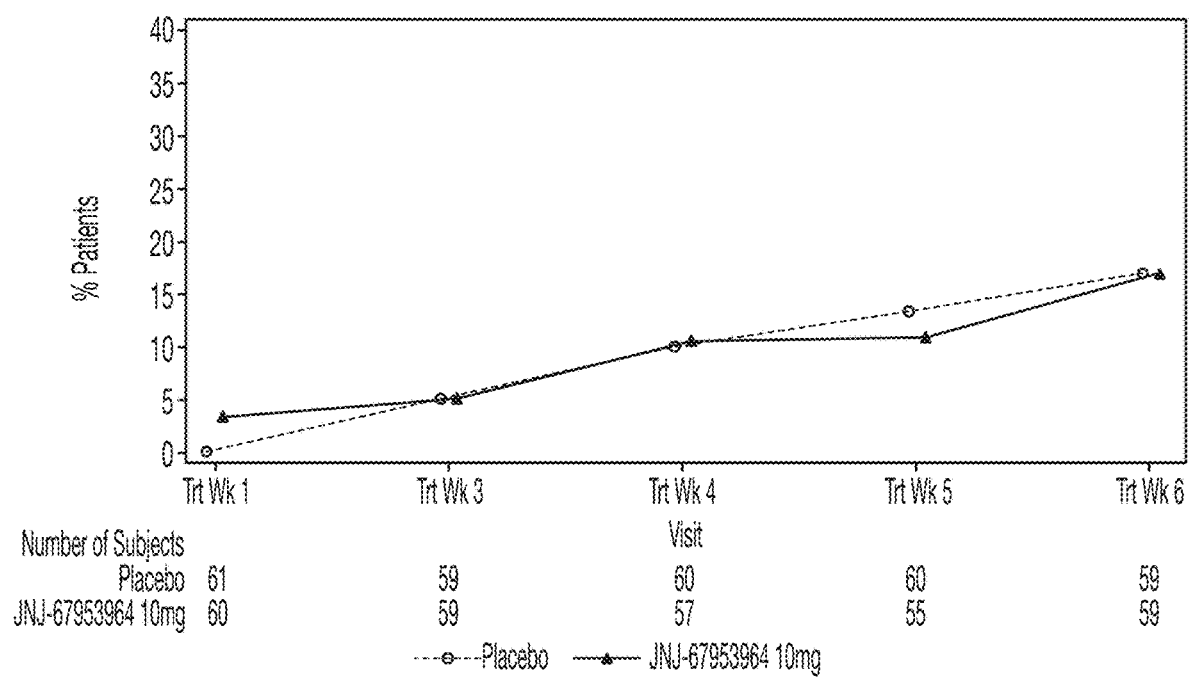
FIG. 21 is a line graph showing MADRS total score: percentage of subjects with remission of depressive symptoms (total score≤10) during the treatment period for the eITT analysis set.
Figure 22:
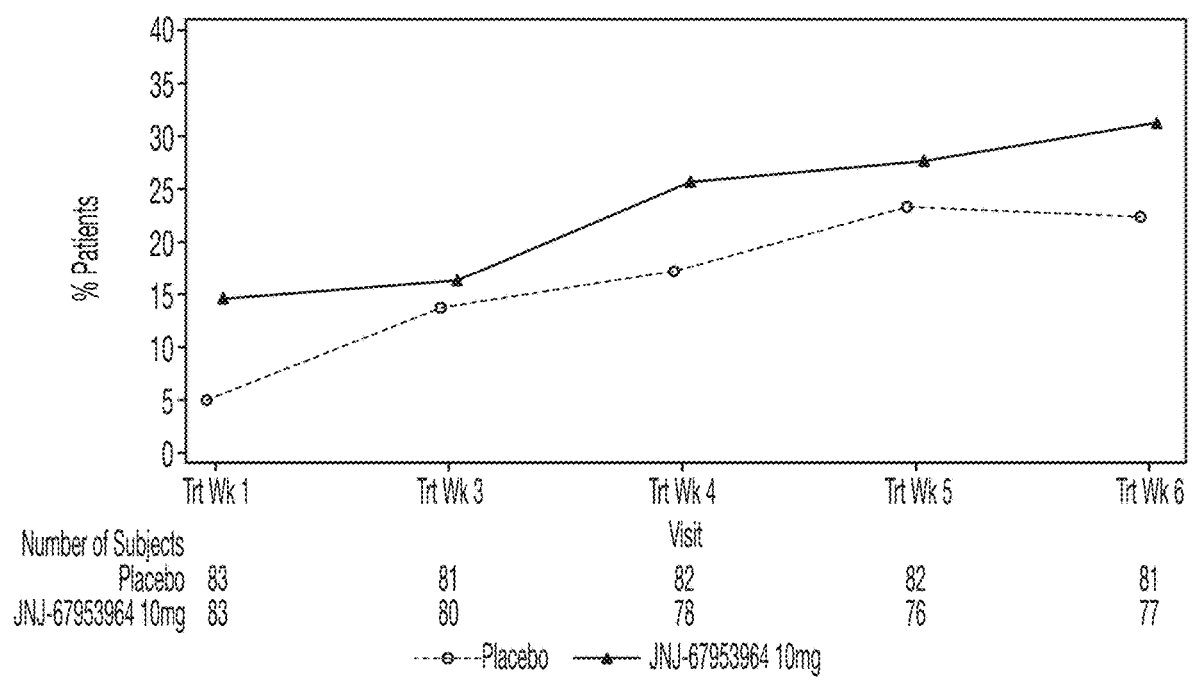
FIG. 22 is a line graph showing MADRS total score: percentage of subjects with remission of depressive symptoms (total score≤10) during the treatment period for the fITT analysis set.
Figure 23:
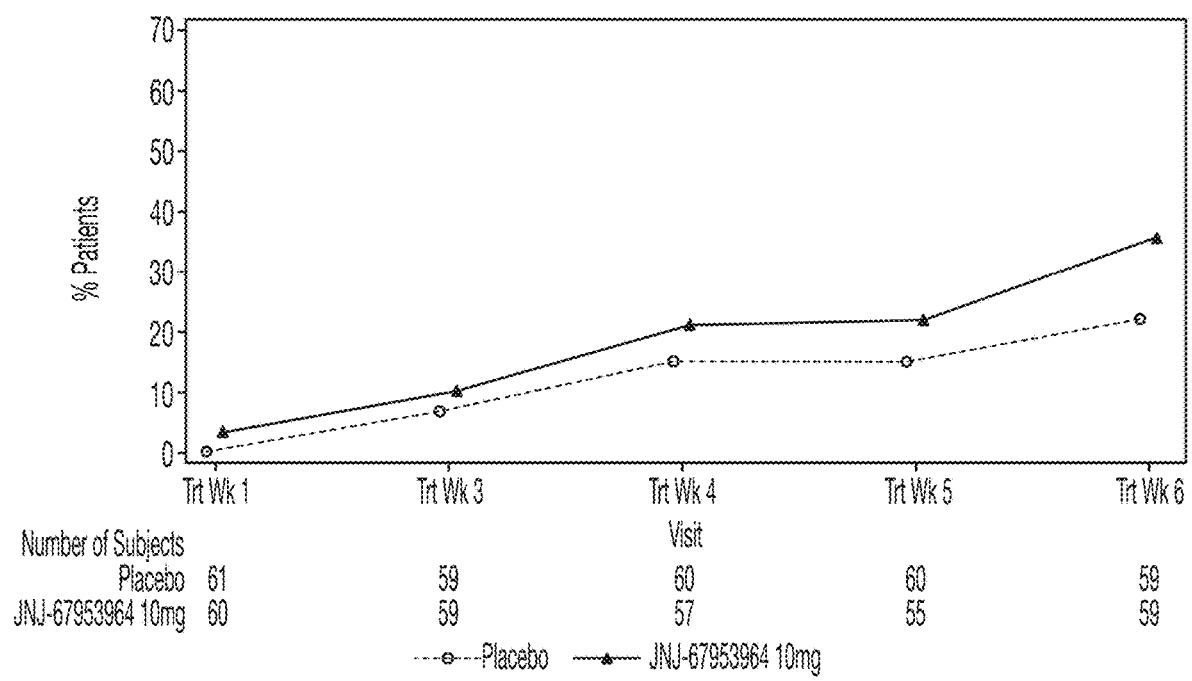
FIG. 23 is a line graph showing MADRS total score: percentage of responders (≥30% improvement from baseline) during the treatment period for the eITT analysis set.
Figure 24:
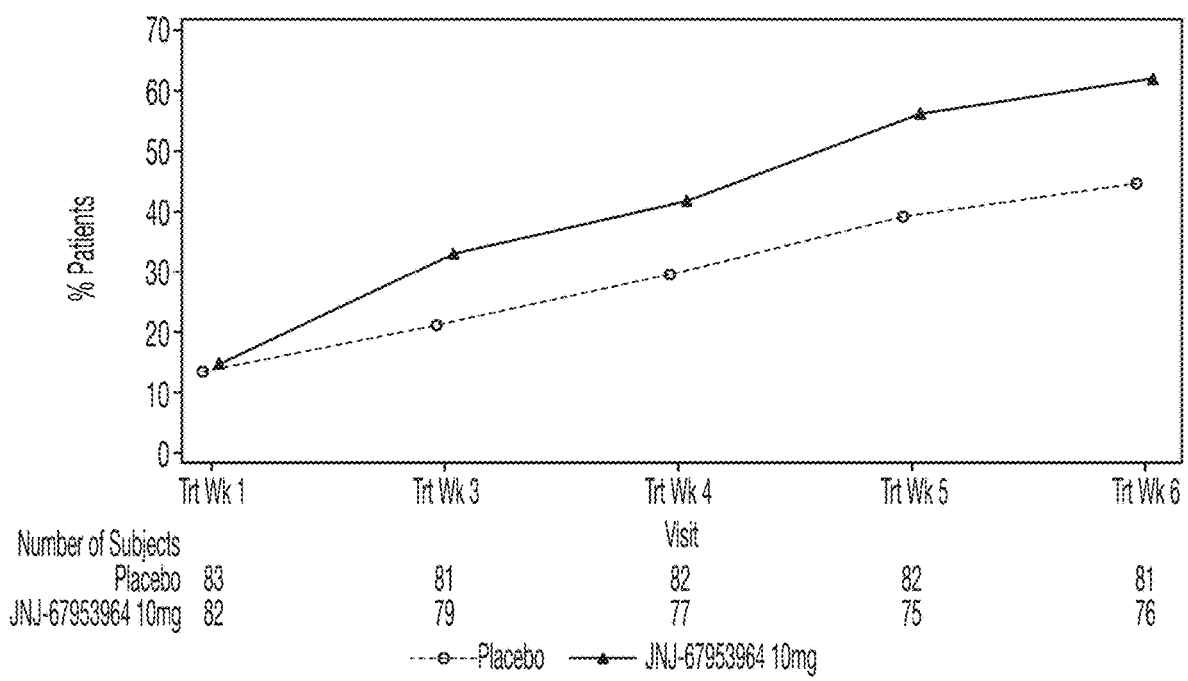
FIG. 24 is a line graph showing MADRS total score: percentage of responders (≥30% improvement from baseline) during the treatment period for the fITT analysis set.
Figure 25:
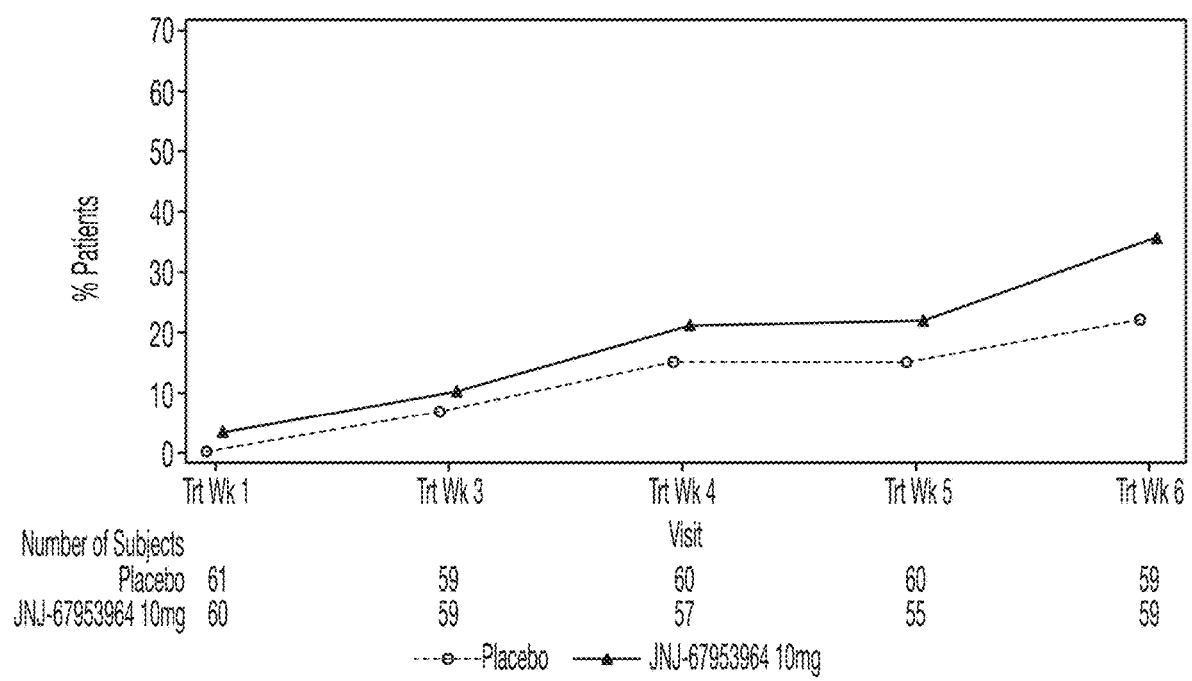
FIG. 25 is a line graph showing MADRS total score: percentage of responders (≥50% improvement from baseline) during the treatment period for the eITT analysis set.
Figure 26:
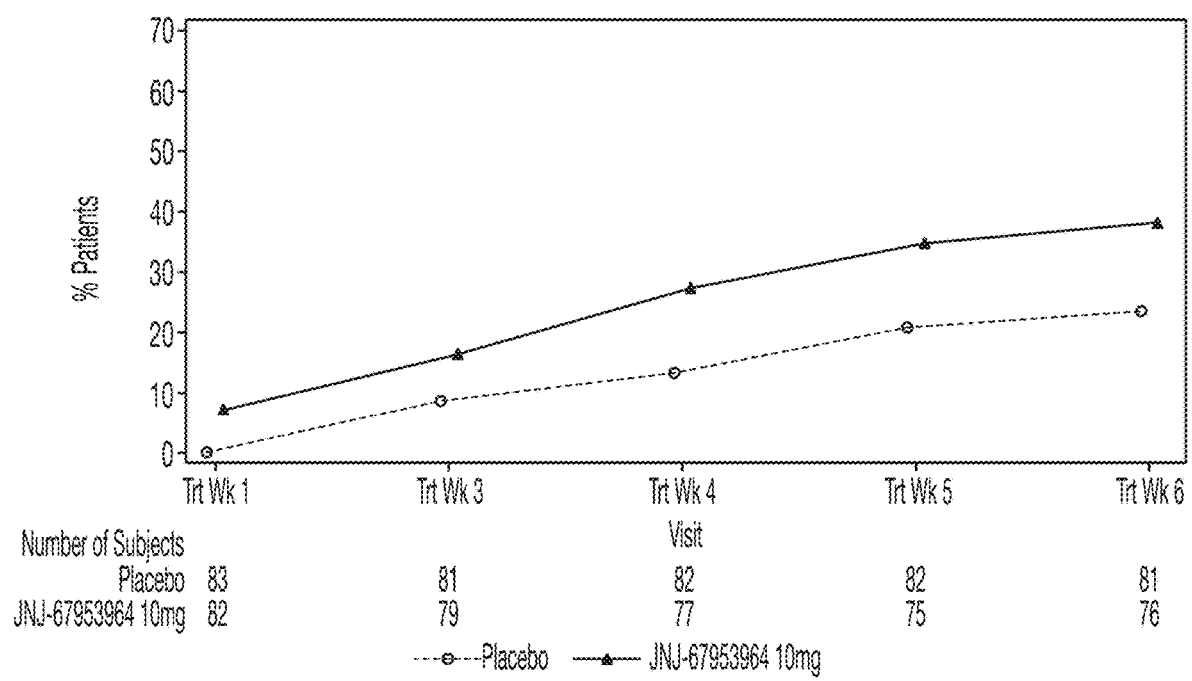
FIG. 26 is a line graph showing MADRS total score: percentage of responders (≥50% improvement from baseline) during the treatment period for the fITT analysis set.

At Treatment Week 6 the percentage of subjects with MADRS remission (MADRS total score≤10) in the eITT population was 16.9% for aticaprant and 16.9% for placebo. Treatment week 6 remission rates in fITT population were 31.2% for aticaprant and 22.2% for placebo. For both populations (eITT and fITT), no significant treatment differences were detected at treatment week 6 using Chi-square test (2-sided p=0.999 and p=0.203, respectively). See, FIGS. 21 and 22.

MADRS Response Rates (at Least 30% Improvement) Over Treatment Period

The percentage of subjects with ≥30% improvement in MADRS total score at treatment week 6 in the eITT population was 57.6% for aticaprant and 45.8% for placebo. Treatment week 6 response rates in fITT population were 61.8% for aticaprant and for 44.4% placebo. For both populations, treatment differences at Treatment Week 6 were significant at 20% 2-sided significance level (Chi-square test: p=0.197 for eITT and p=0.029 for fITT).

MADRS Response Rates (at Least 50% Improvement) Over Treatment Period

The percentage of subjects with >50% improvement in MADRS total score at treatment week 6 in the eITT population was 35.6% for aticaprant and 22.0% for placebo. Treatment week 6 response rates in fITT population were 38.2% for Aticaprant and 23.5% for placebo. For both populations, treatment differences at treatment week 6 were significant at 20% 2-sided significance level (Chi-square test: p=0.104 for eITT and p=0.046 for fITT). See, Table 46 and FIGS. 23-26.

TABLE 46

Change from Treatment Baseline in MADRS Total Score at Treatment Week 6 in Both Responders and Non-Responders during Placebo Lead-in Period

| End point values | Placebo | aticaprant 10 milligrams (mg) |
|---|---|---|
| Number of subjects analyzed | 81 | 77 |
| Units: score on a scale Measure Type: Least Squares Mean (Standard Error) | −6.5 ± 0.78 | −9.6 ± 0.79 |
| P-value | | =0.0017 |
| Parameter type | | Least Squares Mean Difference |
| Point estimate | | −3.1 |
| Confidence interval level | | 80% |
| sides | | 1-Sided |
| lower limit | | — |
| upper limit | | −2.21 |
| Variability estimate | | Standard Error of the mean |
| Dispersion value | | 1.05 |

Changes in SHAPS Total Score from Treatment Baseline to Treatment Week 6
Enriched ITT Analysis Set In eITT population, in a subgroup of subjects with high anhedonia level (baseline SHAPS total score≥38), larger differences between aticaprant placebo at Treatment Week 6 were observed than in subjects with low anhedonia level (20≤baseline SHAPS total score<38). The effect size was 0.38 and 0.11, respectively.

Figure 27:
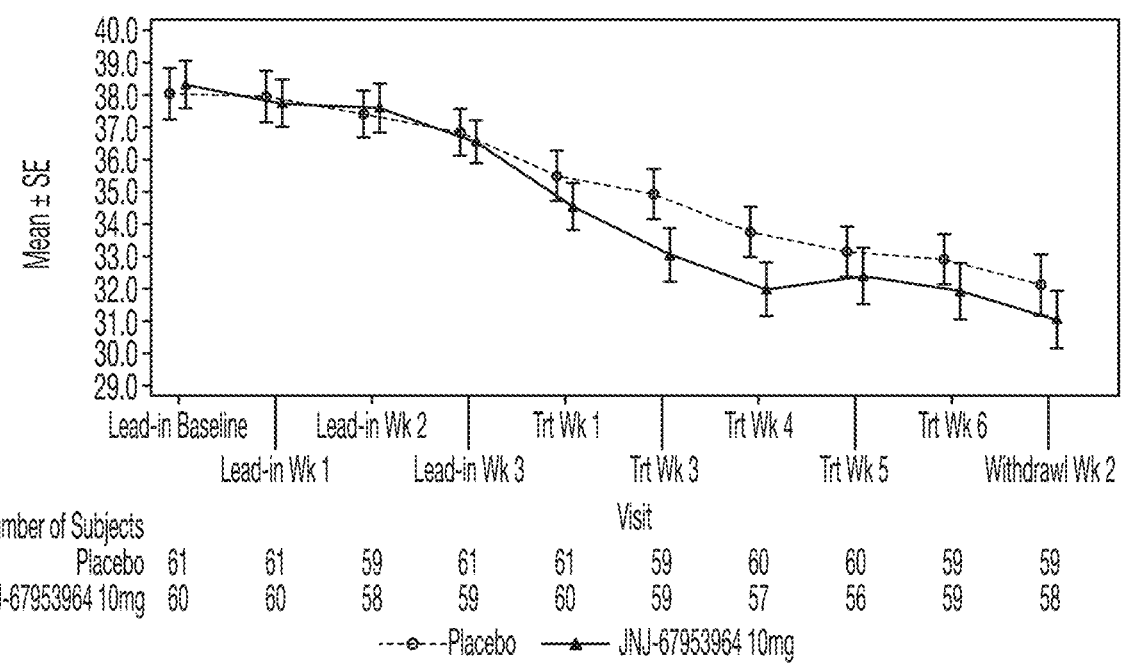
FIG. 27 is a line graph showing SHAPS total score: mean values (±SE) over time for the eITT analysis set.
Figure 34:
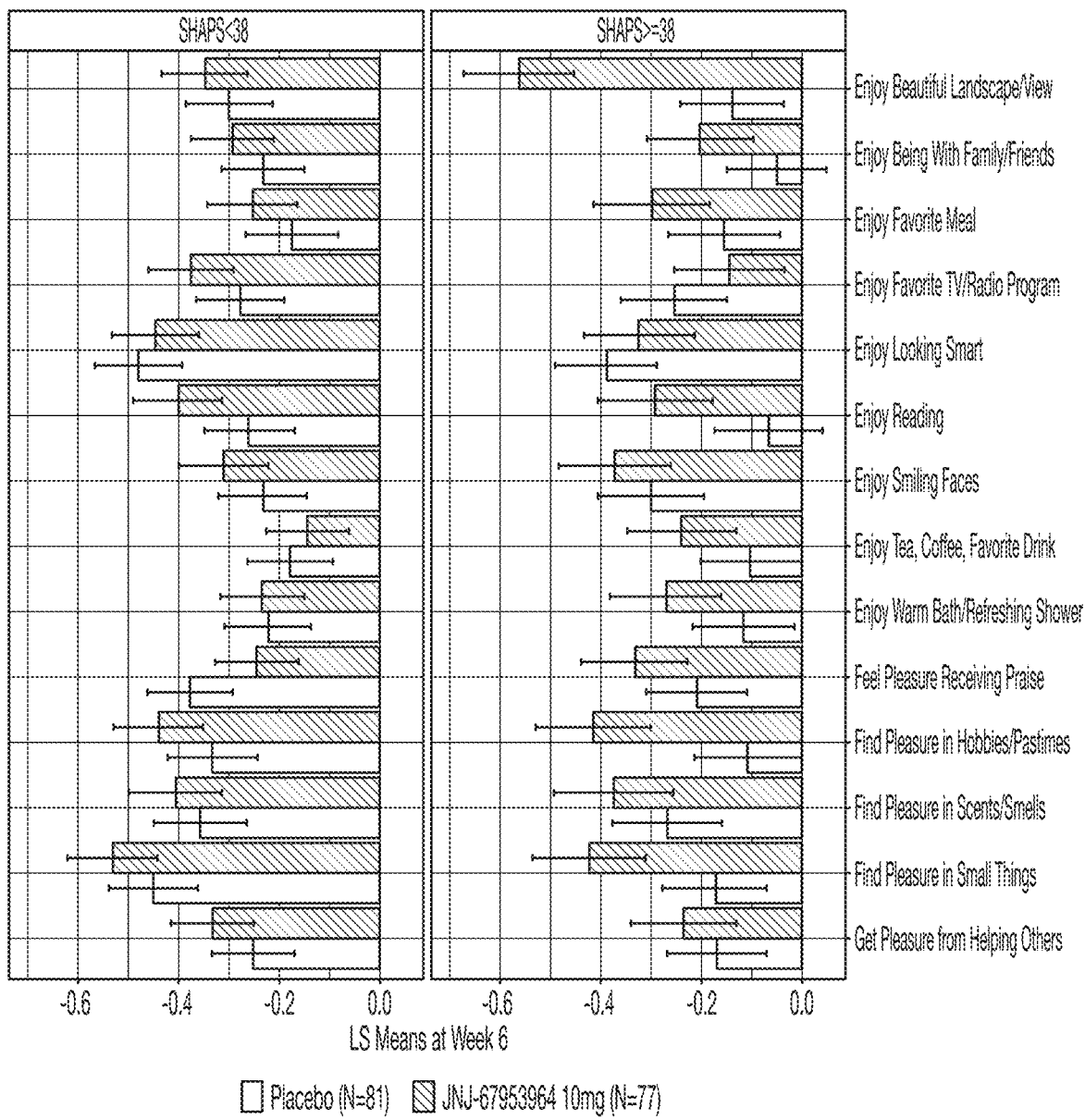
FIG. 34 is a bar graph showing the SHAPS items: LS means for change from baseline at week 6 by baseline SHAPS total score for the fITT analysis set. In this figure and going from top to bottom, the bars alternatively refer to placebo or aticaprant. For example, the first bar refers to aticaprant, the second bar refers to placebo, the third bar refers to aticaprant, etc.
Figure 35:
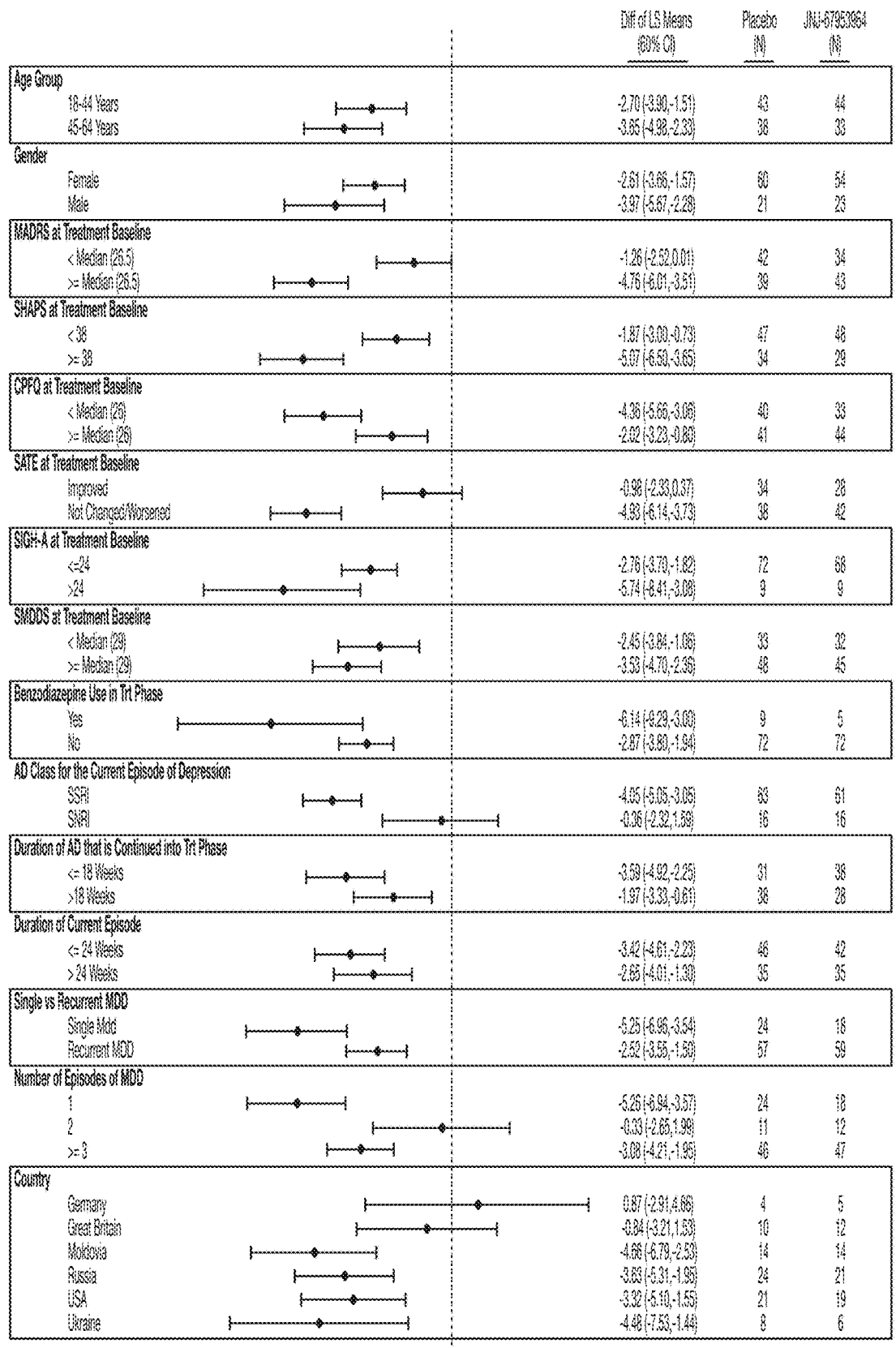
FIG. 35 is a plot showing MADRS total score: difference of LSMeans (60% at Weeks 6 by different subgroups for the fITT analysis set. In this plot, <17 indicates mild severity; 18-24 indicates mild to moderate severity, and 25-30 indicates moderate to severe.

The mean (SD) SHAPS total score at treatment baseline was 36.6 (5.45), ranging from 20 to 50. The mean change from treatment baseline (SD) in SHAPS total score at treatment week 6 was −4.6 (6.23) for aticaprant and −4.2 (5.04) for placebo. The observed effect size was 0.07. See, Table 47 and FIGS. 27 and 34.

TABLE 47

SHAPS Total Score: Mean Changes to Placebo During the Treatment Period; eITT Analysis Set

| Analysis Visit Treatment | N | Mean Change from Baseline (SD) | Mean Change to Placebo (SD pooled) | 90% CI for Mean Change to Placebo | Effect Size |
|---|---|---|---|---|---|
| Treatment Week 1 | | | | | |
| Placebo | 61 | −1.3 (3.17) | | | |
| aticaprant | 60 | −1.9 (4.30) | −0.6 (3.77) | [−1.7, 0.6] | −0.15 |
| Treatment Week 3 | | | | | |
| Placebo | 59 | −2.2 (4.65) | | | |
| aticaprant | 59 | −3.4 (5.25) | −1.2 (4.96) | [−2.8, 0.3] | −0.25 |
| Treatment Week 4 | | | | | |
| Placebo | 60 | −3.3 (4.47) | | | |
| aticaprant | 57 | −4.5 (5.89) | −1.2 (5.21) | [−2.8, 0.4] | −0.23 |
| Treatment Week 5 | | | | | |
| Placebo | 60 | −3.9 (4.88) | | | |
| aticaprant | 56 | −4.3 (6.07) | −0.4 (5.49) | [−2.1, 1.3] | −0.08 |
| Treatment Week 6 | | | | | |
| Placebo | 59 | −4.2 (5.04) | | | |
| aticaprant | 59 | −4.6 (6.23) | −0.4 (5.66) | [−2.1, 1.3] | −0.07 |

Negative change from baseline indicates improvement.
Negative change to Placebo indicates favorable aticaprant effect.
Negative effect size favors aticaprant; positive effect size favors Placebo.

Figure 28:
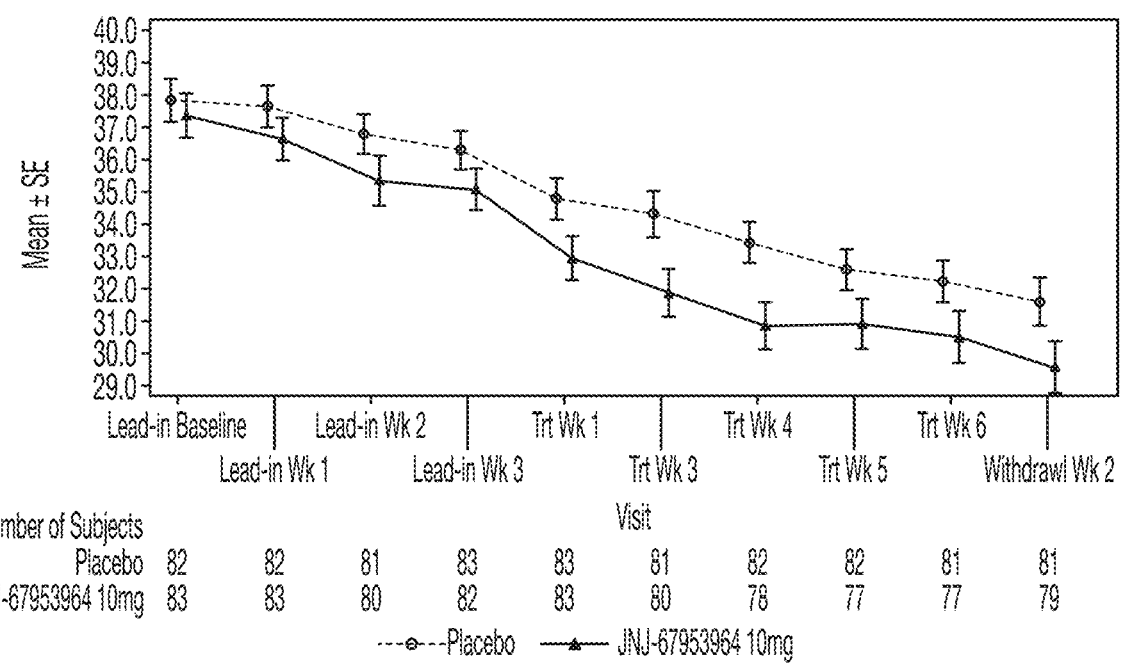
FIG. 28 is a line graph showing SHAPS total score: mean values (±SE) over time for the fITT analysis set.

Changes in SHAPS total score were analyzed with the same MMRM model used for MADRS total score. The estimated LS Mean difference with 80% 2-sided CI at treatment week 6 between aticaprant and placebo was −0.7 [−1.81, 0.41]. See, FIG. 17 and Tables 48 and 49 and FIG. 28. The corresponding p-value was 0.419.

TABLE 48

SHAPS Total Score: MMRM Results-Estimated LS Means and Comparison versus Placebo; eITT Analysis Set

| Analysis Visit Treatment | N | Mean (SD) | Mean (SD) | LSMean (SE) | Change from Baseline LSMean Difference (SE)\ Treatment Placebo | 60% Confidence Interval on Difference | p-value[a] |
|---|---|---|---|---|---|---|---|
| Treatment Week 1 | | | | | | | |
| Placebo | 61 | 35.5 (6.00) | −1.3 (3.17) | −0.9 (0.63) | | | |
| aticaprant | 60 | 34.5 (5.63) | −1.9 (4.30) | −1.7 (0.64) | −0.8 (0.86) | [−1.90, 0.31] | 0.3542 |
| Treatment Week 3 | | | | | | | |
| Placebo | 59 | 34.9 (6.09) | −2.2 (4.65) | −1.8 (0.64) | | | |
| aticaprant | 59 | 33.0 (6.39) | −3.4 (5.25) | −3.2 (0.64) | −1.4 (0.86) | [−2.53, −0.31] | 0.1005 |
| Treatment Week 4 | | | | | | | |
| Placebo | 60 | 33.7 (5.89) | −3.3 (4.47) | −2.9 (0.63) | | | |

TABLE 48-continued

SHAPS Total Score: MMRM Results-Estimated LS Means and Comparison versus Placebo; eITT Analysis Set

| Analysis Visit Treatment | N | Mean (SD) | Mean (SD) | LSMean (SE) | Change from Baseline LSMean Difference (SE)\ Treatment Placebo | 60% Confidence Interval on Difference | p-value[a] |
|---|---|---|---|---|---|---|---|
| aticaprant | 57 | 32.0 (6.24) | −4.5 (5.89) | −4.3 (0.64) | −1.4 (0.86) | [−2.48, −0.26] | 0.1131 |
| Treatment Week 5 | | | | | | | |
| Placebo | 60 | 33.1 (5.88) | −3.9 (4.88) | −3.5 (0.64) | | | |
| aticaprant | 56 | 32.4 (6.61) | −4.3 (6.07) | −4.0 (0.64) | −0.5 (0.87) | [−1.65, 0.57] | 0.5332 |
| Treatment Week 6 | | | | | | | |
| Placebo | 59 | 32.9 (6.04) | −4.2 (5.04) | −3.7 (0.64) | | | |
| aticaprant | 59 | 31.9 (6.60) | −4.6 (6.23) | −4.4 (0.64) | −0.7 (0.87) | [−1.81, 0.41] | 0.4188 |

[a]two-sided test for no difference between treatments from a MMRM model with subject as random effect; country, treatment, time and time-by-treatment interaction as factors; and baseline SHAPS total score as continuous covariate. An AR(1) variance-covariance matrix was employed.

TABLE 49

SHAPS Total Score: MMRM Results-Estimated LS Means and Comparison versus Placebo; fITT Analysis Set

| Analysis Visit Treatment | N | Mean (SD) | Mean (SD) | LSMean (SE) | Change from Baseline LSMean Difference (SE)\ Treatment Placebo | 60% Confidence Interval on Difference | p-value[a] |
|---|---|---|---|---|---|---|---|
| Treatment Week 1 | | | | | | | |
| Placebo | 83 | 34.8 (5.86) | −1.5 (3.57) | −1.0 (0.54) | | | |
| aticaprant | 83 | 32.9 (6.09) | −2.0 (4.05) | −1.9 (0.54) | −1.0 (0.72) | [−1.88, −0.02] | 0.1888 |
| Treatment Week 3 | | | | | | | |
| Placebo | 81 | 34.3 (6.36) | −2.2 (5.11) | −1.7 (0.54) | | | |
| aticaprant | 80 | 31.9 (6.54) | −3.2 (5.07) | −3.1 (0.54) | −1.4 (0.73) | [−2.32, −0.45] | 0.0580 |
| Treatment Week 4 | | | | | | | |
| Placebo | 82 | 33.4 (5.70) | −3.0 (4.41) | −2.5 (0.54) | | | |
| aticaprant | 78 | 30.8 (6.37) | −4.2 (5.70) | −4.1 (0.55) | −1.6 (0.73) | [−2.51, −0.63] | 0.0321 |
| Treatment Week 5 | | | | | | | |
| Placebo | 82 | 32.6 (5.63) | −3.8 (4.76) | −3.3 (0.55) | | | |
| aticaprant | 77 | 30.9 (6.76) | −4.3 (5.70) | −4.1 (0.55) | −0.8 (0.73) | [−1.71, 0.17] | 0.2912 |
| Treatment Week 6 | | | | | | | |
| Placebo | 81 | 32.2 (5.81) | −4.2 (4.98) | −3.7 (0.55) | | | |
| aticaprant | 77 | 30.5 (6.98) | −4.7 (5.91) | −4.5 (0.55) | −0.8 (0.73) | [−1.79, 0.10] | 0.2503 |

[a]two-sided test for no difference between treatments from a MMRM model with subject as random effect; country, treatment, time and time-by-treatment interaction as factors; and baseline SHAPS total score as continuous covariate. An AR(1) variance-covariance matrix was employed The estimated LS mean differences with 80% 2-sided CI at treatment week 6 between aticaprant and placebo was −0.8 [−1.79, 0.10]. The corresponding p-value was 0.250. See, FIGS. 17 and 18.

Full ITT Analysis Set

Similar trend was observed in fITT population and differences were larger in magnitude than those observed in eITT population. The effect size was 0.51 and 0.29, respectively. The mean (SD) baseline SHAPS total score at treatment baseline was 35.6 (5.67), ranging from 14 to 50. The mean changes from treatment baseline in SHAPS total score at treatment week 6 for fITT population were similar to changes in eITT: −4.7 (5.91) for aticaprant and −4.2 (4.98) for placebo. The observed effect size was 0.08. See, Table 50.

TABLE 50

SHAPS Total Score: Mean Changes to Placebo During the Treatment Period; fITT Analysis Set

| Analysis Visit Treatment | N | Mean Change from Baseline (SD) | Mean Change to Placebo (SD pooled) | 90% CI for Mean Change to Placebo | Effect Size |
|---|---|---|---|---|---|
| Treatment Week 1 | | | | | |
| Placebo | 83 | −1.5 (3.57) | | | |
| aticaprant | 83 | −2.0 (4.05) | −0.6 (3.82) | [−1.5, 0.4] | −0.15 |
| Treatment Week 3 | | | | | |
| Placebo | 81 | −2.2 (5.11) | | | |
| aticaprant | 80 | −3.2 (5.07) | −1.0 (5.09) | [−2.4, 0.3] | −0.20 |
| Treatment Week 4 | | | | | |
| Placebo | 82 | −3.0 (4.41) | | | |
| aticaprant | 78 | −4.2 (5.70) | −1.2 (5.08) | [−2.5, 0.1] | −0.23 |
| Treatment Week 5 | | | | | |
| Placebo | 82 | −3.8 (4.76) | | | |
| aticaprant | 77 | −4.3 (5.70) | −0.5 (5.24) | [−1.8, 0.9] | −0.09 |
| Treatment Week 6 | | | | | |
| Placebo | 81 | −4.2 (4.98) | | [−1.9, 1.0] | −0.08 |
| aticaprant | 77 | −4.7 (5.91) | −0.5 (5.45) | | |

Negative change from baseline indicates improvement.
Negative change to Placebo indicates favorable aticaprant effect.
Negative effect size favors aticaprant; positive effect size favors Placebo.

Changes in MADRS Total Score from Treatment Baseline to Treatment Week 6 by Anhedonia Level at Baseline Enriched ITT Analysis Set In subgroup of subjects with high anhedonia level (SHAPS total score≥38) at treatment baseline, n=53, larger differences between aticaprant and placebo at treatment Week 6 were observed than in subjects with low anhedonia level (20≤baseline SHAPS total score<38), n=65: −3.4 with 90% 2-sided CI of [−7.5, 0.7] and −0.9 with 90% 2-sided CI of [−4.2, 2.5], respectively (Table 51). The observed effect size was 0.38 and 0.11, respectively.

TABLE 51

MADRS (Montgomery-Åsberg Depression Rating Scale) Total Score: Mean Changes to Placebo During the Treatment Period by Anhedonia Level at Treatment Baseline; eITT Analysis Set

| Analysis Visit Treatment | N | Mean Change from Baseline (SD) | Mean Change to Placebo (SD pooled) | 90% CI for Mean Change to Placebo | Effect size |
|---|---|---|---|---|---|
| Low anhedonia Treatment Week 1 | | | | | |
| Placebo | 34 | −1.8 (3.43) | | | |
| aticaprant | 34 | −2.3 (5.03) | −0.5 (4.30) | [−2.2, 1.2] | −0.12 |
| Treatment Week 3 | | | | | |
| Placebo | 32 | −4.8 (5.70) | | | |
| aticaprant | 33 | −4.9 (5.99) | −0.1 (5.85) | [−2.5, 2.4] | −0.01 |
| Treatment Week 4 | | | | | |
| Placebo | 33 | −6.5 (6.16) | | | |
| aticaprant | 32 | −6.4 (7.40) | 0.0 (6.80) | [−2.8, 2.9] | 0.01 |
| Treatment Week 5 | | | | | |
| Placebo | 33 | −7.6 (6.80) | | | |
| aticaprant | 29 | −7.2 (6.46) | 0.3 (6.65) | [−2.5, 3.2] | 0.05 |
| Treatment Week 6 | | | | | |
| Placebo | 32 | −8.3 (8.25) | | | |
| aticaprant | 33 | −9.2 (8.01) | −0.9 (8.13) | [−4.2, 2.5] | −0.11 |
| High anhedonia Treatment Week 1 | | | | | |
| Placebo | 27 | −2.7 (4.08) | | | |
| aticaprant | 26 | −4.6 (5.25) | −1.8 (4.69) | [−4.0, 0.3] | −0.39 |
| Treatment Week 3 | | | | | |
| Placebo | 27 | −3.6 (6.35) | | | |
| aticaprant | 26 | −6.7 (6.83) | −3.0 (6.59) | [−6.1, 0.0] | −0.46 |
| Treatment Week 4 | | | | | |
| Placebo | 27 | −6.3 (7.34) | | | |
| aticaprant | 25 | −8.5 (7.26) | −2.2 (7.30) | [−5.6, 1.2] | −0.30 |
| Treatment Week 5 | | | | | |
| Placebo | 27 | −7.1 (7.67) | | | |
| aticaprant | 26 | −9.7 (8.18) | −2.6 (7.93) | [−6.3, 1.0] | −0.33 |
| Treatment Week 6 | | | | | |
| Placebo | 27 | −8.1 (9.01) | | | |
| aticaprant | 26 | −11.5 (8.95) | −3.4 (8.98) | [−7.5, 0.7] | −0.38 |

Low Anhedonia level (SHAPS Total Score at Treatment Baseline >=20 and <38), High Anhedonia level (SHAPS Total Score at Treatment Baseline >=38).
The MADRS Total Score ranges from 0 to 60, with higher scores indicating greater severity of depression.

Full ITT Analysis Set

A similar trend was observed in fITT population. The differences were larger in magnitude compared to eITT population: −4.6 with 90% 2-sided CI of [−8.4, −0.8] for subjects with high anhedonia level (n=63) and −2.3 with 90% 2-sided CI of [−5.0, 0.4] for subjects with low anhedonia level (n=94). See, Table 52. The observed effect size was 0.51 and 0.29, respectively.

TABLE 52

MADRS (Montgomery-Åsberg Depression Rating Scale) Total Score: Mean Changes to Placebo During the Treatment Period by Anhedonia Level at Treatment Baseline; fITT Analysis Set

| Analysis Visit Treatment | N | Mean Change from Baseline (SD) | Mean Change to Placebo (SD pooled) | 90% CI for Mean Change to Placebo | Effect size |
|---|---|---|---|---|---|
| Low anhedonia Treatment Week 1 | | | | | |
| Placebo | 49 | −1.3 (4.17) | | | |
| aticaprant | 52 | −2.4 (4.59) | −1.0 (4.39) | [−2.5, 0.4] | −0.24 |
| Treatment Week 3 | | | | | |
| Placebo | 47 | −3.6 (6.04) | | | |
| aticaprant | 49 | −4.1 (6.67) | −0.5 (6.37) | [−2.7, 1.7] | −0.08 |
| Treatment Week 4 | | | | | |
| Placebo | 48 | −4.9 (6.53) | | | |
| aticaprant | 48 | −6.4 (6.77) | −1.5 (6.65) | [−3.8, 0.8] | −0.23 |
| Treatment Week 5 | | | | | |
| Placebo | 48 | −6.6 (6.82) | | | |
| aticaprant | 45 | −7.3 (6.90) | −0.7 (6.86) | [−3.1, 1.7] | −0.10 |
| Treatment Week 6 | | | | | |
| Placebo | 47 | −6.5 (8.11) | | | |
| aticaprant | 47 | −8.8 (7.48) | −2.3 (7.80) | [−5.0, 0.4] | −0.29 |
| High anhedonia Treatment Week 1 | | | | | |
| Placebo | 34 | −2.4 (3.71) | | | |
| aticaprant | 30 | −4.4 (5.04) | −2.0 (4.38) | [−3.8, −0.1] | −0.45 |
| Treatment Week 3 | | | | | |
| Placebo | 34 | −3.1 (7.17) | | | |
| aticaprant | 30 | −6.9 (6.66) | −3.8 (6.94) | [−6.7, −0.9] | −0.54 |
| Treatment Week 4 | | | | | |
| Placebo | 34 | −4.8 (7.75) | | | |
| aticaprant | 29 | −8.6 (7.32) | −3.8 (7.56) | [−7.0, −0.6] | −0.50 |
| Treatment Week 5 | | | | | |
| Placebo | 34 | −6.2 (7.72) | | | |
| aticaprant | 30 | −10.2 (8.04) | −4.0 (7.87) | [−7.3, −0.7] | −0.51 |
| Treatment Week 6 | | | | | |
| Placebo | 34 | −6.8 (9.30) | | | |
| aticaprant | 29 | −11.3 (8.69) | −4.6 (9.03) | [−8.4, −0.8] | −0.51 |

Low Anhedonia level (SHAPS Total Score at Treatment Baseline >=20 and <38), High Anhedonia level (SHAPS Total Score at Treatment Baseline >=38).
The MADRS Total Score ranges from 0 to 60, with higher scores indicating greater severity of depression.

This data illustrates that segmentation into high vs low anhedonia had a benefit for treating MDD: higher treatment effect for Aticaprant. Further, the placebo response was lower in patients with high anhedonia, as compared to low anhedonia.

Change from Treatment Baseline in CGI-S Total Score at Treatment

TABLE 53

Change from Treatment Baseline in CGI-S Total Score at Treatment

| End Point Values | Placebo | aticaprant 10 milligrams (mg) |
|---|---|---|
| Number of subjects analyzed | 59 | 59 |
| Units: Scores on a scale | | |
| Measure Type: Arithmetic Mean (SD) | −0.76 ± 0.858 | −0.92 ± 1.039 |

Change from Treatment Baseline in SMDDS Total Score at Treatment Week 6

TABLE 54

Change from Treatment Baseline in SMDDS Total Score at Treatment Week

| End point values | Placebo | aticaprant 10 milligrams (mg) |
|---|---|---|
| Number of subjects analyzed | 59 | 59 |
| Units: Scores on a scale | | |
| Measure Type: Arithmetic Mean (SD) | −8.49 ± 9.567 | −8.03 ± 9.957 |

Number of Subjects with SATE Score at Treatment Week 6

TABLE 55

Number of Subjects with SATE Score at Treatment Week 6

| End point values | Placebo | aticaprant 10 milligrams (mg) |
|---|---|---|
| Number of subjects analyzed | 61 | 60 |
| Units: subjects | | |
| Overall Depression (Got worse) (n = 40, 30) | 1 | 0 |
| Overall Depression (Not changed) (n = 40, 30) | 12 | 9 |
| Overall Depression (Improved) (n = 40, 30) | 27 | 21 |
| Depression Worsened (Slightly worse) (n = 1, 0) | 1 | 0 |
| Depression Worsened (Much worse) (n = 1, 0) | 0 | 0 |
| Depression Worsened (Very much worse) (n = 1, 0) | 0 | 0 |
| Depression Slightly improved (n = 27, 21) | 13 | 15 |
| Depression Much improved (n = 27, 21) | 11 | 6 |
| Depression Very Much Improved (n = 27, 21) | 3 | 0 |

Change from Treatment Baseline in HAM-A6 Total Score at Treatment Week

TABLE 56

Change from Treatment Baseline in HAM-A6 Total Score at Treatment Week 6

| End point values | Placebo | aticaprant 10 milligrams (mg) |
|---|---|---|
| Number of subjects analyzed | 59 | 59 |
| Units: scores on a scale | | |
| Measure Type: Arithmetic Mean (SD) | −2.19 ± 2.837 | −2.73 ± 2.651 |

These data show a greater improvement in HAMA6 score in aticaprant treated patients vs. placebo.

Change from Treatment Baseline in Structured Interview Guide for the SIGH-A Score at Treatment Week 6

TABLE 57

Change from Treatment Baseline in Structured Interview Guide for the SIGH-A Score at Treatment Week 6

| End point values | Placebo | aticaprant 10 milligrams (mg) |
|---|---|---|
| Number of subjects analyzed | 59 | 59 |
| Units: scores on a scale | | |
| Measure Type: Arithmetic Mean (SD) | −5.37 ± 6.549 | −5.85 ± 5.369 |

Maximum Plasma Concentration ($C_{max}$) of Aticaprant $C_{max}$ is defined as maximum plasma concentration of aticaprant. The eITT population included all enrolled lead-in placebo non-responders who were randomized into a treatment period, received at least 1 dose of study medication, and had at least 1 post-baseline MADRS assessment during the treatment period. Here 'N' (number of subjects analyzed) includes the number of subjects evaluable for this endpoint. Here 'n' (number analyzed) included all subjects evaluable for specified time point categories.

TABLE 58

$C_{max}$ of Aticaprant (10 mg)

| Number of subjects analyzed | 58 |
|---|---|
| Units: nanograms per milliliter (ng/ml) | |
| Measure Type: Arithmetic Mean (SD) | |
| Week 1 (n = 56) | 32.7 ± 10.9 |
| Week 3 (n = 56) | 33.5 ± 11.1 |
| Week 6 (n = 56) | 34.3 ± 11.1 |

No statistical analyses of this end point.

(iii) Safety Endpoints

Overall, in full safety analysis set 40/85 (47.1%) of subjects in the aticaprant group and 30/84 (35.7%) of subjects in the placebo group experienced at least one TEAE during the treatment period. See, Table 59.

TABLE 59

Overall Summary of Treatment-Emergent Adverse Events During the Treatment Period; Full Safety Analysis Set

| | Placebo (N = 84) n (%) | aticaprant 10 mg (N = 85) n (%) | Overall (N = 169) n (%) |
|---|---|---|---|
| Subjects with 1 or more TEAE | 30 (35.7) | 40 (47.1) | 70 (41.4) |
| Total subjects affected by non-serious adverse events | 9 (10.7%) | 23 (27.1%) | |
| Subjects with drug-related TEAE [a] | 13 (15.5) | 20 (23.5) | 33 (19.5) |
| Subjects with TEAE leading to death | 0 | 0 | 0 |
| Subjects with 1 or more serious TEAE | 1 (1.2) | 0 | 1 (0.6) |
| Subjects with TEAE leading to discontinuation of agent | 1 (1.2) | 1 (1.2) | 2 (1.2) |

Subjects are presented by the treatment received during the Treatment period.
[a] Drug relationships of possible, probable, and very likely are included in this category.

The most common TEAEs during the treatment period were headache (experienced by 10/85 subjects—11.8% in the aticaprant group and by 6/84 subjects—7.1% in the placebo group) and diarrhea (experienced by 7/85 subjects—8.2% in the aticaprant group and by 2/84 subjects—2.4% in the placebo group). See, Table 60.

TABLE 60

Treatment-Emergent Adverse Events by Body System or Organ Class and Dictionary-Derived Term in >= 5% of Subjects in Either Treatment Group During the Treatment Period; Full Safety Analysis Set

| Body System Preferred Term | Placebo (N = 84) n (%) | aticaprant 10 mg (N = 85) n (%) | Overall (N = 169) n (%) |
|---|---|---|---|
| Total no. Subjects with Adverse Events | 30 (36) | 40 (47) | 70 (41) |
| Infections And Infestations | 9 (11) | 13 (15) | 22 (13) |
| Nasopharyngitis | 2 (2) | 5 (6) | 7 (4) |
| Nervous System Disorders | 9 (11) | 13 (15) | 22 (13) |
| Headache | 6 (7) | 10 (12) | 16 (10) |
| Gastrointestinal Disorders | 9 (11) | 12 (14) | 21 (12) |
| Diarrhea | 2 (2) | 7 (8) | 9 (5) |
| Skin And Subcutaneous Tissue Disorders | 3 (4) | 6 (7) | 9 (5) |
| Pruritus | 0 | 5 (6) | 5 (3) |

Percentages calculated with the number of subjects in each group as denominator. Reported dictionary version: MedDRA 22.1. Subjects are presented by the treatment received during the Treatment period.

There were 2 subjects in total who discontinued during the treatment period due to treatment-emergent adverse events: 1 subject in the aticaprant 10 group due to diarrhea, nausea, vomiting and headache, and another subject in placebo group due to acute calculous cholecystitis.

Overall, 17/169 subjects experienced TEAEs of special interest during the treatment period: 13/85 (15.3%) in the aticaprant group and 4/84 (4.8%) in the placebo group. The most common treatment-emergent adverse events during the treatment phase were headache and diarrhea. The most common TEAE of special interest during the treatment period were diarrhea and pruritus (experienced by 5/85 subjects-5.9% in the aticaprant group and by 0/84 subjects in the placebo group). Further 1 patient in the placebo group (1.19%) experienced acute cholecystitis, as compared to 0 patients receiving aticaprant. See, Table 61.

TABLE 61

Treatment-Emergent Adverse Events of Special Interest During the Treatment Period; Full Safety Analysis Set

| Body System Preferred Term | Placebo (N = 84) | aticaprant 10 mg (N = 85) n (%) | Overall (N = 169) n (%) |
|---|---|---|---|
| Total no. Subjects with Adverse Events of Special Interest | 4 (4.8) | 13 (15.3) | 17 (10.1) |
| Gastrointestinal Disorders | 4 (4.8) | 9 (10.6) | 13 (7.7) |
| deaths causally related to treatment/all | | | |
| Diarrhea | 2 (2.4) | 7 (8.2) | 9 (5.3) |
| Abdominal Pain Upper | 2 (2.4) | 0 | 2 (1.2) |
| Dyspepsia | 1 (1.2) | 1 (1.2) | 2 (1.2) |
| Abdominal Pain | 0 | 1 (1.2) | 1 (0.6) |
| Skin And Subcutaneous Tissue Disorders | 0 | 5 (5.9) | 5 (3.0) |
| Pruritus | 0 | 5 (5.9) | 5 (3.0) |

Percentages calculated with the number of subjects in each group as denominator. Reported dictionary version: MedDRA 22.1. Subjects are presented by the treatment received during the Treatment period.

Two serious adverse events occurred. One subject in the placebo group experienced acute calculous cholecystitis during the treatment period and other subject suicidal ideation during the lead-in period. Both subjects discontinued due to these AEs.

No deaths were reported.

(iv) Anhedonia Analysis

Patients in the larger fITT group maintained baseline level of depression and anhedonia severity consistent with the eITT group. See, Tables 62-64.

TABLE 62

Frequency of Subjects with Anhedonia at Treatment Baseline; fITT Analysis Set

|  | N | No Anhedonia (SHAPS Total Score < 20) | Anhedonia (SHAPS Total Score >= 20) |
| --- | --- | --- | --- |
| Baseline/Day 22 |  |  |  |
| Placebo | 83 | 0 | 83 (100%) |
| aticaprant | 83 | 1 (1.2%) | 82 (98.8%) |
| Total | 166 | 1 (0.6%) | 165 (99.4%) |

Anhedonia classification is based on calculated SHAPS total score at Visit Day 22

Figure 29:
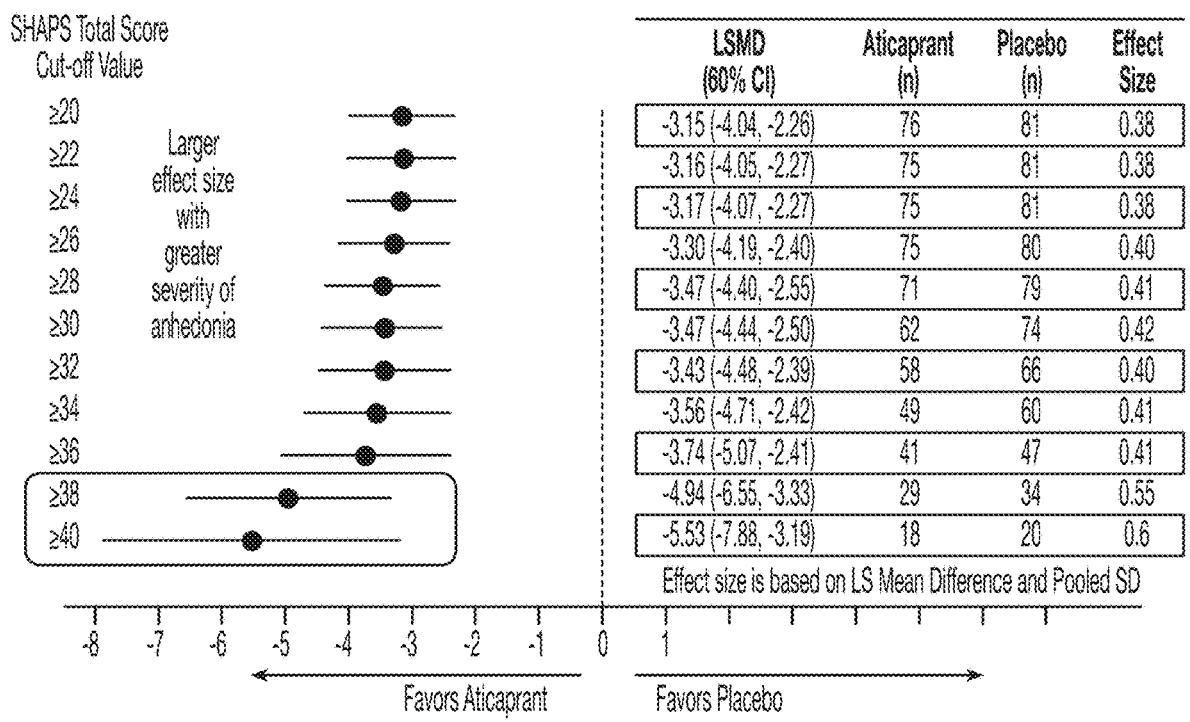
FIG. 29 illustrates the MADRS change from baseline by anhedonia severity.

The results illustrate that treatment effect is larger in patients with more anhedonia at baseline. See, FIG. 29.

TABLE 63

Frequency of Subjects with Different Level of Anhedonia at Treatment Baseline and Treatment Week 6; eITT Analysis Set

|  | N | No Anhedonia (SHAPS Total Score < 20) | Low Level of Anhedonia Score < 20) Total Score < 38) | High Level of Anhedonia (20 <= SHAPS Score >= 38) |
| --- | --- | --- | --- | --- |
| Treatment Baseline |  |  |  |  |
| Placebo | 61 | 0 | 34 (55.74%) | 27 (44.26%) |
| aticaprant | 60 | 0 | 34 (56.67%) | 26 (43.33%) |
| Total | 121 | 0 | 68 (56.2%) | 53 (43.8%) |
| Treatment Week 6 |  |  |  |  |
| Placebo | 59 | 0 | 46 (77.97%) | 13 (22.03%) |
| aticaprant | 59 | 3 (5.08%) | 48 (81.36%) | 8 (13.56%) |
| Total | 118 | 3 (2.54%) | 94 (79.66%) | 21 (17.8%) |

Anhedonia classification is based on re-calculated SHAPS total score at analysis visits Treatment Baseline and Treatment Week 6.

TABLE 64

Frequency of Subjects with Different Level of Anhedonia at Treatment Baseline and Treatment Week 6; fITT Analysis Set

|  | N | No Anhedonia (SHAPS Total Score < 20) | Low Level of Anhedonia (20 >= SHAPS Total Score < 38) | High Level of Anhedonia (SHAPS Total Score >= 38) |
| --- | --- | --- | --- | --- |
| Treatment Baseline |  |  |  |  |
| Placebo | 83 | 0 | 49 (59.04%) | 34 (40.96%) |
| aticaprant | 83 | 1 (1.2%) | 52 (62.65%) | 30 (36.14%) |
| Total | 166 | 1 (0.6%) | 101 (60.84%) | 64 (38.55%) |
| Treatment Week 6 |  |  |  |  |
| Placebo | 81 | 0 | 66 (81.48%) | 15 (18.52%) |
| aticaprant | 77 | 7 (9.09%) | 62 (80.52%) | 8 (10.39%) |
| Total | 158 | 7 (4.43%) | 128 (81.01%) | 23 (14.56%) |

Anhedonia classification is based on re-calculated SHAPS total score at analysis visits Treatment Baseline and Treatment Week 6.

Figure 30A:
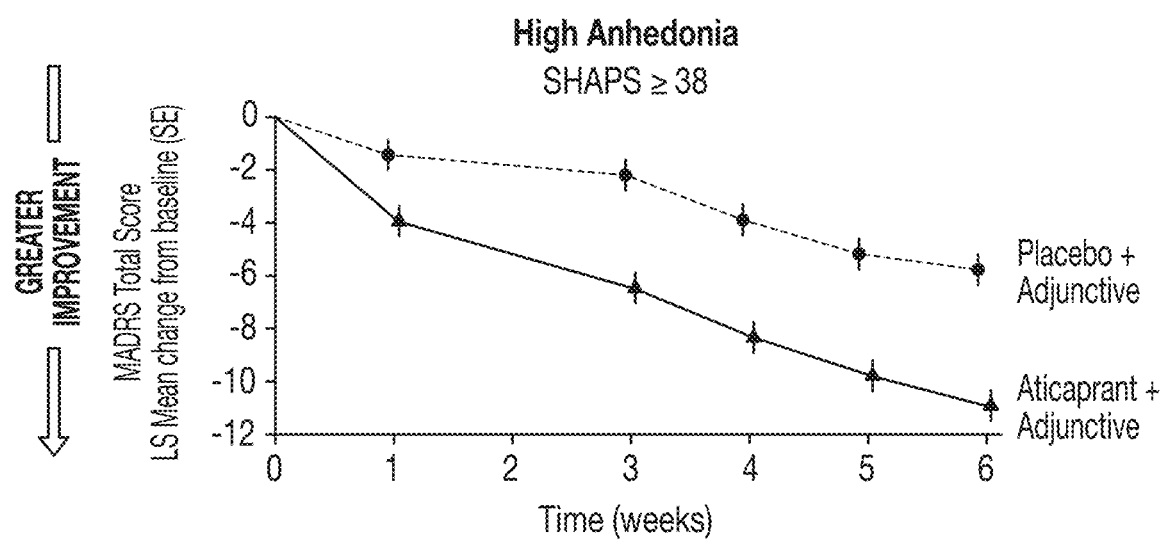
FIG. 30-A is a line graph showing MADRS change from baseline for patients with high anhedonia, i.e., SHAPS≥38.
Figure 30B:
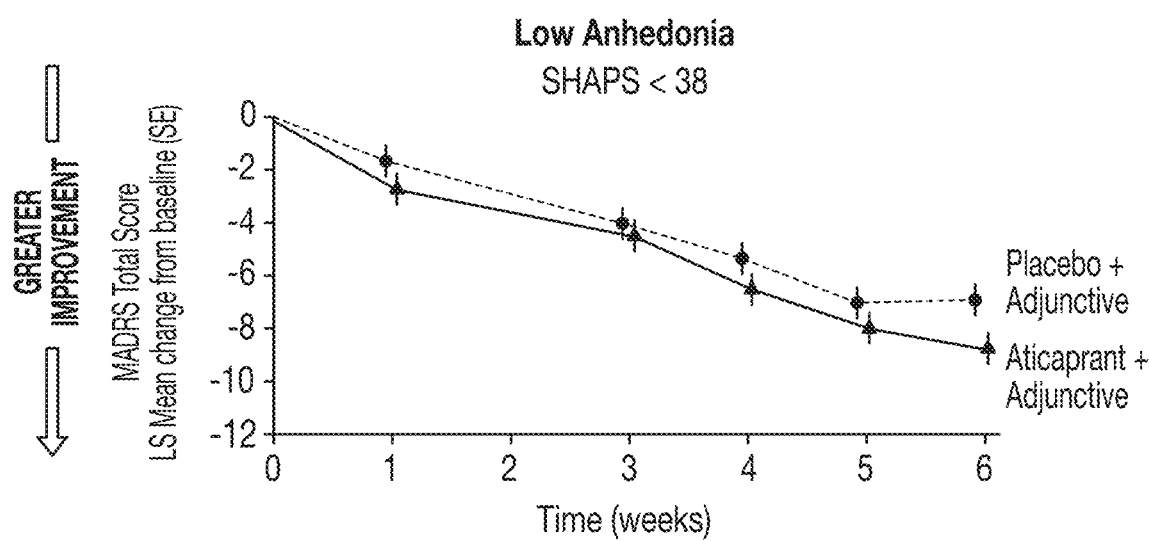
Figure 31:
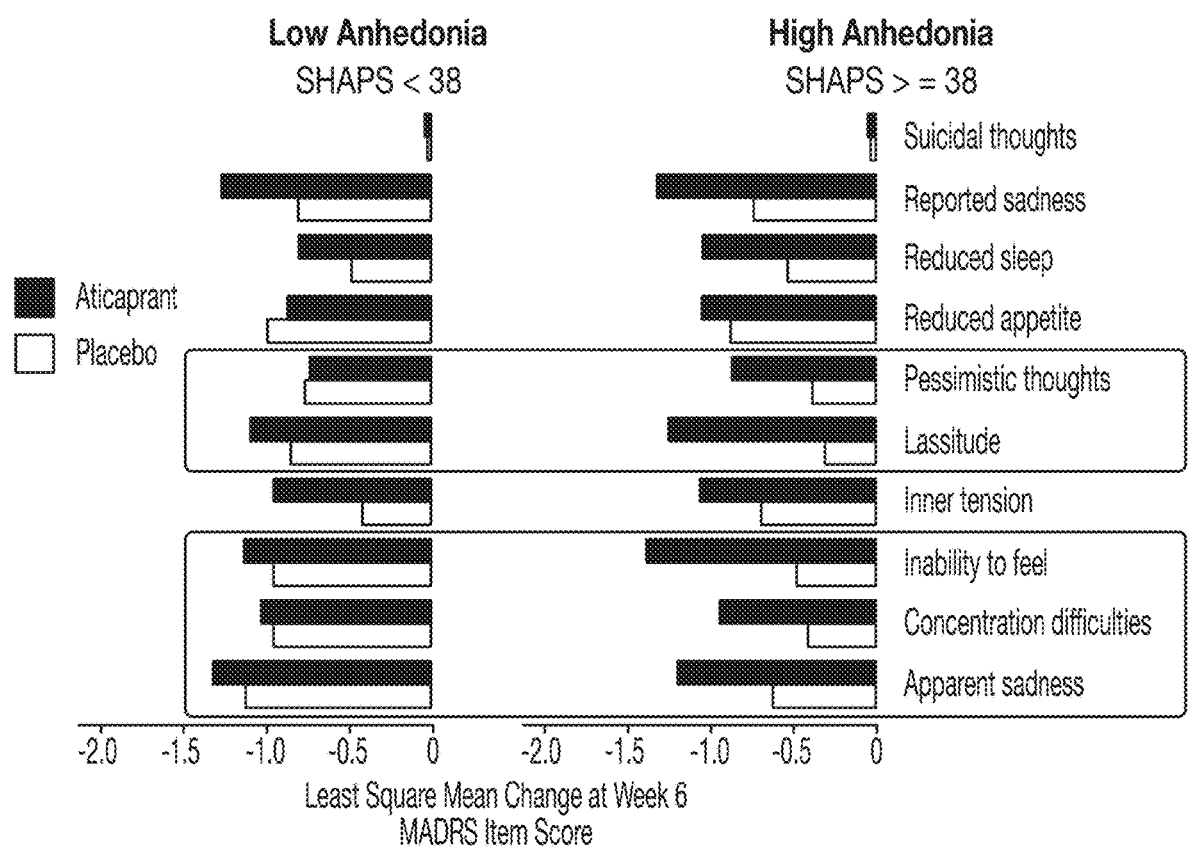
FIG. 31 is bar graph showing the comparison of MADRS in patients having low and high anhedonia.

The results illustrate that the treatment effect is larger in patients with more anhedonia at baseline. See, FIGS. 30-A and 30-B. In FIG. 30-A, i.e., the high anhedonia group, the placebo+oral antidepressant group shows less placebo response as compared to the low anhedonia group in FIG. 30-B. Similarly the treatment effect of the aticaprant+oral antidepressant group is higher in the high anhedonia group as compared to the low anhedonia group. Overall the effect size is larger at every single time point (from week 1 onwards) in the high anhedonia group. The LSMD in the high anhedonia group is more than double that of the low anhedonia group at week 6. Further, when looking at the symptom level, greater improvement in items related to anhedonia and dysphoria in subgroup with high anhedonia vs low anhedonia. See, FIG. 31.

(v) Weight Change

At the lead-in baseline timepoint, the mean weight for subjects in the placebo group was 76.17 kg compared to 78.66 in the aticaprant group. After 6 weeks in the double-blind treatment phase, the mean weight in the placebo group was 75.75 kg compared to 78.57 kg in the aticaprant group. This indicates that the weight in both groups remained relatively stable over the 6-week double blind treatment period. This is unexpected because other adjunctive treatments for MDD result in a mean weight increase. See, Thase M, et al. J Clin Psych. 2015: 76 (9), 1224-1231; Thase, J Clin Psych. 2015, 76 (9): 1232-1240; El Khalili, Int J Neuropsychopharmacol. 2010, 13, 917-932; Marcus, J. Clin. Psychopharmacol. 2008, 28:156-165; Berman, J. Clin. Psychiatry 2007; 68:843-853; Berman, American College of Neuropsychopharmacology, 2008, Annual Meeting Abstracts (Scottsdale, Ariz, Dec. 7-11, 2008). Nashville, Tenn, ACNP, 2008; Earley, American College of Neuropsychopharmacology, 2007, Annual Meeting Abstracts (Boca Raton, Fla, Dec. 9-13, 2007). Nashville, TN, ACNP, 2007). See, Table 65.

TABLE 65

Mean weight by treatment group (kg)

|  | Placebo n = 84 | Aticaprant n = 85 |
| --- | --- | --- |
| Screening, mean (SE) | 76.39 (1.61) | 78.42 (1.65) |
| Lead-in Baseline, mean (SE) | 76.17 (1.61) | 78.66 (1.65) |
| Withdrawal Baseline, mean (SE) | 75.75 (1.62) | 78.57 (1.71) |
| Absolute Change (Withdrawal-Lead-in) | −0.42 | −0.09 |
| Relative % Change | −0.55% | −0.11% |

(vi) Completion Rate

Patients who passed the screening phase entered a lead in phase followed by a double-blind phase. Patients who responded to placebo during the lead in phase were labelled as non-responders. Patients who did not respond to placebo were labelled as non-responders. The double-blind treatment phase then continued for an additional 6 weeks, after which patients entered a withdrawal period.

Of the 121 subjects in the enriched population (60 in aticaprant and 61 in placebo group), 117 (96.7%) completed the study. The overall completion rate for the full ITT analysis set is 95%. This contrasts with completion rates of approximately 85% for studies of adjunctive aripiprazole (Pae, CNS Drugs, 2011; 25, 109-127) and 45-62% for adjunctive quetiapine (El Khalili cited above). In total 4 subjects (3.3%) discontinued the study: 2 subjects in placebo and 2 subjects in aticaprant treatment group. See, Tables 66 and 67.

TABLE 66

Completion/Early Withdrawal Information; eITT Analysis Set

|  | Placebo (N = 61) | aticaprant 10 mg (N = 60) | Total (N = 121) |
|---|---|---|---|
| *Subject Completed Treatment/Trial* | | | |
| Completed | 59 (96.7%) | 58 (96.7%) | 117 (96.7%) |
| Withdrawn | 2 (3.3%) | 2 (3.3%) | 4 (3.3%) |
| *Reason For Withdrawal/Termination* | | | |
| Lack of Efficacy | 0 | 1 (1.7%) | 1 (0.8%) |
| Non-compliance with drug | 0 | 1 (1.7%) | 1 (0.8%) |
| Withdrawal by subject | 1 (1.6%) | 0 | 1 (0.8%) |
| Other | 1 (1.6%) | 0 | 1 (0.8%) |

Percentages calculated with the number of subjects in each group as denominator.

TABLE 67

Completion/Early Withdrawal Information; Full Safety Analysis Set

|  | Placebo (N = 84) | aticaprant 10 mg (N = 85) | Total (N = 169) |
|---|---|---|---|
| *Subject Completed Treatment/Trial* | | | |
| Completed | 81 (96.4%) | 79 (92.9%) | 160 (94.7%) |
| Withdrawn | 3 (3.6%) | 6 (7.1%) | 9 (5.3%) |
| *Reason For Withdrawal/Termination* | | | |
| Adverse event | 1 (1.2%) | 1 (1.2%) | 2 (1.2%) |
| Lack of Efficacy | 0 | 2 (2.4%) | 2 (1.2%) |
| Non-compliance with drug | 0 | 1 (1.2%) | 1 (0.6%) |
| Protocol deviation | 0 | 1 (1.2%) | 1 (0.6%) |
| Withdrawal by subject | 1 (1.2%) | 0 | 1 (0.6%) |
| Other | 1 (1.2%) | 1 (1.2%) | 2 (1.2%) |

Percentages calculated with the number of subjects in each group as denominator.

(vii) Sexual Functioning

Impairments in sexual functioning is a common side effect of antidepressant treatment and can be very upsetting to patients and their sexual partners. Major depression itself is associated with increased sexual dysfunction, and many of the pharmacological treatments are known to worsen sexual functioning even further. In a large survey of nearly 5000 patients in France, it was estimated that in untreated patients with MDD, the prevalence of sexual dysfunction was 65%. The prevalence of sexual dysfunction increased to 71% for patients treated with antidepressant therapy.

Sexual pleasure is an important component of hedonic tone. The brain reward circuitry is controlled by several areas: nucleus accumbens, ventral tegmental area and the amygdala. It is hypothesized that treatment with kappa opioid receptors may restore the normal homeostatic balance in patients with overactivation. Treatment with aticaprant could potentially improve symptoms of anhedonia. Other symptoms associated with the reward circuitry includes: sexual pleasure, lack of interest and lack of enjoyment.

Patients had their sexual functioning measured using a standard, well accepted rating scale: ASEX. See, Table 68.

TABLE 68

ASEX scores by treatment group

|  | Placebo n = 84 | Aticaprant n = 85 |
|---|---|---|
| Baseline | 22.04 | 21.26 |
| Endpoint | 21.36 | 19.79 |
| Absolute Change | −0.68 | −1.47 |
| Relative % Change | −3.09% | −6.91% |

Figure 32:
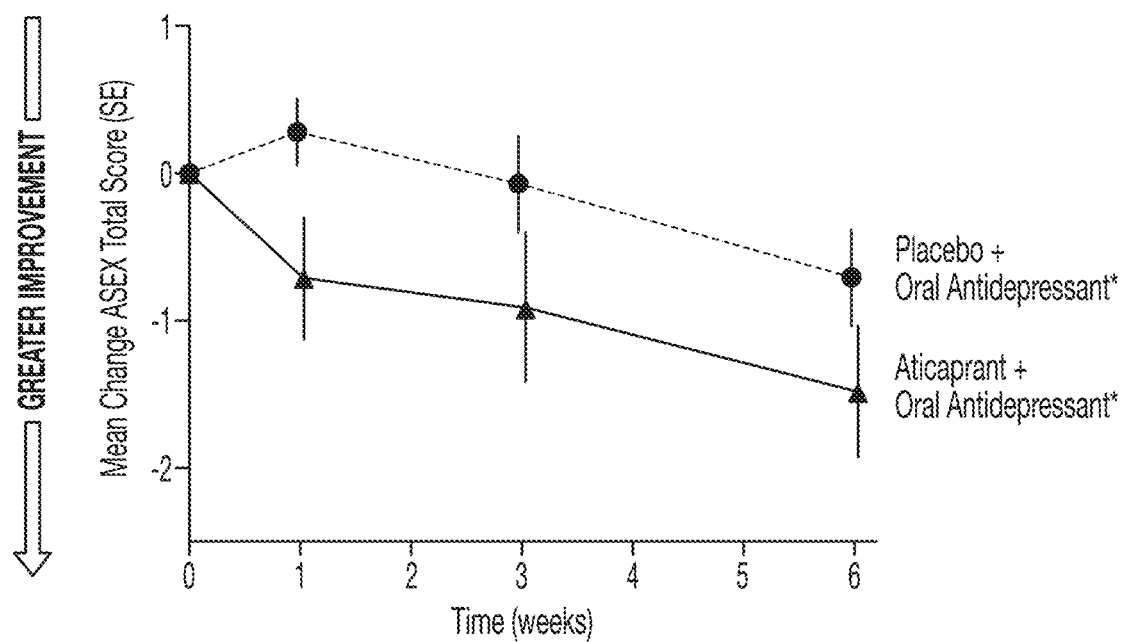
FIG. 32 is a line graph showing the ASEX total score mean change from baseline.

The mean change from treatment baseline (SD) in ASEX total score to week 6 was −1.5 (4.02) points for aticaprant compared to −0.7 (2.98) points for placebo. A lower score on the ASEX indicates improvement. The score reduction at week 6 was greater in the aticaprant group compared to placebo. This is unexpected because adjunctive treatments with other agents are expected to worsen sexual functioning, i.e., increase in ASEX score over time. See, FIG. 32.

Figure 33:
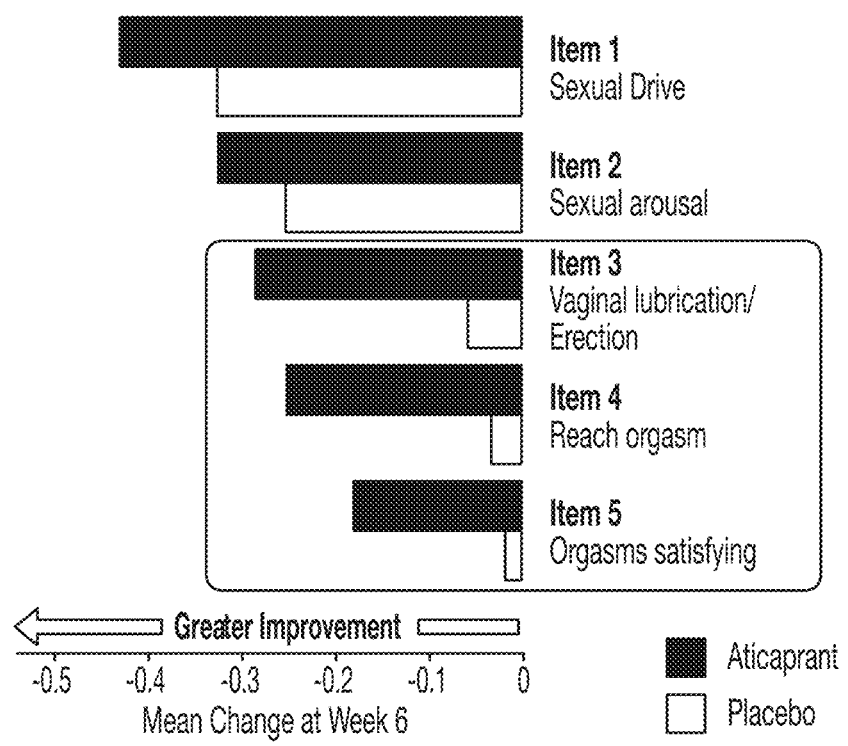
FIG. 33 is a bar graph showing ASEX item level change total score mean change from baseline.

Patients receiving aticaprant had notable improvements in sexual functioning. An examination of individual item level changes was also conducted and revealed that the greatest changes were seen in items related to consummatory pleasure: orgasm satisfying, reach orgasm and vaginal lubrication/erection. Most of the improvements seen in items 3, 4 and 5 of FIG. 33.

(viii) Onset of Effect

Figure 20A:
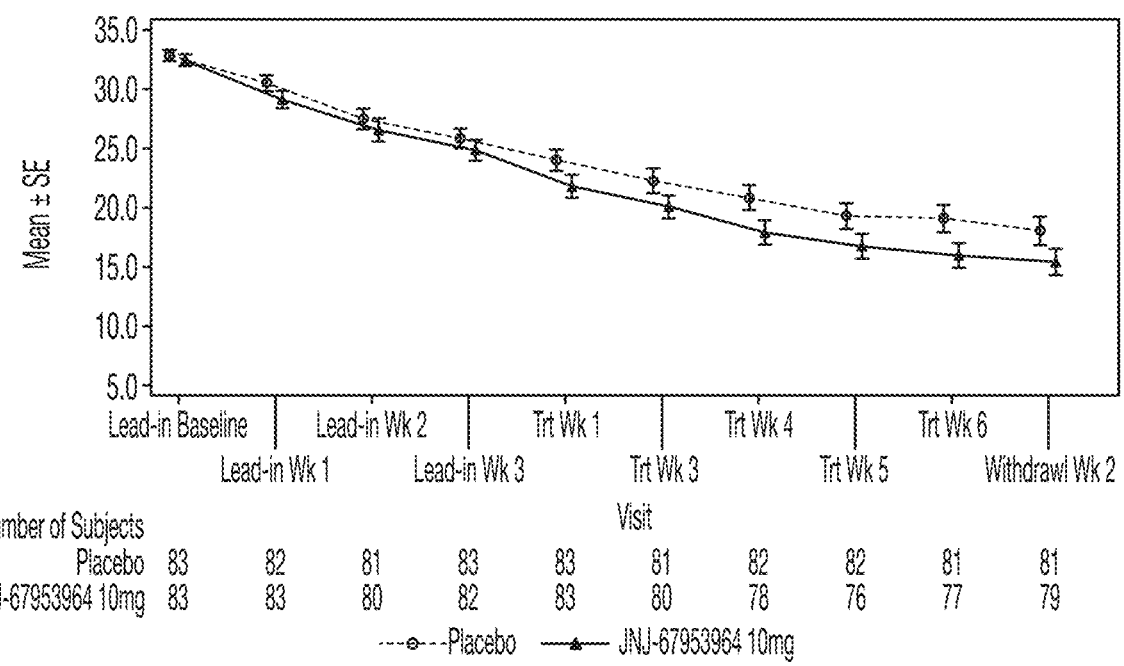
FIG. 20-A is a line graph showing MADRS total score: mean values (±SE) over time for the full intent-to-treat (fITT) analysis set.
Figure 20B:
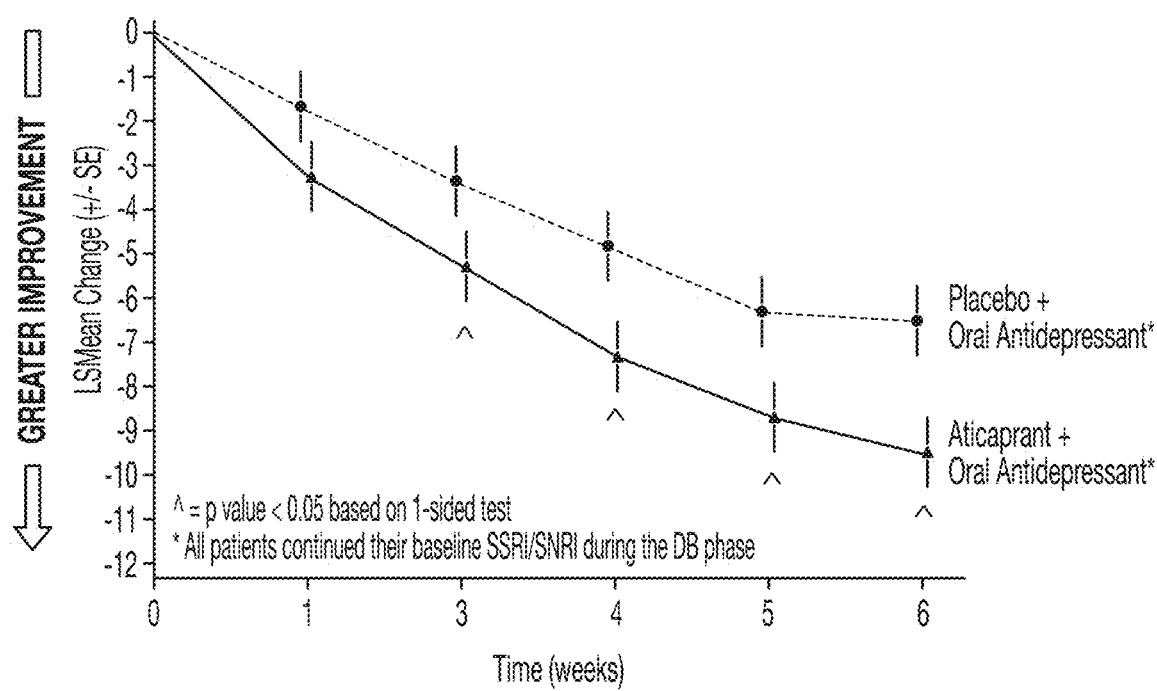

The onset of effect for aticaprant can be estimated from the study. FIG. 20-B depicts the least squares mean change from baseline. A significant treatment effect favoring aticaprant was seen as early as week 3. At this point, aticaprant showed a statistically superior effect compared to placebo.

What is claimed is:

1. A method of treating major depressive disorder in a human patient, comprising administering an effective amount of crystalline aticaprant of Form I, II, or III to the human patient,
wherein:
crystalline Form I of aticaprant is characterized by four or more x-ray diffraction pattern peaks at 2θ (±0.2) of 4.6°, 17.3°, 17.4°, 18.0°, and 24.0°;
crystalline Form II of aticaprant is characterized by four or more x-ray diffraction pattern peaks at 2θ (±0.2) of 3.1°, 19.0°, 24.0°, 24.3°, and 26.2°; and
crystalline Form III of aticaprant is characterized by four or more x-ray diffraction pattern peaks at 2θ (±0.2) of 4.1°, 9.0°, 17.6°, 18.0°, and 21.4°;
wherein aticaprant has the following structure:

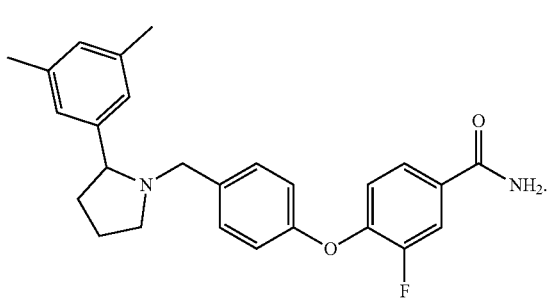 [SMILES: Cc1cc(C)cc(C2CCCN2Cc2ccc(Oc3ccc(C(N)=O)cc3F)cc2)c1]

2. The method of claim 1, wherein the crystalline aticaprant is crystalline Form I of aticaprant that is characterized by four or more x-ray diffraction pattern peaks at 2θ (±0.2) of 4.6°, 17.3°, 17.4°, 18.0°, and 24.0°.

3. The method of claim 2, wherein the crystalline Form I of aticaprant is characterized by a differential scanning calorimetry thermogram comprising one endotherm at about 92.9° C.

4. The method of claim 1, wherein the crystalline aticaprant is a crystalline Form II of aticaprant that is characterized by four or more x-ray diffraction pattern peaks at 2θ (±0.2) of 3.1°, 19.0°, 24.0°, 24.3°, and 26.2°.

5. The method of claim 4, wherein the crystalline Form II of aticaprant is characterized by a differential scanning calorimetry thermogram comprising one or both endotherms at about 74.7° C. and about 96.2° C.

6. The method of claim 1, wherein the crystalline aticaprant is a crystalline Form III of aticaprant that is characterized by four or more x-ray diffraction pattern peaks at 2θ (±0.2) of 4.1°, 9.0°, 17.6°, 18.0°, and 21.4°.

7. The method of claim 6, wherein the crystalline Form III of aticaprant is characterized by a peak temperature ($T_m$) at about 121° C.

8. The method of claim 1, wherein the crystalline form of aticaprant is anhydrous.

9. The method of claim 1, further comprising adjunctive treatment with an effective amount of one or more antidepressants.

10. The method of claim 9, wherein the one or more antidepressants is a selective serotonin reuptake inhibitor, serotonin-norepinephrine reuptake inhibitor, or a combination thereof.

11. The method of claim 1, wherein the effective amount of the crystalline Form I, II, or III of aticaprant is between about 2 mg and about 35 mg, between about 5 mg and about 10 mg, about 5 mg, or about 10 mg.

12. The method of claim 1, wherein the crystalline Form I, II, or III of aticaprant is administered orally once daily.

13. The method of claim 1, wherein the patient has anhedonia.

14. A method of treating major depressive disorder in a human patient, comprising administering an effective amount of crystalline S-aticaprant of Form I, II, or III to the human patient,
wherein:
crystalline Form I of S-aticaprant is characterized by four or more x-ray diffraction pattern peaks at 2θ (±0.2) of 4.6°, 17.3°, 17.4°, 18.0°, and 24.0°;
crystalline Form II of S-aticaprant is characterized by four or more x-ray diffraction pattern peaks at 2θ (±0.2) of 3.1°, 19.0°, 24.0°, 24.3°, and 26.2°; and
crystalline Form III of S-aticaprant is characterized by four or more x-ray diffraction pattern peaks at 2θ (±0.2) of 4.1°, 9.0°, 17.6°, 18.0°, and 21.4°;
wherein S-aticaprant has the following structure:

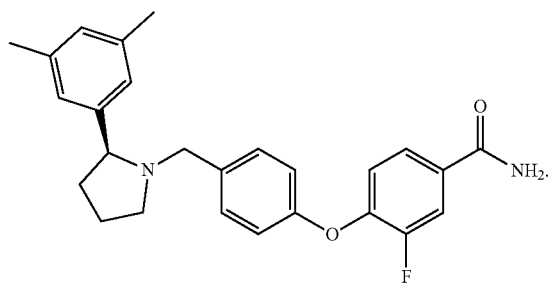 [SMILES: Cc1cc(C)cc([C@@H]2CCCN2Cc2ccc(Oc3ccc(C(N)=O)cc3F)cc2)c1]

15. The method of claim 14, wherein the crystalline S-aticaprant is crystalline Form I of S-aticaprant that is characterized by four or more x-ray diffraction pattern peaks at 2θ (±0.2) of 4.6°, 17.3°, 17.4°, 18.0°, and 24.0°.

16. The method of claim 15, wherein the crystalline Form I of S-aticaprant is characterized by a differential scanning calorimetry thermogram comprising one endotherm at about 92.9° C.

17. The method of claim 14, wherein the crystalline S-aticaprant is a crystalline Form II of S-aticaprant that is characterized by four or more x-ray diffraction pattern peaks at 2θ (±0.2) of 3.1°, 19.0°, 24.0°, 24.3°, and 26.2°.

18. The method of claim 17, wherein the crystalline Form II of S-aticaprant is characterized by a differential scanning calorimetry thermogram comprising one or both endotherms at about 74.7° C. and about 96.2° C.

19. The method of claim 14, wherein the crystalline S-aticaprant is a crystalline Form III of S-aticaprant that is characterized by four or more x-ray diffraction pattern peaks at 2θ (±0.2) of 4.1°, 9.0°, 17.6°, 18.0°, and 21.4°.

20. The method of claim 19, wherein the crystalline Form III of S-aticaprant is characterized by a peak temperature ($T_m$) at about 121° C.

21. The method of claim 14, wherein the crystalline form of S-aticaprant is anhydrous.

22. The method of claim 14, further comprising adjunctive treatment with an effective amount of one or more antidepressants.

23. The method of claim 22, wherein the one or more antidepressants is a selective serotonin reuptake inhibitor, serotonin-norepinephrine reuptake inhibitor, or a combination thereof.

24. The method of claim 14, wherein the effective amount of the crystalline Form I, II, or III of S-aticaprant is between about 2 mg and about 35 mg, between about 5 mg and about 10 mg, about 5 mg, or about 10 mg.

25. The method of claim 14, wherein the crystalline Form I, II, or III of S-aticaprant is administered orally once daily.

26. The method of claim 14, wherein the patient has anhedonia.

27. The method of claim 19, wherein about 10 mg of the crystalline Form III is administered orally once daily.

28. The method of claim 27, further comprising adjunctive treatment with an effective amount of one or more antidepressants.

29. The method of claim 28, wherein the one or more antidepressants is a selective serotonin reuptake inhibitor, serotonin-norepinephrine reuptake inhibitor, or a combination thereof.

30. The method of claim 19, wherein the patient has anhedonia.

* * * * *